US008273787B2

(12) United States Patent
Bell et al.

(10) Patent No.: US 8,273,787 B2
(45) Date of Patent: Sep. 25, 2012

(54) ACTIVATED CYTOTOXIC COMPOUNDS FOR ATTACHMENT TO TARGETING MOLECULES FOR THE TREATMENT OF MAMMALIAN DISEASE CONDITIONS

(75) Inventors: Stanley C Bell, Narberth, PA (US); Glenn Fegley, Eagleville, PA (US); Stephen Cosenza, Voorhees, NJ (US); Jodie Duke, Newark, DE (US); Reddy E Premkumar, Villanova, PA (US); Reddy M. V. Ramana, Blue Bell, PA (US)

(73) Assignee: Onconova Therapeutics, Inc, Newtown, PA (US)

( * ) Notice: Subject to any disclaimer, the term of this patent is extended or adjusted under 35 U.S.C. 154(b) by 525 days.

(21) Appl. No.: 12/441,315

(22) PCT Filed: Sep. 14, 2007

(86) PCT No.: PCT/US2007/019943
§ 371 (c)(1),
(2), (4) Date: Mar. 13, 2009

(87) PCT Pub. No.: WO2008/033475
PCT Pub. Date: Mar. 20, 2008

(65) Prior Publication Data
US 2010/0022615 A1 Jan. 28, 2010

Related U.S. Application Data

(60) Provisional application No. 60/844,639, filed on Sep. 15, 2006.

(51) Int. Cl.
*A61K 31/40* (2006.01)
*C07D 207/46* (2006.01)
*C07K 16/00* (2006.01)
(52) U.S. Cl. ................. 514/425; 530/391.9; 548/542
(58) Field of Classification Search .............. 514/425; 530/391.9; 548/542
See application file for complete search history.

(56) References Cited

U.S. PATENT DOCUMENTS

| 6,359,013 B1 | 3/2002 | Reddy et al. |
| 6,767,926 B1 | 7/2004 | Cosenza et al. |

FOREIGN PATENT DOCUMENTS

| WO | WO03072062 | 9/2003 |
| WO | WO 03072062 A2 * | 9/2003 |
| WO | WO03072063 | 9/2003 |
| WO | WO2005089269 | 9/2005 |
| WO | WO 2005089269 A2 * | 9/2005 |

OTHER PUBLICATIONS

Bioconjugate Techniques (1996) by Greg T. Hermanson p. 187-227.*
Reddy, N. S. et al, Synthesis of New Coumarin 3-(N-aryl) Sulfonamides and Their Anticancer Activity, Bioorg Med Chem Lett (14):4093-5007 (2004).
Reddy, N.S et al, Novel Coumarin-3-(N-aryl) Carboxamides Arrest Breast Cancer Cell Growth by Inhibiting ErbB-2 and ERK1, Bioorg Med Chem (13):3141-3157 (2005).
Amsberry, K.L. et al, The Lactonization of 2'-Hydroxydydrocinnamic Acid Amides: A Potential Prodrug for Amines, J. Org. Chem 55(23):5867-5877 (1990).
Dubowchik, G.M., et al., Efficient Mitocycin C Coupling with Stable p-Nitropheny-Benzy Carbonates Using N-Hydroxybenzotriazole, Tetrahedron Letters, 30(30):5261-5264 (1997).
Rodrigues, M.L., et al., Synthesis and Beta-Lactamase-Mediated Activation of a Cephalosporin-Taxol Prodrug, Chem Biol. 2(4):223-7 (1995).
Shabat D., et al., Multiple Event Activation of a Generic Prodrug Trigger by Antibody Catlaysis, Proc Natl Acad Sci USA 96(12): 6925-30 (1999).
Shabat D., et al., In Vivo Activity in a Catalytic Antibody-Prodrug System: Antibody Catalyzed Etoposide Prodrug Activation for Selective Chemotherapy, Proc Natl Acad Sci USA (2001).
Marx C., et al., Validated High-Throughput Screening of Drug-Like Small Molecules for Inhibitors of ErbB2 Transcription. Assay Drug Dev. Technology 4(3):273-84 (2006).
Lostumbo, A., et al., Flow Cytometry: A New Approach for the Molecular Profiling of Breast Cancer, Exp. and Molecular Pathology 80:46-53 (2006).
Pellat-Deceunynk, C., et al., Human Myeloma Cell Lines As a Tool for Studying the Biology of Multiple Myeloma: A Reappraisal 18 Years After, Blood 86(10):4001-2 (1995).
IPER, Mar. 9, 2009, Onconova Therapeutics Inc.
Sunil S. Chandran et al., Latent Fluorophore Based on the Trimethyl Lock, J. Am. Chem. Soc. 127, 1652-1653 (2005).
Michael N. Levine et al, Trimethyl Lock: A Stable Chromogenic Substrate for Esterases, Molecules 13, 204-211 (2008).
Gooding, R.P., et al., Phenotypic And Molecular Analysis Of Six Human Cell Lines Derived From Patients With Plasma Cell Dyscrasia, British J. Haematology 106:669-688 (1999).
Harker, WG, Multidrug (Pleiotropic) Resistance In Doxorubicin-Selected Variants Of The Human Sarcoma Cell Line MES-SA, Cancer Res. 45(9):4091-6 (1985).
Fujimori, A., et al., Mutation At The Catalytic Site of Topoisomerase I In CEM/C2, A Human Leukemia Cell Line Resistant To Camptothecin, Cancer Res. 55(6): 1339-46 (1995).
Wijdenes, J., et al., A Plasmocyte Selective Monoclonal Antibody (B-B4) Recognizes Syndecan-1, Br J Haematol. 94(2):318-23 (1996).

(Continued)

*Primary Examiner* — Yong Chu
(74) *Attorney, Agent, or Firm* — Houri Khalilian; Law Offices of Khalilian Sira, LLC

(57) ABSTRACT

Activated cytotoxic compounds are described for attachment to targeting molecules for the treatment of a mammalian disease condition which comprise, an activator, a spacer linker, a linker (e.g., self-immolative), and a cytotoxic drug selected from the group consisting of AMINO-SUBSTITUTED (E)-2,6-DIALKOXYSTYRYL 4-SUBSTITUTED BENZYLSULFONES, AMINO-AND-HYDROXY SUBSTITUTED STYRYLSULFONANILIDES, and SUBSTITUTED PHENOXY- AND PHENYLTHIO-STYRYLSULFONE DERIVATIVES. Activated cytotoxic compound attached to a targeting molecule are described wherein the targeting molecule is selected from the group consisting essentially of an antibody, a receptor, a ligand, a cytokine, a hormone, and a signal transduction molecule. The invention is further directed to a method of treatment of disease conditions.

13 Claims, 8 Drawing Sheets

OTHER PUBLICATIONS

Tassone, P., et al., Cytotoxic Activity Of The Maytansinoid Immunoconjugate B-B4-DM1 Against CD138+ Multiple Myeloma Cells, Blood 104(12):3688-3696 (2004).

Amsberry, K.L. et al, Amine Prodrugs Which Utilize Hydroxy Amid Lactonization, Pharm. Res. 8, 323-330 (1991).

Greenwald et al, Drug Delivary Systems Based on Trimethyl Lock Lactonization, J. Med. Chem., 43, 475-487(2000).

White JG, Functional significance of mobile receptors on human platelets Arterioscler Thromb Vasc Biol, 13:1236-1243 (1993).

* cited by examiner

Alternative Monoclonal Antibody Conjugation Procedure:

A. Normal Human Fibroblasts and Prostate Cancer Cells Treated with ON 01500

B. Human Umbilical Vein Endothelial Cells and Prostate Cancer Cells Treated with ON 013100

US 8,273,787 B2

ACTIVATED CYTOTOXIC COMPOUNDS FOR ATTACHMENT TO TARGETING MOLECULES FOR THE TREATMENT OF MAMMALIAN DISEASE CONDITIONS

FIELD OF THE INVENTION

The current invention relates to activated cytotoxic compounds comprised of an activator, a spacer linker, a self-immolative linker, and a cytotoxic drug selected from the group consisting of AMINO-SUBSTITUTED (E)-2,6-DIALKOXYSTYRYL 4-SUBSTITUTED BENZYLSULFONES, AMINO-AND-HYDROXY SUBSTITUTED STYRYLSULFONANILIDES, and SUBSTITUTED PHENOXY- AND PHENYLTHIO-STYRYLSULFONE DERIVATIVES.

BACKGROUND OF THE INVENTION

Antibody-drug conjugates (ADCs)—monoclonal antibodies (mAbs) covalently linked to toxic agents are acknowledged and employed in the art as improved anticancer treatments. The combination of targeting specificity of mAbs with cytotoxic small molecules, allows for discrimination between malignant and normal tissues resulting in fewer toxic side effects exhibited by many conventional chemotherapies.

Currently, there exist only three FDA-approved ADCs available for cancer treatment. Two of the ADCs, Zevalin® and Bexxar®, comprise mAbs covalently attached to the radioisotopes Yttrium-90 and Iodine-131, respectively. These murine radiolabeled mAbs are used in the treatment of CD20-expressing B-cell lymphomas. The third FDA-approved ADC, Mylotarg®, consists of a humanized anti-CD33 monoclonal antibody conjugated to the DNA-cleaving enediyne antibiotic, Calicheamicin. To date, this is the only approved immunoconjugate possessing a cytotoxic organic molecule.

Recently, groups at the National Cancer Institute (NCI) reported on the preparation and evaluation of immunoconjugates composed of HERCEPTIN® (Trastuzumab) and the cytotoxin, Geldanamycin. Mandler, R., et al., *Trastuzumab-Geldanamycin Immunoconjugates: Pharmacokinetics, Biodistribution, and Enhanced Antitumor Activity*, Cancer Res. 64:1460-1467 (2004). Geldanamycin is a highly cytotoxic ansamycin benzoquinone antibiotic that exerts its cytotoxicity by binding to the protein chaperone heat shock protein 90 (hsp 90). The anticancer potential of Geldanamycin as a single chemotherapeutic agent has been abandoned as a result of its nonselective and severe toxicity. Geldanamycin is unique in that targeting of hsp90 is effective at down-regulating HER2, and thus tumor cells that over express HER2 are especially sensitive to Geldanamycin. Trastuzumab-Geldanamycin was shown to have $IC_{50}s$ 10-200-fold lower than that of unmodified Trastuzumab in antiproliferative assays. In a xenograft murine model, consisting of weekly i.p. doses of 4 mg/kg over four months, animals treated with Trastuzumab-Geldanamycin exhibited 69% tumor regression, whereas those treated with Trastuzumab alone only showed 7% regression. Median survival time was 145 days as opposed to 78 days for Trastuzumab-treated animals. In addition, nearly one-third of the mice remained tumor free two months after treatment had been completed, whereas there were no survivors from the Trastuzumab group.

Nearly all organic anticancer agents are associated with dose-limiting toxicities. A significant need exists to improve drug efficacy while minimizing systemic toxicity while addressing optimization parameters, such as physiological barriers to targeting molecule extravasation and intratumoral penetration, immunonconjugate aggregation, immunogenicity, normal tissue expression of targeted antigens, and inefficient drug release from the carrier. Certain compounds, moreover, require an improved delivery system due to physicochemical properties such as water solubility, cellular uptake, as well as otherwise short half-life in vivo. Since prognosis of long-term, disease-free survival of most cancer patients remains poor, there continues to be a critical unmet need for improved anticancer treatment.

SUMMARY OF THE INVENTION

The present invention is directed to activated cytotoxic compound for attachment to a targeting molecule for the treatment of a mammalian disease condition comprising, an activator, a spacer linker, a self-immolative linker, and a cytotoxic drug selected from the group consisting of AMINO-SUBSTITUTED (E)-2,6-DIALKOXYSTYRYL 4-SUBSTITUTED BENZYLSULFONES, AMINO-AND-HYDROXY SUBSTITUTED STYRYLSULFONANILIDES, and SUBSTITUTED PHENOXY- AND PHENYLTHIO-STYRYLSULFONE DERIVATIVES.

In addition, the current invention is directed to activated cytotoxic compound attached to a targeting molecule for the treatment of a mammalian disease condition wherein the targeting molecule is selected from the group consisting essentially of an antibody, a receptor, a ligand, a cytokine, a hormone, and a signal transduction molecule.

The invention is further directed to a method of treatment of a disease condition in a mammal comprising administering a therapeutically effective amount to said mammal of an activated cytotoxic compound attached to a targeting molecule for the treatment of a mammalian disease condition.

DETAILED DESCRIPTION OF THE INVENTION

Figure 1A:
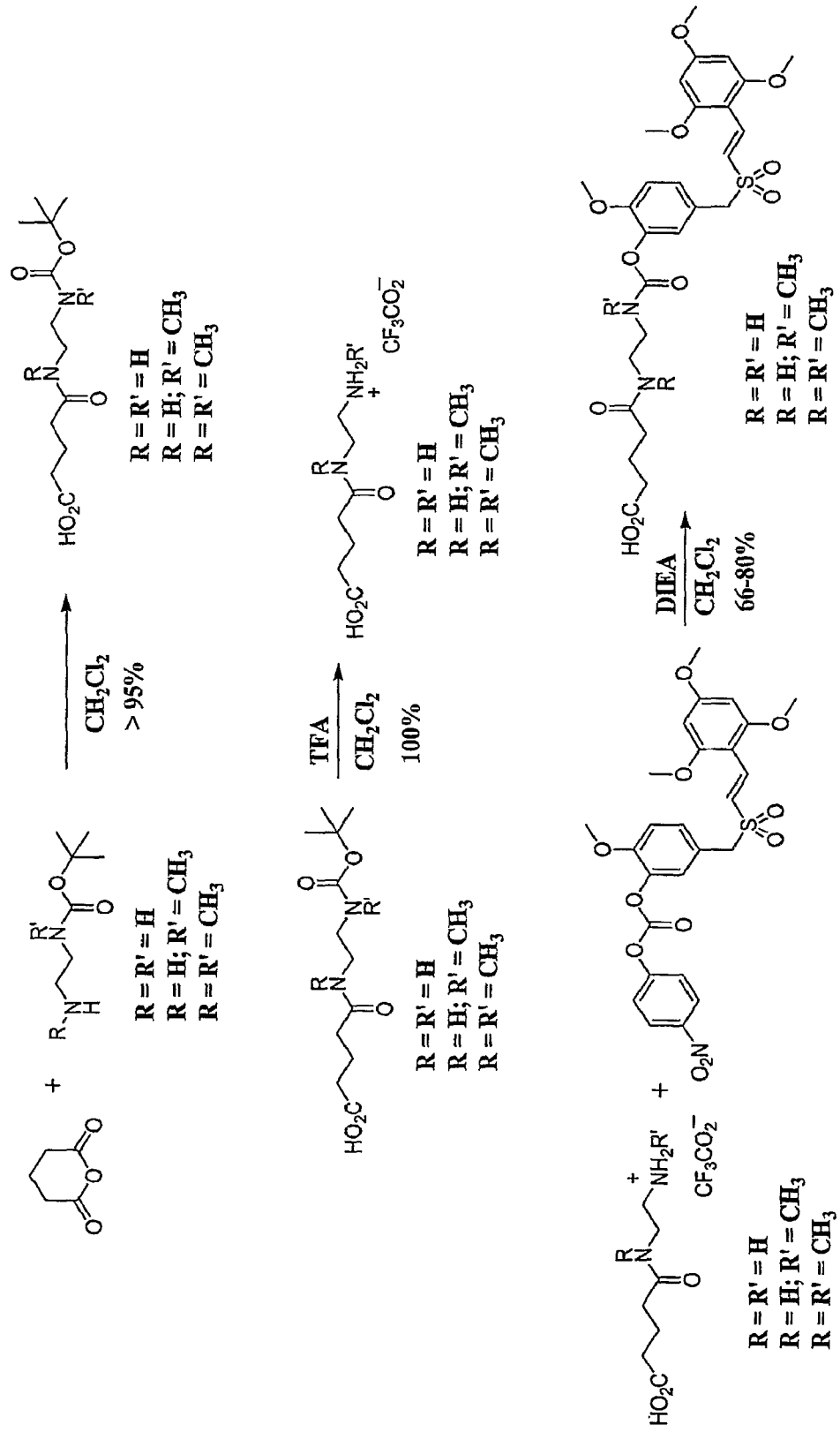
FIGS. 1A and 1B display example synthetic schemes for activated cytotoxic compounds (ON 12013100, ON 14013100, and ON 16013100) suitable for attachment to targeting molecules.

Unless defined otherwise, all technical and scientific terms used herein have the same meaning as is commonly understood by one of skill in the art to which this invention belongs. All publications and patents referred to herein are incorporated by reference.

Targeting molecule as used herein refers to an entity comprising a protein molecular component, including multimeric proteins, or a peptide. Preferred targeting molecules as elements of drug delivery entities described herein include, for example, an antibody, a receptor, a ligand, or a hormone. The term antibody, as used herein, refers to whole as well as functional fragments of antibodies, including but not limited to monoclonal antibodies, e.g., humanized and/or chimeric.

By choosing targeting molecules that possess the capability to internalize upon binding to its cell surface antigen, in addition to the careful selection of mechanism-based self-immolative chemical linkers, cytotoxic compounds attached to targeting molecules described herein amplify the tumor-killing properties of the original cytotoxic payload.

Chimeric and humanized mAbs that minimize immunogenicity, yet have very high affinities for tumor-associated antigens, as well as mAbs that efficiently internalize into cells upon binding to the target domain are now known in the art. The carefully designed linker technology described herein combined with improved monoclonal antibodies and the compounds with high potencies provide a significant advantage to treat disease conditions.

Compounds

Onconova Therapeutics, Inc. possesses a portfolio of highly potent cell cycle inhibitors that are based around a benzyl styryl sulfone chemotype. Benzyl styryl sulfones include cytotoxic agents, which inhibit various kinases that are important in cell cycle progression. Within the portfolio, Onconova Therapeutics has identified and developed a number of benzyl styryl sulfones that kill tumor cells in the low nanomolar range, inhibit specific kinases, and protects normal cells and mice from lethal doses of ionizing radiation and cytotoxic compounds. Reddy, E. P., and Reddy, M. V., Styryl Sulfone Anticancer Agents, U.S. Pat. No. 6,359,013 (2002); Reddy, N. S., Mallireddigari, M. R., Cosenza, S. C., Gummireddy, K., Bell, S. C., Reddy, E. P., and Reddy, M. V. *Synthesis of New Coumarin 3-(N-aryl) Sulfonamides and Their Anticancer Activity*, Bioorg Med Chem Lett (14):4093-5007 (2004); Reddy, N. S., Gummireddy, K., Mallireddigari, M. R., Cosenza, S. C., Venkatapuram, P., Bell, S. C., Reddy, E. P., and Reddy, M. V. *Novel Coumarin-3-(N-aryl) Carboxamides Arrest Breast Cancer Cell Growth by Inhibiting ErbB-2 and ERK1*, Bioorg Med Chem (13):3141-3157 (2005); Cosenza, S. C., Reddy, M. V., and Reddy, E. P, Method for Protecting Normal Cells From Cytotoxicity of Chemotherapeutic Agents, U.S. Pat. No. 6,767,926 (2004).

One of these molecules, ON 01910.Na is currently in phase I clinical trials at Johns Hopkins and Mount Sinai Hospitals (ND#66780). Structure-activity relationships (SARs) have been carefully mapped for this class of compound, in the context of substitutions about either aromatic ring. Two compounds from this class contain amino and hydroxyl groups on the benzyl ring, respectively, ON 01500 ((E)-2,4,6-trimethoxystyryl-4-methoxy-3-aminobenzylsulfone) and ON 013100 ((E)-5-((2,4,6-trimethoxystyrylsulfonyl)methyl)-2-methoxyphenol), are particularly preferred cytotoxic drug elements of the activated cytotoxic compound described herein. The amino and hydroxyl groups on the benzyl ring, for example, accommodates conjugation to biomolecules such as amino acids, peptides, proteins, and antibodies.

Many of the compounds within this library are unique in that they exhibit low nanomolar activity against a broad spectrum of cancer cells with the benefit of not being affected by MDR-mediated drug resistance. In addition, the majority of these molecules has molecular weights below 500 g/mole, and can be efficiently synthesized in only five or six chemical steps. The Data Section describe the biological activities of ON 01500 and ON 013100, for example. Each of these molecules possess unique biological and chemical properties, and are ideally suited for immunoconjugate-based, for example, tumor targeting. These compounds are more suited for use within immunoconjugates, for example, rather than as stand alone chemotherapeutics due to physicochemical properties such as water solubility, cellular uptake, as well as otherwise short half-life in the circulation.

See, particularly, the published PCT international applications WO03072062, entitled AMINO-SUBSTITUTED (E)-2,6-DIALKOXYSTYRYL 4-SUBSTITUTED BENZYL-SULFONES FOR TREATING PROLIFERATIVE DISORDERS, published Sep. 4, 2003; WO03072063 entitled AMINO-SUBSTITUTED SULFONANILIDES AND DERIVATIVES THEREOF FOR TREATING PROLIFERATIVE DISORDERS, published Sep. 4, 2003; and, WO2005089269 entitled SUBSTITUTED PHENOXY- AND PHENYLTHIO-DERIVATIVES FOR TREATING PROLIFERATIVE DISORDERS, published Sep. 29, 2005.

Cytotoxic compounds contemplated and exemplified herein are important elements of the activated and conjugated entities of the present invention, in part, because each is highly active and selective against tumor cells, each is active against multidrug resistant tumor cells, each is active in in vivo models. The simple and flexible chemical structures of the cytotoxic drugs described herein make them ideally suited for conjugation as well as large-scale production.

Compounds of formula I immediately below are example cytotoxic compounds for employment as elements of the drug-delivery entities described herein:

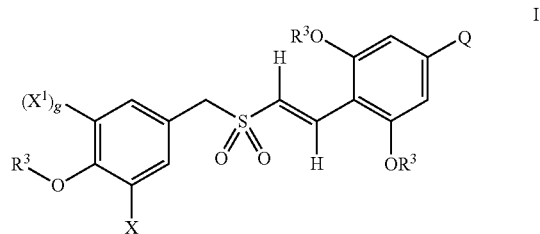

wherein:

X is selected from the group consisting of (i) and (ii) below:

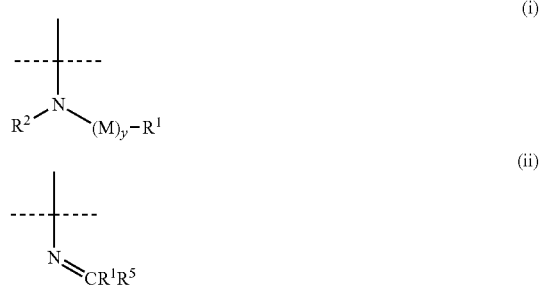

$X^1$ is selected from the group consisting of (i), (ii) and (iii) below:

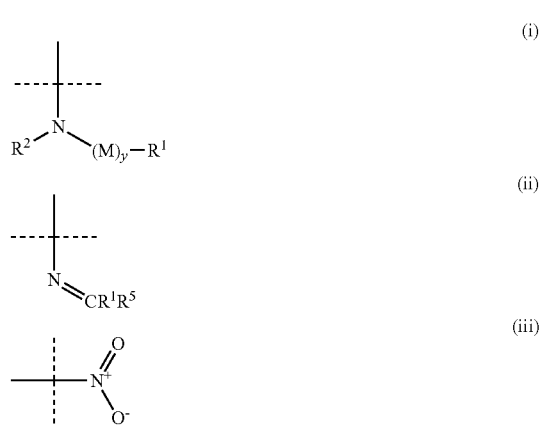

wherein $X^1$ is optionally protected with one or more chemical protecting groups;

g is 0 or 1;

each M is a bivalent connecting group independently selected from the group consisting of —$(C_1$-$C_6)$alkylene-, —$(CH_2)_a$—V—$(CH_2)_b$—, —$(CH_2)_d$—W—$(CH_2)_e$— and —Z—;

each y is independently selected from the group consisting of 0 and 1;

each V is independently selected from the group consisting of arylene, heteroarylene, —C(=O)—, —C(=S)—, —S(=O)—, —$SO_2$—, —C(=O)O—, —C(=O)$(C_1$-$C_6)$perfluoroalkylene-, —C(=O)$NR^4$—, —C(=S)$NR^4$— and —$SO_2NR^4$—;

each W is independently selected from the group consisting of —$NR^4$—, —O— and —S—;

each a is independently selected from the group consisting of 0, 1, 2 and 3;

each b is independently selected from the group consisting of 0, 1, 2 and 3;

each d is independently selected from the group consisting of 1, 2 and 3;

each e is independently selected from the group consisting of 0, 1, 2 and 3;

—Z— is

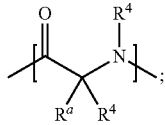

wherein the absolute stereochemistry of —Z— is D or L or a mixture of D and L;

each $R^a$ is independently selected from the group consisting of —H, —$(C_1$-$C_6)$alkyl, —$(CH_2)_3$—NH—C$(NH_2)$(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —CH$(CH_3)$—$CH_2$—$CH_3$, —$CH_2$CH$(CH_3)_2$, —$(CH_2)_4$—$NH_2$, —$(CH_2)_2$—S—$CH_3$, phenyl, $CH_2$-phenyl, —$CH_2$—OH, —CH(OH)—$CH_3$, —$CH_2$-(3-indolyl), —$CH_2$-(4-hydroxyphenyl), —CH$(CH_3)_2$ and —$CH_2$—$CH_3$; and includes compounds wherein $R^a$ and $R^1$ combine to form a 5-, 6- or 7-membered heterocyclic ring;

each $R^1$ is independently selected from the group consisting of —H, unsubstituted aryl, substituted aryl, substituted heterocyclic, unsubstituted heterocyclic, —$CO_2R^5$, —C(=O)$NR^4_2$, —$CR^4R^6R^7$, —C(=NH)—$NR^4_2$, —$(C_1$-$C_6)$perfluoroalkyl, —$CF_2$Cl, —P(=O)$(OR^4)_2$, —OP(=O)$(OR^4)_2$ and a monovalent peptidyl moiety with a molecular weight of less than 1000; provided that when y is 0 and $R^1$ is —$CO_2R^5$, $R^5$ is not —H;

each $R^2$ is independently selected from the group consisting of —H, —$(C_1$-$C_6)$alkyl, and aryl$(C_1$-$C_3)$alkyl, wherein —$R^2$ and -$(M)_y$-$R^1$ may optionally be linked covalently to form a 5-, 6- or 7-membered substituted or unsubstituted heterocycle;

each $R^3$ is independently selected from —$(C_1$-$C_6)$alkyl;

each $R^4$ is independently selected from the group consisting of —H, and —$(C_1$-$C_6)$alkyl;

each $R^5$ is independently selected from the group consisting of —H, —$(C_1$-$C_6)$alkyl and —$(C_1$-$C_6)$acyl;

each $R^6$ is independently selected from the group consisting of —H, —$(C_1$-$C_6)$alkyl, —$CO_2R^5$, —C(=O)$R^7$, —$OR^5$, —OC(=O)$(CH_2)_2CO_2R^5$, —$SR^4$, guanidino, —$NR^4_2$, —$NR^4_3{}^+$, —$N^+(CH_2CH_2OR^5)_3$, phenyl, substituted phenyl, heterocyclic, substituted heterocyclic and halogen;

each $R^7$ is independently selected from the group consisting of —$R^a$, halogen, —$NR^4_2$, and heterocycles containing two nitrogen atoms; and Q is selected from the group consisting of —H, —$(C_1$-$C_6)$alkoxy, halogen, —$(C_1$-$C_6)$alkyl and —$NR^4_2$;

wherein the substituents for the substituted aryl and substituted heterocyclic groups comprising or included within $R^1$, $R^2$, $R^a$, $R^6$ and $R^7$, are independently selected from the group consisting of halogen, $(C_1$-$C_6)$alkyl, —$NO_2$, —C≡N, —$CO_2R^5$, —C(=O)O$(C_1$-$C_3)$alkyl, —$OR^5$, —$(C_2$-$C_6)$—OH, phosphonato, —$NR^4_2$, —NHC(=O)$(C_1$-$C_6)$alkyl, sulfamyl, —OC(=O)$(C_1$-$C_3)$alkyl, —O$(C_2$-$C_6)$—N$((C_1$-$C_6)$alkyl$)_2$ and —$CF_3$;

provided (1) when $R^1$ is a monovalent peptidyl moiety of molecular weight less than 1000 and V is —C(=O)—, —C(=S)—, —S(=O)— or —$SO_2$—, and b is 0;

then said peptidyl moiety is coupled to M through the amino terminus of the peptidyl moiety or through a sidechain amino group to form an amide, thioamide, sulfinamide or sulfonamide respectively;

(2) when $R^1$ is a monovalent peptidyl moiety of molecular weight less than 1000 and V is —C(=O)$NR^3$—, —$SO_2NR^3$—, or —$NR^4$—, and b is 0, then said peptidyl moiety is coupled to M through the carboxy terminus of the peptidyl moiety or through a sidechain carboxyl group to form an imide, sulfonimide, or carboxamide respectively; and (3) when $R^1$ is a monovalent peptidyl moiety of molecular weight less than 1000 and W is —S— or —O—, and d is 0, then said peptidyl moiety is coupled to M through the carboxy terminus of the peptidyl moiety or through a sidechain carboxyl group to form a carbothioic acid ester or the carboxylic ester respectively;

or a salt of such a compound. Compounds are preferred wherein each V is independently selected from the group consisting of —C(=O)—, —C(=S)—, —S(=O)—, —$SO_2$—, —C(=O)$NR^4$—, —C(=S)$NR^4$— and —$SO_2NR^4$—;

—Z— is

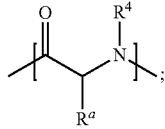

wherein the absolute stereochemistry of —Z— is either D or L each $R^a$ is independently selected from the group consisting of —H, —$CH_3$, —$(CH_2)_3$—NH—C$(NH_2)$(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —CH$(CH_3)$—$CH_2$—$CH_3$, —$CH_2$CH$(CH_3)_2$, —$(CH_2)_4$—$NH_2$, —$(CH_2)_2$—S—$CH_3$, phenyl, $CH_2$-phenyl, —$CH_2$—OH, —CH(OH)—$CH_3$, —$CH_2$-(3-indolyl), —$CH_2$-(4-hydroxyphenyl), —CH$(CH_3)_2$ and —$CH_2$—$CH_3$; and includes compounds wherein $R^a$ and $R^1$ combine to form a 5-, 6- or 7-membered heterocyclic ring;

each $R^1$ is independently selected from the group consisting of —H, unsubstituted aryl, substituted aryl, substituted heterocyclic, unsubstituted heterocyclic, —$CO_2R^5$, —C(=O)$NR^4_2$, —$CHR^6R^7$, —C(=NH)—$NR^4_2$, and a monovalent peptidyl moiety with a molecular weight of less than 1000; provided that when y is 0 and $R^1$ is —$CO_2R^5$, $R^5$ is not —H;

each $R^6$ is independently selected from the group consisting of —H, —$(C_1$-$C_6)$alkyl, —$CO_2R^5$, —C(=O)$R^7$, —OH, —$SR^4$, —$(C_1$-$C_3)$alkoxy, —$(C_1$-$C_3)$alkylthio, guanidino, —$NR^4_2$, phenyl, substituted phenyl, heterocyclic, substituted heterocyclic and halogen; and each $R^7$ is independently selected from the group consisting of —H, halogen, —$(C_1$-$C_6)$alkyl, —$NR^4_2$ and heterocycles containing two nitrogen atoms;

wherein the substituents for the substituted aryl and substituted heterocyclic groups comprising or included within $R^1$, $R^a$, $R^6$ and $R^7$, are independently selected from the group consisting of halogen, $(C_1-C_6)$alkyl, $(C_1-C_6)$alkoxy, $-NO_2$, $-C\equiv N$, $-CO_2R^5$, $-C(=O)O(C_1-C_3)$alkyl, $-OH$, $-(C_2-C_6)-OH$, phosphonato, $-NR^4_2$, $-NHC(=O)(C_1-C_6)$alkyl, sulfamyl, $-OC(=O)(C_1-C_3)$alkyl, $-O(C_2-C_6)-N((C_1-C_6)\text{alkyl})_2$ and $-CF_3$;
or a salt of such a compound. Exemplary compounds of this formula are wherein;
X is

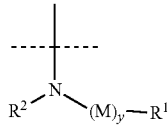

y is 0; and $R^2$ is —H. Embodiments of this structure are further preferred, for example, that fall within formula III:

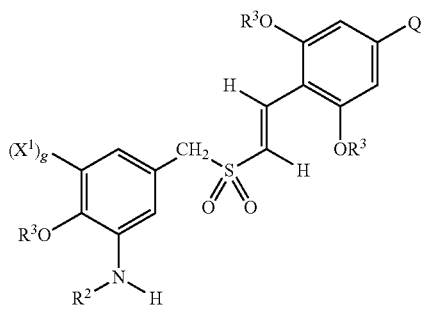

wherein:
$X^1$ is selected from the group consisting of (i), (ii) and (iii) below:

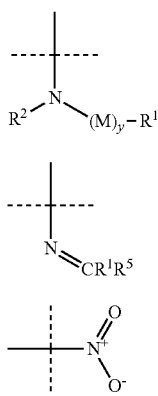

wherein $X^1$ is optionally protected with one or more chemical protecting groups;
g is 0 or 1;
M is a bivalent connecting group selected from the group consisting of —$(C_1-C_6)$alkylene-, —$(CH_2)_a$—V—$(CH_2)_b$—, —$(CH_2)_d$—W—$(CH_2)_e$— and —Z—;
y is selected from the group consisting of 0 and 1;
each V is independently selected from the group consisting of —C(=O)—, —C(=S)—, —S(=O)—, —SO_2—, —C(=O)NR^4—, —C(=S)NR^4— and —SO_2NR^4—;

each W is independently selected from the group consisting of —NR^4—, —O— and —S—;
each a is independently selected from the group consisting of 0, 1, 2 and 3;
each b is independently selected from the group consisting of 0, 1, 2 and 3;
each d is independently selected from the group consisting of 1, 2 and 3;
each e is independently selected from the group consisting of 0, 1, 2 and 3;
—Z— is

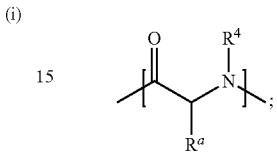

wherein the absolute stereochemistry of —Z— is either D or L;
$R^a$ is selected from the group consisting of —H, —CH_3, —(CH_2)_3—NH—C(NH_2)(=NH), —CH_2C(=O)NH_2, —CH_2COOH, —CH_2SH, —(CH_2)_2C(=O)—NH_2, —(CH_2)_2COOH, —CH_2-(2-imidazolyl), —CH(CH_3)—CH_2—CH_3, —CH_2CH(CH_3)_2, —(CH_2)_4—NH_2, —(CH_2)_2—S—CH_3, phenyl, CH_2-phenyl, —CH_2—OH, —CH(OH)—CH_3, —CH_2—(3-indolyl), —CH_2-(4-hydroxyphenyl), —CH(CH_3)_2 and —CH_2—CH_3; and includes compounds wherein $R^a$ and $R^1$ combine to form a 5-, 6- or 7-membered heterocyclic ring;
each $R^1$ is independently selected from the group consisting of —H, unsubstituted aryl, substituted aryl, substituted heterocyclic, unsubstituted heterocyclic, —CO_2R^5, —C(=O)NR^4_2, —CHR^6R^7, —C(=NH)—NR^4_2 and a monovalent peptidyl moiety with a molecular weight of less than 1000; provided that when y is 0 and $R^1$ is —CO_2R^5, $R^5$ is not —H;
each $R^2$ is independently selected from the group consisting of —H, —$(C_1-C_6)$alkyl, and aryl$(C_1-C_3)$alkyl, wherein —$R^2$ and -(M)_y-$R^1$ may optionally be linked covalently to form a 5-, 6- or 7-membered substituted or unsubstituted heterocycle;
each $R^3$ is independently selected from —$(C_1-C_6)$alkyl;
each $R^4$ is independently selected from the group consisting of —H, and —$(C_1-C_6)$alkyl;
each $R^5$ is independently selected from the group consisting of —H, —$(C_1-C_6)$alkyl and —$(C_1-C_6)$acyl;
each $R^6$ is independently selected from the group consisting of —H, —$(C_1-C_6)$alkyl, —CO_2R^5, —C(=O)R^7, —OH, —SR^4, —$(C_1-C_3)$alkoxy, —$(C_1-C_3)$alkylthio, guanidino, —NR^4_2, phenyl, substituted phenyl, heterocyclic, substituted heterocyclic and halogen;
each $R^7$ is independently selected from the group consisting of —H, halogen, —$(C_1-C_6)$alkyl, —NR^4_2, and heterocycles containing two nitrogen atoms; and
Q is selected from the group consisting of —H, —$(C_1-C_6)$alkoxy, halogen, —$(C_1-C_6)$alkyl and —NR^4_2;
wherein the substituents for the substituted aryl and substituted heterocyclic groups comprising or included within $R^1$, $R^2$, $R^a$, $R^6$ and $R^7$, are independently selected from the group consisting of halogen, $(C_1-C_6)$alkyl, $(C_1-C_6)$alkoxy, —NO_2, —C≡N, —CO_2R^5, —C(=O)O(C_1-C_3)$alkyl, —OH, —$(C_2-C_6)$—OH, phosphonato, —NR^4_2, —NHC(=O)(C_1-C_6)$alkyl, sulfamyl, —OC(=O)(C_1-C_3)$alkyl, —O(C_2-C_6)—N((C_1-C_6)$alkyl)_2 and —CF_3;
provided
(1) when $R^1$ is a monovalent peptidyl moiety of molecular weight less than 1000 and V is —C(=O)—, —C(=S)—, —S(=O)— or —SO_2—, and b is 0;

then said peptidyl moiety is coupled to M through the amino terminus of the peptidyl moiety or through a sidechain amino group to form an amide, thioamide, sulfinamide or sulfonamide respectively;

(2) when $R^1$ is a monovalent peptidyl moiety of molecular weight less than 1000 and V is —C(=O)NR$^3$—, —SO$_2$NR$^3$—, or —NR$^4$—, and b is 0, then said peptidyl moiety is coupled to M through the carboxy terminus of the peptidyl moiety or through a sidechain carboxyl group to form an imide, sulfonimide, or carboxamide respectively; and (3) when $R^1$ is a monovalent peptidyl moiety of molecular weight less than 1000 and W is —S— or —O—, and d is 0, then said peptidyl moiety is coupled to M through the carboxy terminus of the peptidyl moiety or through a sidechain carboxyl group to form a carbothioic acid ester or the carboxylic ester respectively;

or a salt of such a compound. Compounds are particularly preferred which have the formula IIIa:

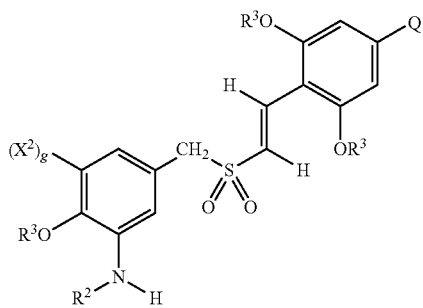

IIIa wherein:
$X^2$ is selected from the group consisting of NO$_2$ and —NH$_2$, optionally protected with a chemical protecting group;
g is 0 or 1;
each $R^3$ is independently selected from —(C$_1$-C$_6$)alkyl;
each $R^4$ is independently selected from the group consisting of —H, and —(C$_1$-C$_6$)alkyl;
Q is selected from the group consisting of —H, —(C$_1$-C$_6$) alkoxy, halogen, —(C$_1$-C$_6$)alkyl and —NR$^4$$_2$. Particularly, wherein Q is —(C$_1$-C$_6$)alkoxy or wherein Q is —OCH$_3$. Compounds are further preferred wherein $R^3$ is —CH$_3$, or a salt of such a compound. An exemplary compound is (E)-2,4,6-trimethoxystyryl-4-methoxy-3-aminobenzylsulfone, or a salt of such a compound.

Compounds of another formula I shown immediately below are further example cytotoxic compounds for employment as elements of the drug-delivery entities described herein:

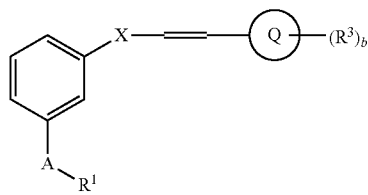

I wherein,
A is —S— or —O—;
$R^1$ is selected from the group consisting of —H, halo(C$_1$-C$_6$)alkyl, —C(=O)R$^w$, —S(=O)R$^w$, —SO$_2$R$^w$; —(C$_1$-C$_6$ hydrocarbylene)R$^z$, —P(=O)(OR$^v$)$_2$, —C(R$^a$)(R$^v$)—C(=O)—R$''$, substituted and unsubstituted aryl, substituted and unsubstituted heteroaryl, —Si[(C$_1$-C$_6$)alkyl]$_3$, and —CH$_2$CH$_2$Si[(C$_1$-C$_6$)alkyl]$_3$;

each $R^v$ is independently selected from the group consisting of —H and —(C$_1$-C$_7$)hydrocarbyl;

$R^w$ is selected from the group consisting of —(C$_1$-C$_7$) hydrocarbyl, —NR$^v$$_2$; —OR$^v$, halo(C$_1$-C$_3$ alkyl), —NR$^v$CR$^v$R$^a$—C(=O)—R$''$, —CR$^v$R$^a$—N(R$^v$)—R$^c$, substituted and unsubstituted aryl, substituted and unsubstituted aryl(C$_1$-C$_3$)alkyl, substituted and unsubstituted heteroaryl, substituted and unsubstituted heteroaryl(C$_1$-C$_3$)alkyl, substituted and unsubstituted heterocyclyl, substituted and unsubstituted heterocyclyl(C$_1$-C$_3$)alkyl, —(C$_1$-C$_3$ alkylene)P(=O)(OR$^v$)$_2$, —(C$_1$-C$_3$)perfluoroalkylene-N(CH$_3$)$_2$, —(C$_1$-C$_3$)alkylene-N$^+$(C$_1$-C$_3$)$_3$, —(C$_1$-C$_3$)alkylene-N$^+$(CH$_2$CH$_2$OH)$_3$, —(C$_1$-C$_4$alkylene)-C(=O)-halogen, —(C$_1$-C$_4$)perfluoroalkylene-CO$_2$R$^v$, —(C$_1$-C$_3$alkylene)C(=O) OR$^v$, and —(C$_1$-C$_3$alkylene)OC(=O)—(C$_1$-C$_3$ alkylene)C(=O)R$^y$;

$R^y$ is selected from the group consisting of —OR$^v$, —NR$^v$$_2$ and —(C$_1$-C$_6$)alkyl;

$R^z$ is selected from the group consisting of —C(=O)R$^y$, —NR$^v$CR$^v$R$^a$—C(=O)—R$''$, —NR$^v$$_2$, —OR$^v$, substituted and unsubstituted aryl, substituted and unsubstituted heteroaryl and —C(=O)(C$_1$-C$_3$)alkyl;

each $R^a$ is independently selected from the group consisting of —H, —(C$_1$-C$_6$)alkyl, —(C$_1$-C$_6$)heteroalkyl, —(CH$_2$)$_3$—NH—C(NH$_2$)(=NH), —CH$_2$C(=O)NH$_2$, —CH$_2$COOH, —(CH$_2$)$_2$COOH, substituted and unsubstituted aryl, substituted and unsubstituted aryl(C$_1$-C$_3$)alkyl, substituted and unsubstituted heterocyclyl, and substituted and unsubstituted heterocyclyl(C$_1$-C$_3$)alkyl;

each $R''$ is independently selected from the group consisting of —OR$^v$, —NR$^v$$_2$, and an N-terminally linked peptidyl residue containing from 1 to 3 amino acids in which the terminal carboxyl group of the peptidyl residue is present as a functional group selected from the group consisting of —CO$_2$R$^v$ and —C(=O)NR$^v$$_2$;

each $R^c$ is independently selected from the group consisting of —H and a carboxy terminally linked peptidyl residue containing from 1 to 3 amino acids in which the terminal amino group of the peptidyl residue is present as a functional group selected from the group consisting of —NH$_2$, —NHC(=O)(C$_1$-C$_6$)alkyl, —NH(C$_1$-C$_6$)alkyl, —NH(C$_1$-C$_6$ alkyl)$_2$ and —NHC(=O)O(C$_1$-C$_7$)hydrocarbyl;

Q is aryl or heteroaryl;
each $R^2$ and $R^3$ are independently selected from the group consisting of halogen, —(C$_1$-C$_7$)hydrocarbyl, —C(=O)R$^v$, —NR$^v$$_2$, —NHC(=O)R$^v$, —NHSO$_2$R$^v$; —NHR$^a$, —NH-CR$^v$R$^a$C(=O)R$''$, —NHSO$_2$R$^v$, —C(=O)OR$^v$, —C(=O) NHR$^v$, —NO$_2$, —CN, —OR$^v$, —P(=O)(OR$^v$)$_2$, —C(=NH) NH$_2$, dimethylamino(C$_2$-C$_6$)alkoxy, —NHC(=NR$^v$)NHR$^v$, —(C$_1$-C$_6$)haloalkyl, and —(C$_1$-C$_6$)haloalkoxy;

wherein, the two R$^v$ groups on —P(=O)(OR$^v$)$_2$ and —NR$^v$$_2$ may optionally form a five- or six-membered heterocyclic ring, which may further optionally be fused to an aryl or carbocyclic ring;

a is 0, 1, 2 or 3;
b is 0, 1, 2 or 3;
the conformation of the substituents on the exocyclic carbon-carbon double bond is either E- or Z-;
X is —C*H(R$^x$)Y— or —NR$^x$—Z—;
Y is —S(=O)— or —SO$_2$—;
Z is —C(=O)— or —SO$_2$—;
$R^x$ is selected from the group consisting of —H, —(C$_1$-C$_6$) alkyl, and —C(=O)(C$_1$-C$_6$)alkyl; and
* indicates that, when $R^x$ is other than —H, the conformation of the substituents on the designated carbon atom is (R)-, (S)- or any mixture of (R)- and (S)-; or a salt of such a compound;
provided that;
(a) when A is —O— and $R^1$ is —H;
b is greater than 0; and
$R^3$ is other than $(C_1-C_6)$alkyl, —OH and —$NO_2$.
(b) when X is —$NR^x$—Z— and A is —O—;
$R^z$ is other than —C(=O)$R^y$, —$NR^v_2$ and unsubstituted aryl; and
$R^w$ is other than —$(C_1-C_6)$alkyl; and
(c) when X is —C*H($R^x$)Y— and A is —O—;
$R^1$ is other than halo$(C_1-C_6)$alkyl and unsubstituted aryl;
$R^z$ is other than —$NR^v_2$ and unsubstituted aryl; and
$R^w$ is other than —$(C_1-C_7)$hydrocarbyl. Compounds of this type are preferred that fall into Formula II:

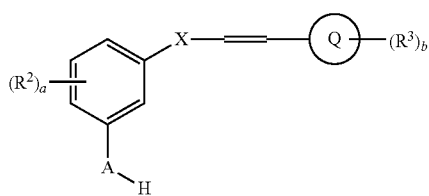

II wherein $R^2$, $R^3$, A, a, b, X and Q are as defined as in claim 1;

or a salt thereof. Compounds of this configuration are particularly preferred that follow Formula IIA:

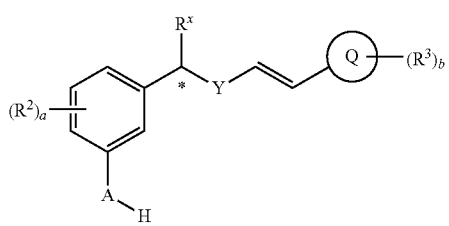

IIA wherein $R^2$, $R^3$, a, b, A, Y, Q and * are as defined as in claim 9; and $R^x$ is selected from the group consisting of —H, —$(C_1-C_6)$ alkyl, and —C(=O)$(C_1-C_6)$alkyl. Preferred embodiments of these cytotoxic compounds are wherein $R^x$ is —H. An exemplary embodiment, for example, is (E)-5-((2,4,6-trimethoxystyrylsulfonyl)methyl)-2-methoxyphenol.

Further, compounds of formula I immediately below are example cytotoxic compounds for employment as elements of the drug-delivery entities described herein:

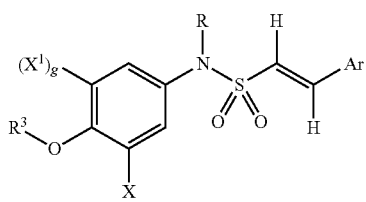

I wherein:

Ar is selected from the group consisting of substituted and unsubstituted aryl, and substituted and unsubstituted heteroaryl;

X is selected from the group consisting of (i) and (ii) below:

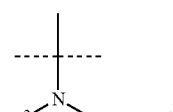

(i)

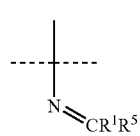

(ii)

$X^1$ is selected from the group consisting of (i), (ii) and (iii) below:

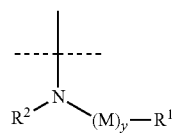

(i)

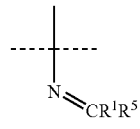

(ii)

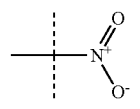

(iii)

wherein $X^1$ is optionally protected with one or more chemical protecting groups;

g is 0 or 1;

each M is a bivalent connecting group independently selected from the group consisting of —$(C_1-C_6)$alkylene-, —$(CH_2)_a$—V—$(CH_2)_b$—, —$(CH_2)_d$—W—$(CH_2)_e$— and —Z—;

each y is independently selected from the group consisting of 0 and 1;

each V is independently selected from the group consisting of —C(=O)—, —C(=O)—O—, —C(=O)—(C1-C6)perfluoroalkylene, —C(=S)—, —S(=O)—, —$SO_2$—, —C(=O)$NR^4$—, —C(=S)$NR^4$— and —$SO_2NR^4$—;

each W is independently selected from the group consisting of —$NR^4$—, —O— and —S—;

each a is independently selected from the group consisting of 0, 1, 2 and 3;

each b is independently selected from the group consisting of 0, 1, 2 and 3;

each d is independently selected from the group consisting of 1, 2 and 3;

each e is independently selected from the group consisting of 0, 1, 2 and 3;

—Z— is

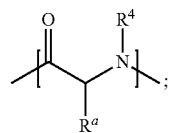

wherein the absolute stereochemistry of —Z— is D or L, or a mixture of D and L;

R is selected from the group consisting of —H, $(C_1-C_6)$alkyl, $(C_1-C_6)$alkoxy, $(C_3-C_6)$alkenyl, $(C_2-C_6)$heteroalkyl, $(C_3-C_6)$heteroalkenyl, $(C_2-C_6)$hydroxyalkyl, substituted aryl, unsubstituted aryl, substituted heterocyclic, unsubstituted heterocyclic, substituted aryl$(C_1-C_3)$alkyl, unsubstituted aryl$(C_1-C_3)$alkyl, substituted heterocyclic$(C_1-C_3)$alkyl and unsubstituted heterocyclic$(C_1-C_3)$alkyl;

each $R^a$ is independently selected from the group consisting of —H, —$CH_3$, —$(CH_2)_3$—NH—$C(NH_2)(=NH)$, —$CH_2C(=O)NH_2$, —$CH_2COOH$, —$CH_2SH$, —$(CH_2)_2C(=O)$—$NH_2$, —$(CH_2)_2COOH$, —$CH_2$-(2-imidazolyl), —$CH(CH_3)$—$CH_2$—$CH_3$, —$CH_2CH(CH_3)_2$, —$(CH_2)_4$—$NH_2$, —$(CH_2)_2$—S—$CH_3$, phenyl, $CH_2$-phenyl, —$CH_2$—OH, —$CH(OH)$—$CH_3$, —$CH_2$-(3-indolyl), —$CH_2$-(4-hydroxyphenyl), —$CH(CH_3)_2$ and —$CH_2$—$CH_3$; and includes compounds wherein $R^a$ and $R^1$ combine to form a 5-, 6- or 7-membered heterocyclic ring;

each $R^1$ is independently selected from the group consisting of —H, —$(C_1-C_6)$perfluoroalkyl, unsubstituted aryl, substituted aryl, substituted heterocyclic, unsubstituted heterocyclic, —$CO_2R^5$, —$C(=O)NR^4_2$, —$CR^4R^6R^7$, —$C(=NH)$—$NR^4_2$ and a monovalent peptidyl moiety with a molecular weight of less than 1000; provided that when y is 0 and $R^1$ is —$CO_2R^5$, $R^5$ is not —H;

each $R^2$ is independently selected from the group consisting of —H, —$(C_1-C_6)$alkyl, and aryl$(C_1-C_3)$alkyl, wherein —$R^2$ and -$(M)_y$-$R^1$ may optionally be linked covalently to form a 5-, 6- or 7-membered substituted or unsubstituted heterocycle;

$R^3$ is independently selected from —$(C_1-C_6)$alkyl;

each $R^4$ is independently selected from the group consisting of —H, and —$(C_1-C_6)$alkyl;

wherein:
when $R^4$ and $R^1$ are bonded to the same nitrogen atom, $R^1$ and $R^4$ may combine to form a heterocycle; and
when two $R^4$ groups are geminally bonded to the same nitrogen, the two $R^4$ groups may combine to form a heterocycle;

each $R^5$ is independently selected from the group consisting of —H, —$(C_1-C_6)$alkyl and —$(C_1-C_6)$acyl;

each $R^6$ is independently selected from the group consisting of —H, —$(C_1-C_6)$alkyl, —$CO_2R^5$, —$C(=O)R^7$, —$OR^5$, —$SR^4$, —$(C_1-C_3)$alkoxy, —$(C_1-C_3)$alkylthio, guanidino, —$NR^4_2$, phenyl, substituted phenyl, heterocyclic, substituted heterocyclic and halogen;

each $R^7$ is independently selected from the group consisting of —H, halogen, —$(C_1-C_6)$alkyl, —$NR^4_2$ and heterocycles containing two nitrogen atoms; and wherein the substituents for the substituted aryl and substituted heterocyclic groups comprising or included within Ar, R, $R^1$, $R^a$, $R^6$ and $R^7$, are independently selected from the group consisting of halogen, $(C_1-C_6)$alkyl, $(C_1-C_6)$alkoxy, —$NO_2$, —C≡N, —$CO_2R^5$, —$C(=O)O(C_1-C_3)$alkyl, —OH, —$(C_2-C_6)$—OH, phosphonato, —$NR^4_2$, —$NHC(=O)(C_1-C_6)$alkyl, sulfamyl, carbamyl, —$OC(=O)(C_1-C_3)$alkyl, —$O(C_2-C_6)$—$N((C_1-C_6)$alkyl$)_2$ and —$CF_3$;

provided
(1) when $R^1$ is a monovalent peptidyl moiety of molecular weight less than 1000 and V is —$C(=O)$—, —$C(=S)$—, —$S(=O)$— or —$SO_2$—, and b is 0;
then said peptidyl moiety is coupled to M through the peptide's amino terminus or through a sidechain amino group to form an amide, thioamide, sulfinamide or sulfonamide respectively;

(2) when $R^1$ is a monovalent peptidyl moiety of molecular weight less than 1000 and V is —$C(=O)NR^3$—, —$SO_2NR^3$—, or —$NR^4$—, and b is 0,
then said peptidyl moiety is coupled to M through the peptide's carboxy terminus or through a sidechain carboxyl group to form an imide, sulfonimide, or carboxamide respectively; and (3) when $R^1$ is a monovalent peptidyl moiety of molecular weight less than 1000 and W is —S— or —O—, and d is 0,
then said peptidyl moiety is coupled to M through the peptide's carboxy terminus or through a sidechain carboxyl group to form a carbothioic acid ester or the carboxylic ester respectively;

or a salt of such a compound. Compounds of this structure are preferred of the formula III:

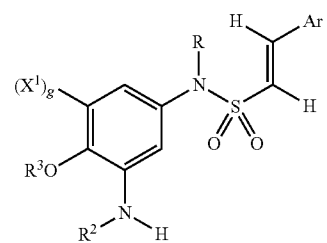

wherein:
Ar, $X^1$, R, $R^2$, $R^3$ and g are defined as in claim 1;
or a salt of such a compound. Compounds of formula III are further preferred which have the formula IIIa:

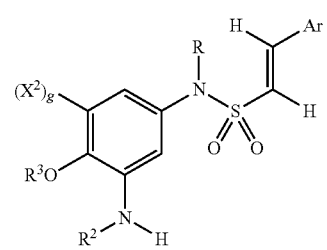

wherein:
Ar, R, $R^2$, $R^3$ and g are defined as in claim 2;
$X^2$ is selected from the group consisting of $NO_2$ and —$NH_2$, optionally protected with a chemical protecting group;
or a salt of such a compound Compounds of formula IIIa are further preferred which have the formula IIIa':

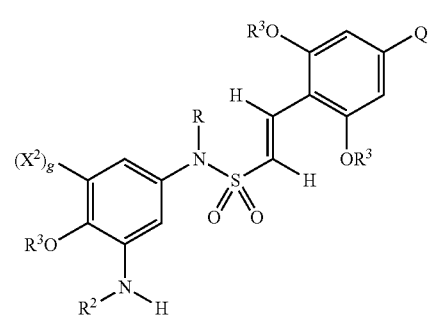

wherein:
$X^2$, R, $R^2$ and g are defined as in claim 3;
each $R^3$ is independently selected from —$(C_1-C_6)$alkyl; and
Q is selected from the group consisting of —H, —$(C_1-C_6)$alkoxy, halogen, —$(C_1-C_6)$alkyl and —$NR^4_2$;
or a salt of such a compound. Particularly, wherein Q is —$(C_1-C_6)$alkoxy-or- wherein Q is —$OCH_3$. Compounds are further preferred wherein $R^3$ is —$CH_3$; or a salt of such a compound. An exemplary compound is (E)-2,4,6-trimethoxystyryl-4-methoxy-3-aminophenylsulfonamide.

Exemplary cytotoxic drugs employed as elements of the activated prodrug and/or drug delivery entities of the present invention include (E)-2,4,6-trimethoxystyryl-4-methoxy-3-aminobenzylsulfone (ON 01500); (E)-5-((2,4,6-trimethoxystyryl-sulfonyl)methyl)-2-methoxyphenol (ON 013100); and, (E)-2,4,6-trimethoxystyryl-4-methoxy-3-aminophenylsulfonamide (ON 24160), for example. See, Examples I-III.

Activated cytotoxic prodrug compounds for attachment to targeting molecules are described herein. Compounds of the present invention generally comprise an activator moiety, a spacer linker, a self-immolative linker, and a cytotoxic drug. Although embodiments of the present invention are referred to herein as "activated", the entities are in fact pharmacologically inactive prodrugs "activated" by means of the presence of the activator moiety for attachment to a targeting molecule. Humanized antibodies, for example, are preferred targeting molecules. Cells which exhibit tumor specific surface antigens are preferred target cells for cytotoxic prodrug compounds of the present invention attached to targeting molecules.

The cytotoxic drug compounds described herein are nanomolar cytotoxins against a broad spectrum of cancer cell lines, for example. The prodrugs described herein contain a diverse array of self-immolative (i.e. self-destructing) chemical linkers that can be covalently attached to either amino or thiol (derived from reduced disulfide bonds) groups found on targeting molecules, monoclonal antibodies, for example. Resulting cytotoxic prodrug compounds attached to targeting molecules described herein have excellent plasma stability, efficient release of the cytotoxic payload inside targeted cancer cells, the ability to avoid antibody-drug conjugate (ADC) aggregation, non-existent immunogenicity properties, and a good maintenance of binding affinity.

The cytotoxic drug element of compounds of the present invention remain substantially inactive pharmacologically until a release of the drug, per se, in vivo, for example, by means of the severance at the site of the self-immolative linker. Drug release is important. Labile linker, e.g., acid-labile or enzyme labile linkers are employed in the drug delivery entities described herein.

Activated cytotoxic compounds are provided suitable for attachment to targeting molecules to yield drug delivery entities for specifically delivering the cytotoxic compound to abnormal cells and tissues for the treatment of mammalian disease conditions including but not limited to cell proliferative disorders, infectious disease, and immune-system disorders.

Activated cytotoxic compounds of the present invention are fundamentally prodrugs of the parent cytotoxic compounds that are substantially pharmacologically inactive in the "activated" structures described herein. The activated cytotoxic compounds, although they remain prodrugs until released, are transformed into specific drug-delivery vehicles when attached, preferably covalently, to targeting molecules. The activated cytotoxic compounds attached to targeting molecules are the resulting drug-delivery entities for administration to a mammal in need of treatment of a disease conditions including but not limited to cell proliferative disorders, infectious disease, and immune-system disorders.

Activated cytotoxic compounds of the present invention, for attachment to targeting molecules, comprise an activator, a spacer linker, a self-immolative linker, and a cytotoxin compound.

The configuration of activated cytotoxic compounds of the present invention may be generally represented spatially as follows:
activator—spacer linker—self-immolative linker—cytotoxin Activator Groups Primary activator groups are generally covalently attached to the spacer linker as follows:

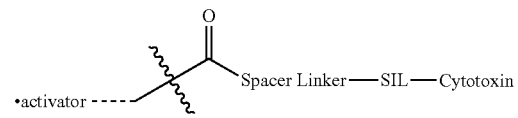

Activator groups for employment in activated cytotoxic compounds and entities of the present invention include but are not limited to the following example structures which attach to the spacer linker carboxyl group to yield activated cytotoxic compounds for covalent linkage to amino groups of targeting molecules, antibodies, for example.

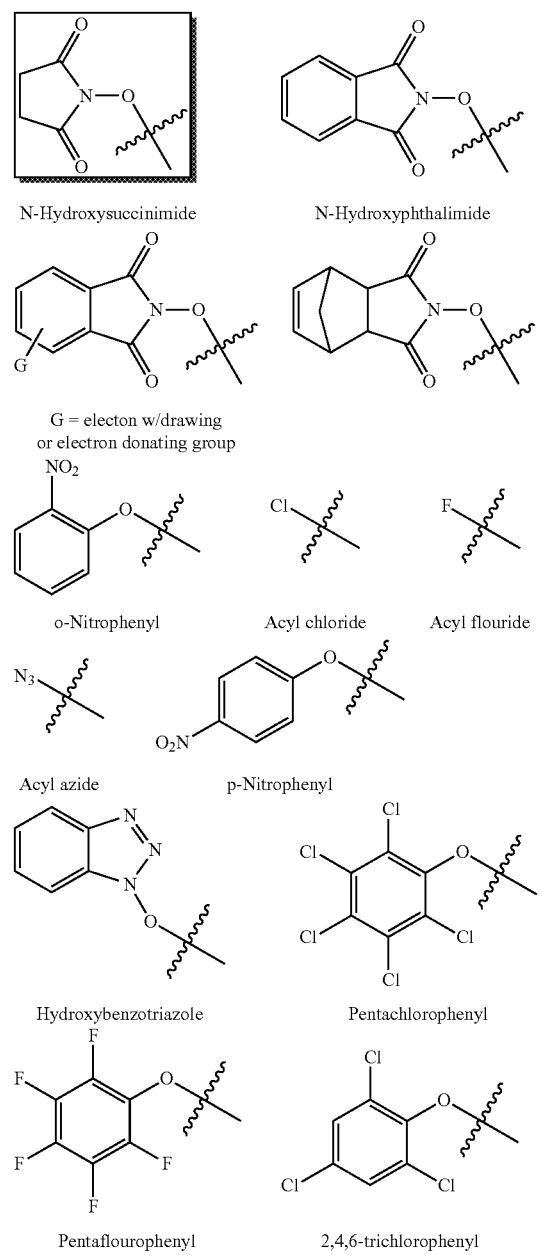

Spacer Linkers

The spacer linker examples shown below represent bifunctional organic compounds of varying length and size that simply provide attachment of the self-immolative (self-destructing) linker to the antibody, protein, or peptide surface. The bonds comprised of the spacer linker and antibody, peptide, or protein and of the spacer linker-(self-immolative linker) are stable in the blood compartment. The bond between the spacer linker and the self-immolative linker, by necessity, is designed to yield to acidic or enzymatic hydrolysis from within the target tissue.

Spacer linkers generally consist of symmetric and dissymmetric dicarboxylic acids, whereby one carboxyl group is covalently bound to an amino group of a targeting molecule, and the remaining carboxyl group is covalently bound to an amino or hydroxyl group of a self-immolative linker. A few representative examples are shown:

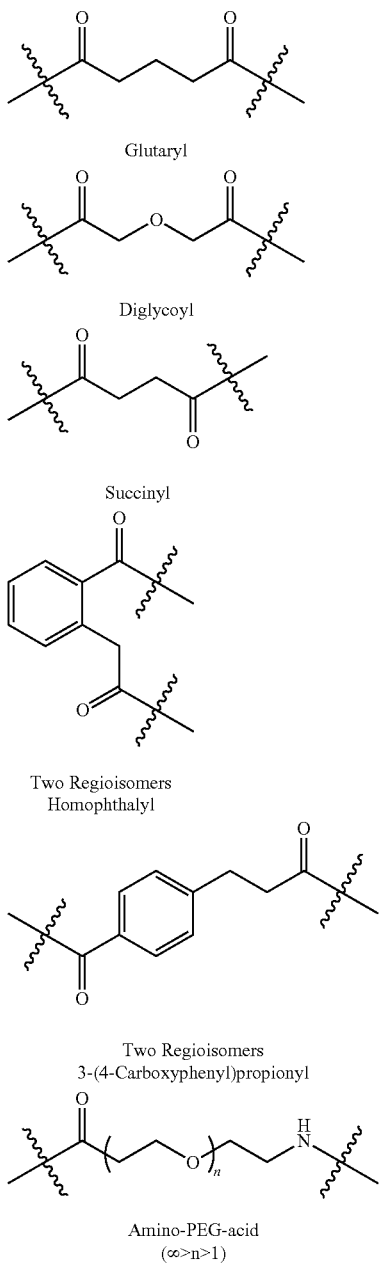

Heterobifunctional Spacer Linkers

Amine- and sulfhydryl-reactive heterobifunctional crosslinkers are widely used for covalent conjugation of targeting molecules and cytoxic payloads, and are commercially available in a variety of forms. These reagents (linkers) can be loosely categorized in the following way:
1) Amine-reactive end of the heterobifunctional crosslinker is used to capture lysine residues (or alternative 1° and/or 2° amino groups) on a targeting molecule; while the sulfhydryl-reactive (or thiol-reactive) function captures the drug (or prodrug) molecule that possesses a free thiol group. Examples include, but are not limited to the following:

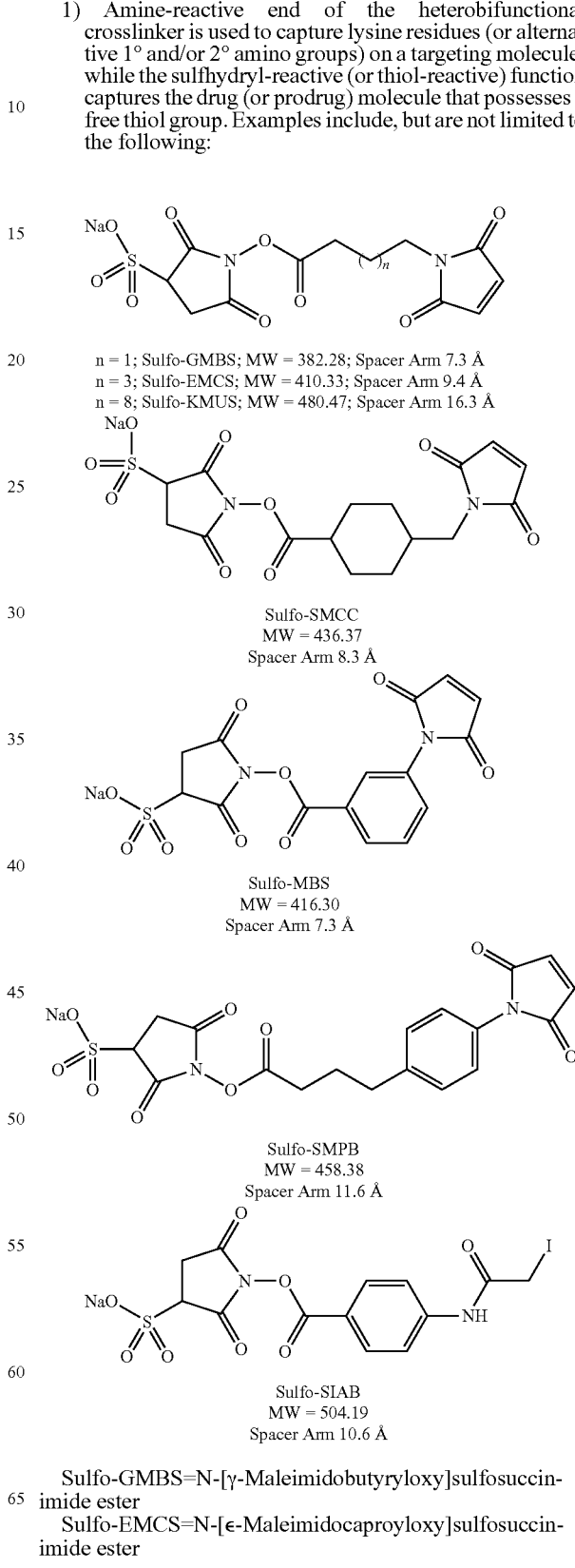

Sulfo-GMBS=N-[γ-Maleimidobutyryloxy]sulfosuccinimide ester
Sulfo-EMCS=N-[ε-Maleimidocaproyloxy]sulfosuccinimide ester Sulfo-KMUS=N-[κ-Maleimidoundecanoyloxy]sulfosuccinimide ester
Sulfo-SMCC=Sulfosuccinimidyl-4-[N-maleimidomethyl]cyclohexane-1-carboxylate
Sulfo-MBS=m-Malemidobenzoyl-N-hydroxysulfosuccinimide ester
Sulfo-SMPB=Sulfosuccinimidyl 4-[p-maleimidophenyl]butyrate
Sulfo-SIAB=N-Sulfosuccinimidyl[4-iodoacetyl]aminobenzoate 2) Amine-reactive end of the heterobifunctional crosslinker is used to capture a drug or prodrug molecule that possesses a 1° and/or 2° amino group; while the sulfhydryl-reactive function captures either a native thiol group from a targeting molecule (e.g. thiol groups that are generated by partial reduction of disulfide bridges found on most antibodies), or a targeting group that is installed onto the surface of a targeting molecule. Examples include, but are not limited to the following:

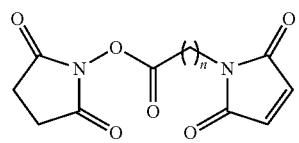

n = 1; AMAS; MW = 252.18; Spacer Arm 4.4 Å
n = 2; BMPS; MW = 266.21; Spacer Arm 5.9 Å
n = 3; GMBS; MW = 280.23; Spacer Arm 7.3 Å
n = 5; GMBS; MW = 308.29; Spacer Arm 9.4 Å

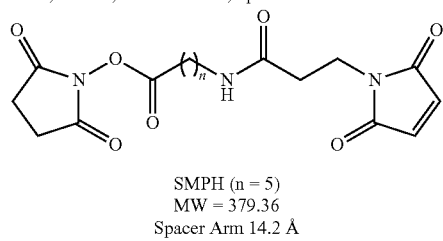

SMPH (n = 5)
MW = 379.36
Spacer Arm 14.2 Å

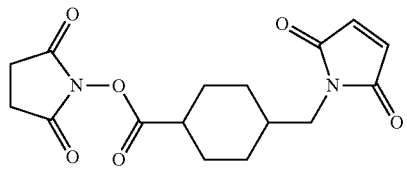

SMCC
MW = 334.32
Spacer Arm 8.3 Å

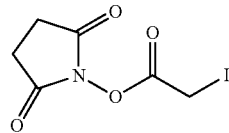

SIA
MW = 283.02
Spacer Arm 1.5 Å

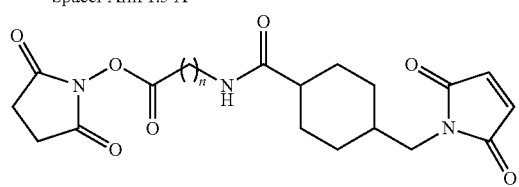

LC-SMCC (n = 5)
MW = 447.48
Spacer Arm 16.2 Å

-continued

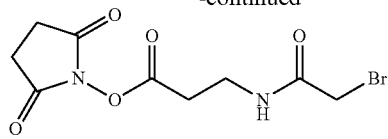

SBAP
MW = 307.10
Spacer Arm 6.2 Å

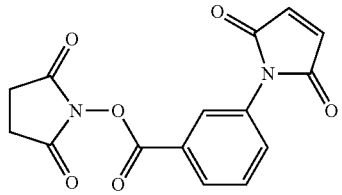

MBS
MW = 314.25
Spacer Arm 7.3 Å

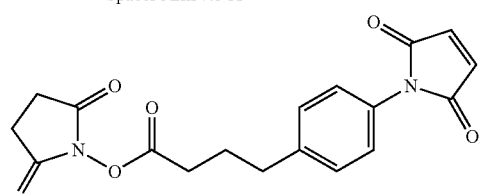

SMPB
MW = 356.33
Spacer Arm 11.6 Å

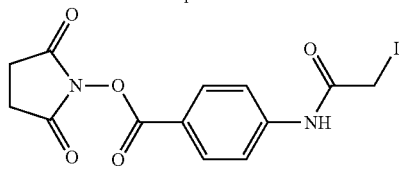

SIAB
MW = 402.14
Spacer Arm 10.6 Å

AMAS=N-[α-Maleimidoacetoxy]succinimide ester
BMPS=N-[β-Maleimidopropyloxy]succinimide ester
GMBS=N-[γ-Maleimidobutyryloxy]succinimide ester
EMCS=N-[ε-Maleimidocaproyloxy]succimimide ester
SMPH=Succinimidyl-6-[β-maleimidopropionamido]hexanoate
SMCC Succinimidyl-4-[N-maleimidomethyl]cyclohexane-1-carboxylate
LC-SMCC=Succinimidyl-4-[N-maleimidomethyl]cyclohexane-1-carboxy-[6-amidocaproate]
MBS=m-Malemidobenzoyl-N-hydroxysuccinimide ester
SMPB=Succinimidyl 4-[p-maleimidophenyl]butyrate
SIAB=N-Succinimidyl[4-iodoacetyl]aminobenzoate
SIA=N-Succinimidyl iodoacetate
SBAP=Succinimidyl 3-[bromoacetamido]propionate 3) Amine-reactive end of the heterobifunctional crosslinker is used to capture amino groups found on the drug (or prodrug) molecule or on the targeting molecule, while the sulfhydryl-reactive group captures the corresponding thiol group to form a disulfide bond. Also, the sulfhydryl-reactive group on this class of heterobifunctional spacer linkers can be mildly reduced (e.g DTT or glutathione) to reveal a thiol group that subsequently can conjugate to a thiol-reactive maleimido group of a prodrug. Examples include, but are not limited to the following:

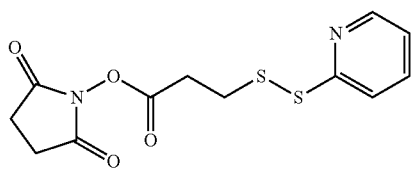

SPDP
MW = 312.37
Spacer Arm 6.8 Å

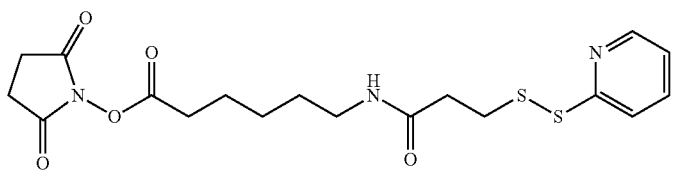

LC-SPDP
MW = 425.52
Spacer Arm 15.7 Å

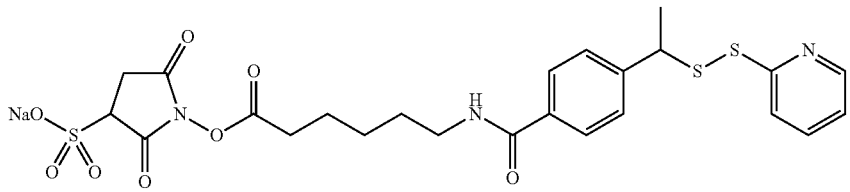

Sulfo-LC-SMPT
MW = 603.67
Spacer Arm 20.0 Å

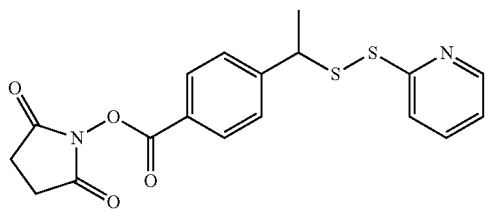

SMPT
MW = 388.46
Spacer Arm 11.2 Å

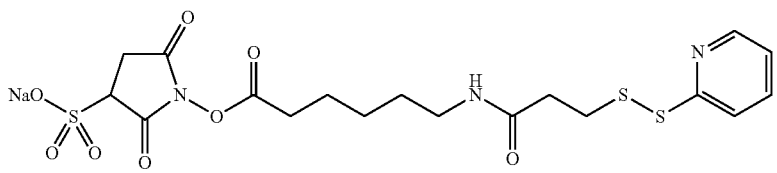

Sulfo-LC-SPDP
MW = 527.57
Spacer Arm 15.7 Å

SPDP=N-Succinimidyl 3-(2-pyridyldithio)propionate
LC-SPDP=Succinimidyl 6-(3'-[2-pyridyldithio]propionamido)hexanoate
Sulfo-LC-SPDP=Sulfosuccinimidyl 6-(3'-[2-pyridyldithio]propionamido)hexanoate
SMPT=4-Succinimidyloxycarbonyl-α-methyl-α-[2-pyridyldithio]toluene
Sulfo-LC-SMPT=4-Sulfosuccinimidyl 6[-α-methyl-α-(2-pyridyldithio)toluamido]hexanoate Alternatively, it may be advantageous to incorporate polyethylene glycol (PEG) chains of varying length between the amine- and sulfhydryl-reactive groups of heterobifunctional spacer linkers, since PEG is known to increase aqueous solubility and the serum stability half-lives of, for example, immunoconjugate molecules, without undesired antigenicity from the PEG chain itself. A few representative examples include, but are not limited to the following:

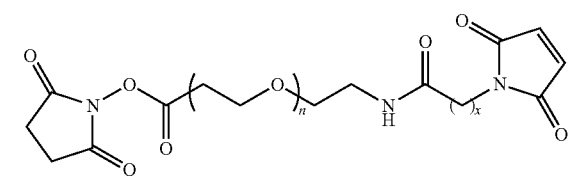

n = 1 or greater integer
x = 1 or greater integer

PEG amino acid bearing NHS
and maleimido groups

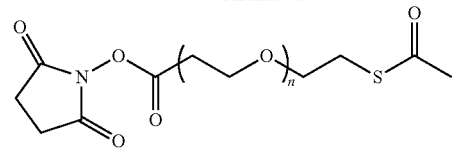

n = 1 or greater integer

PEG chains bearing NHS
and masked sulfhydryl groups

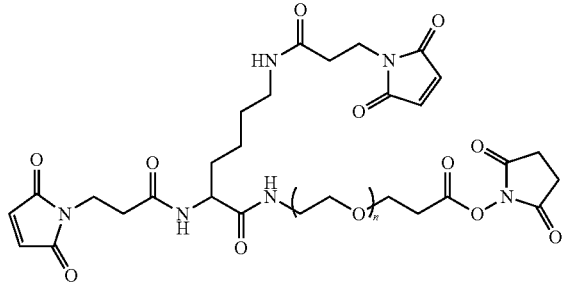

n = 1 or greater integer

PEG amino acid bearing NHS
and maleimido groups with branching

Self-Immolative Linkers

The self-immolative linker examples represent bifunctional organic compounds with the capability of being completely eliminated (i.e. traceless) from the cytotoxin after either one or both of the following events:

1) Hydrolysis of the covalent bond between the spacer linker and the self-immolative linker, and/or
2) Hydrolysis of the covalent bond between the self-immolative linker and the cytotoxin The self-immolative linkers are covalently bonded to a carboxy or amino group of a spacer linker on the left of the structures shown below and a hydroxy amino groups of cytotoxin on the right.

para-Aminobenzyl Alcohol

Ethylenediamines
(e.g. R = H or CH$_3$;
R' = H or CH$_3$)

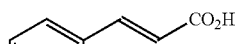

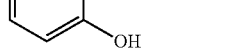

3,3-Dimethyl-4-hydroxy-butyric Acid

4-Aminobutyric Acid
γ-Aminobutyric Acid (GABA)

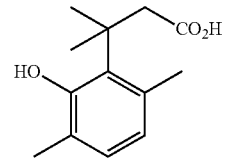

"Trimethyl Lock"

2-Hydroxycinnamic Acid

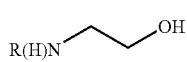

Ethanolamines
(e.g. R = H or CH$_3$)

Preparation

EXAMPLE IV illustrates the preparation of an embodiment of an activated cytotoxic compound (ON 12013100) suitable for attachment to a targeting molecule. EXAMPLE V illustrates the attachment of 12013100, for example, to an example targeting molecule.

Figure 1B:
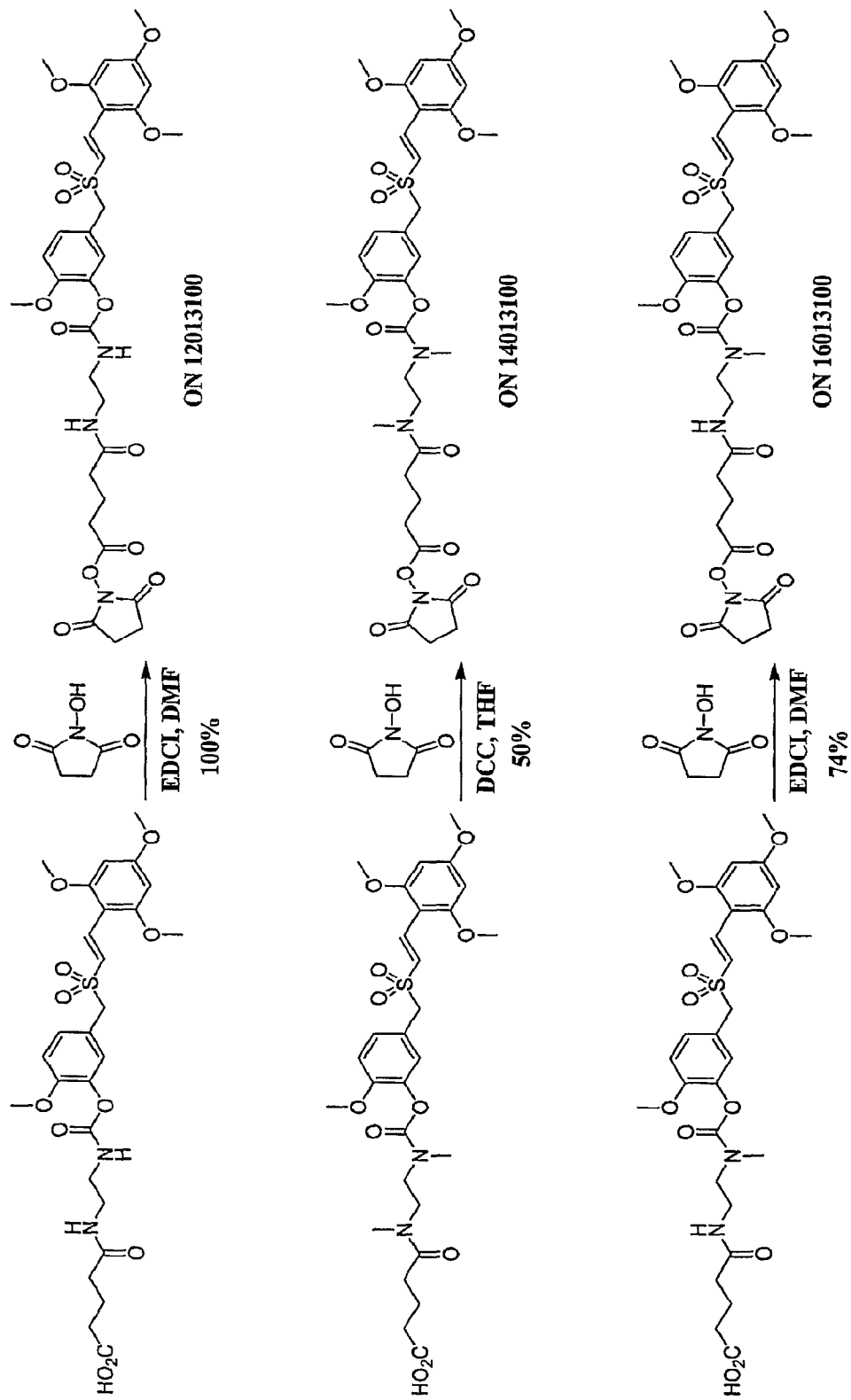

General Preparation of Prodrugs ON 12013100, ON 14013100, and ON 16013100 FIGS. 1A and 1B illustrate example synthetic schemes for activated cytotoxic compounds of the present invention (ON 12013100, ON 14013100, and ON 16013100), each of which is suitable for attachment to a targeting molecule. See, Example VI.

Example activated cytotoxic (prodrug) compounds of the present invention (activated for attachment to targeting molecules to create drug delivery entities). NHS=N-Hydroxysuccinimidyl; GABA=gamma-Aminobutyric Acid; and PABA=para-Aminobenzyl Alcohol.

Example Prodrugs of ON 01500

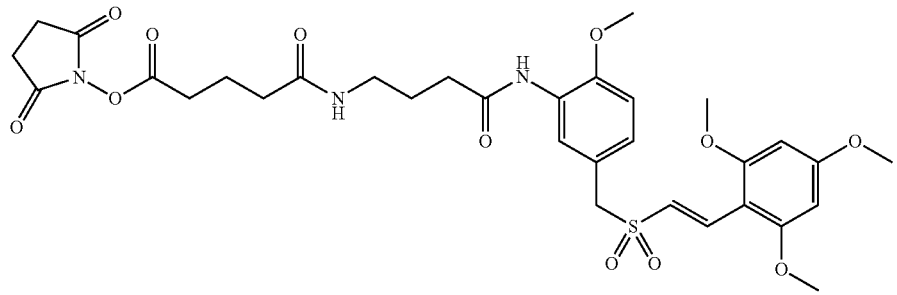

NHS-glutaryl-GABA-(ON 01500)

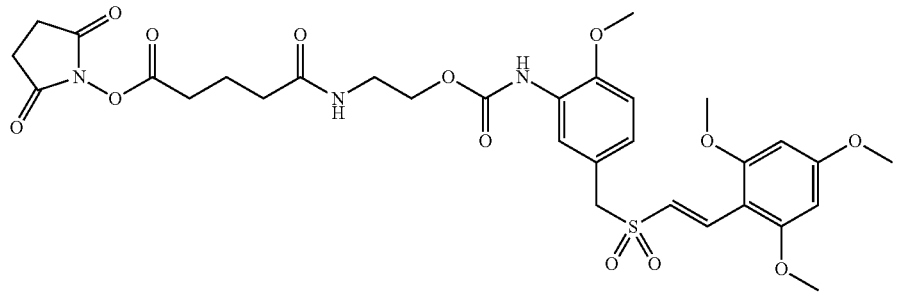

NHS-glutaryl-ethanolamine-(ON 01500)

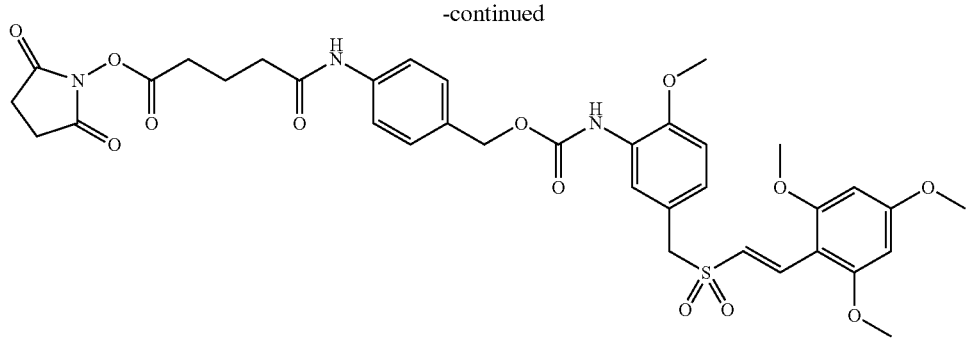
NHS-glutaryl-PABA-(ON 01500)
Example Prodrugs of ON 013100
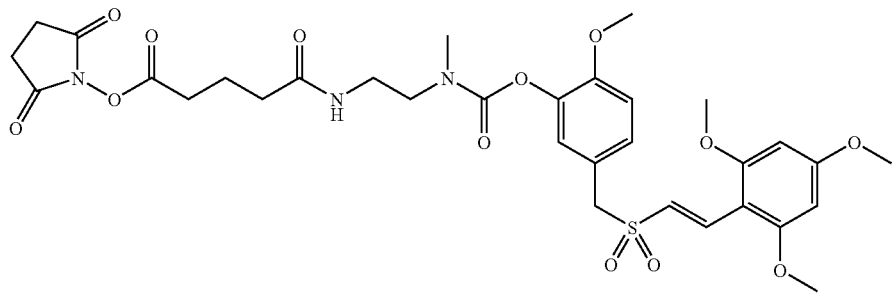
NHS-glutaryl-N-methylethylenediamine- (ON 013100)
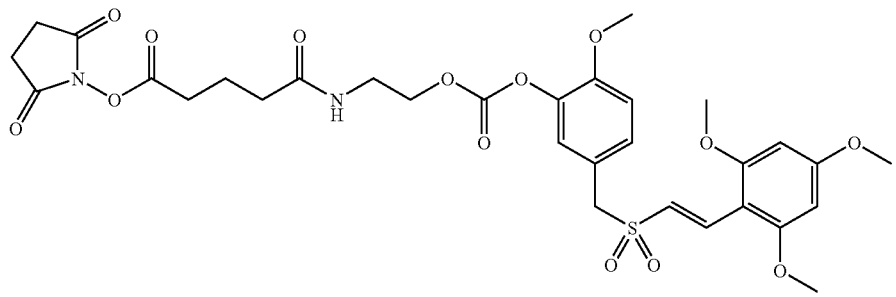
NHS-glutaryl-ethanolamine-(ON 013100)
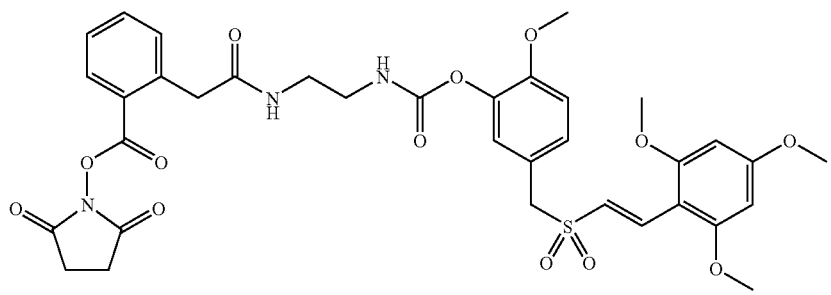
NHS-homophthalyl-ethylenediamine-(ON 013100)

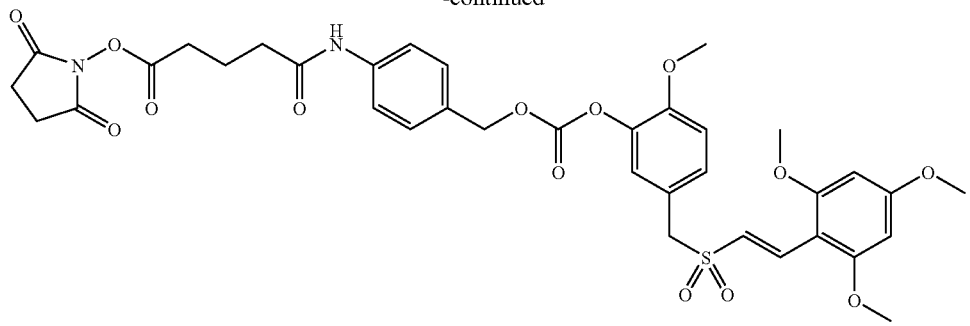

NHS-glutaryl-PABA-(ON 013100)

Example Ethylenediamine-Containing Prodrugs of ON 013100

N-methylation of amide and/or carbamate linkages (shown in ovals) attenuates the proteolytic release of the cytotoxic drug in vivo while increasing plasma stability of the cytotoxic compound attached to a targeting molecule.

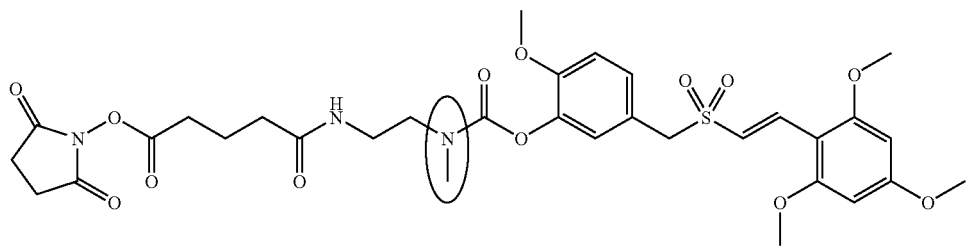

NHS-Glutaryl-N'-methylethylenediamine carbamate of ON 013100 (ON 16013100)

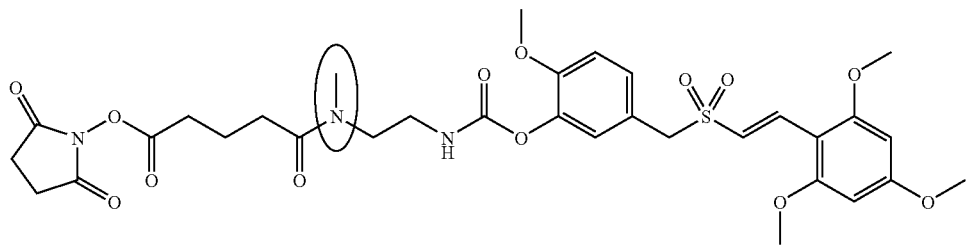

NHS-Glutaryl-N-methylethylenediamine carbamate of ON 013100

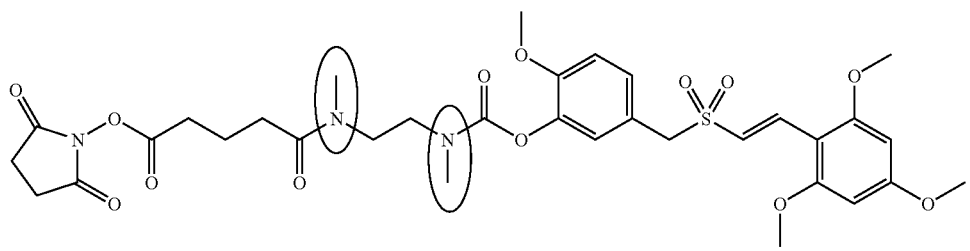

NHS-Glutaryl-N,N'-dimethylethylenediamine carbamate of ON 013100 (ON 14013100)

Example Prodrugs of ON 24160

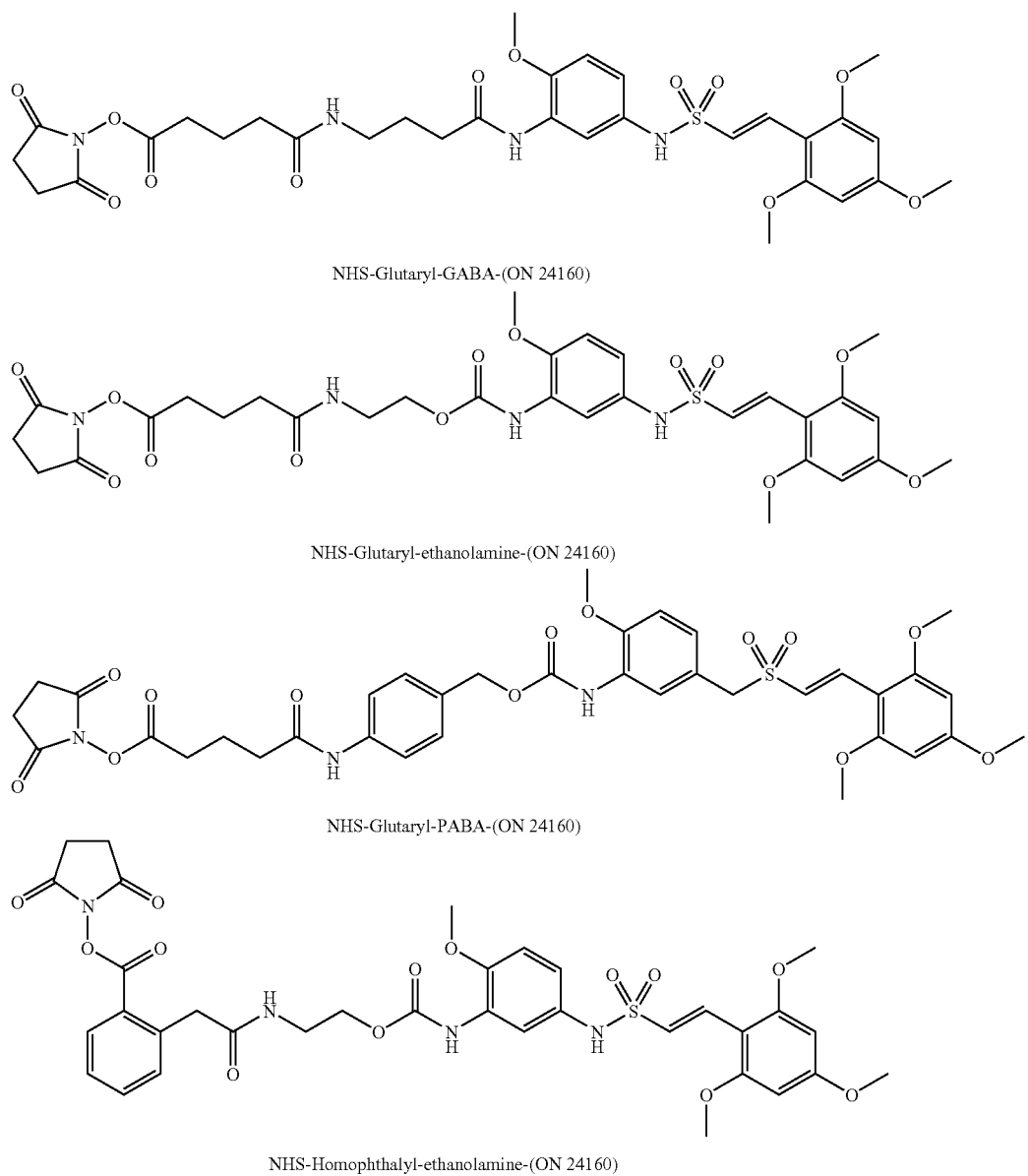

NHS-Glutaryl-GABA-(ON 24160)

NHS-Glutaryl-ethanolamine-(ON 24160)

NHS-Glutaryl-PABA-(ON 24160)

NHS-Homophthalyl-ethanolamine-(ON 24160)

Attachment to Targeting Molecules

Covalent bonds are preferred for attachment. Activated cytotoxic prodrug compounds for attachment to targeting molecules described herein are preferably covalently linked to internalizing monoclonal antibodies (e.g. Trastuzumab and an anti-CD138 antibody derived from a commercial available hybridoma) that have therapeutic relevance to patients afflicted with HER2 positive breast cancer and CD138 positive multiple myelomas, respectively. See, e.g., EXAMPLE V.

Conjugation

Figure 2:
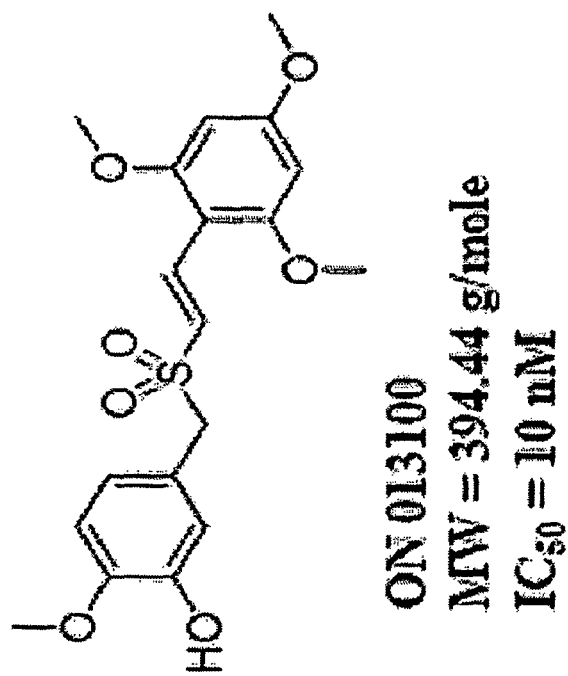
FIG. 2 illustrates example structures of cytotoxic compounds for employment in the drug delivery entities of the present invention.
Figure 2:
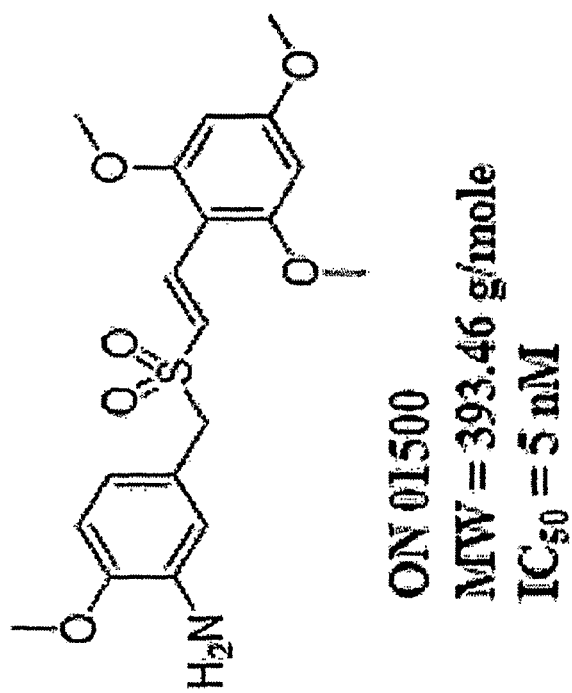

The cytotoxic compounds, for example, are benzyl styryl sulfones having molecular weights below 500 which contain at least one functional group that is suitable for conjugation. Structures of example compounds are shown in FIG. 2. Biological activity for these compounds is described infra.

Strategically, there are several methods by which these compounds can be conjugated to targeting proteins, monoclonal antibodies, for example. Either the ε-amino groups of lysine sidechains or the thiol groups generated after partial reduction of disulfide bridges that are concentrated at or near the hinge region can be targeted for the attachment of the prodrug. Additionally, there exist reagents and methodologies for attaching short molecular sidechains that contain masked thiol groups to lysine residues. Therefore, prodrugs must be designed that contain either amine- or thiol-reactive functional groups. Typically, these functions are introduced during the final step of the prodrug synthesis. Ideally, linkers that connect the cytotoxic payload and the monoclonal antibody must exhibit excellent plasma stability, yet must relinquish to either enzymatic or chemical (i.e. acidic hydrolysis) degradation within the tumor cell. Numerous self-immolative linker molecules have been described in the literature are commercially available. Amsberry, K. L., and Borchardt, R. T., *The Lactonization Of 2'-Hydroxydydrocinnamic Acid*

*Amides: A Potential Prodrug For Amines*, J. Org. Chem 55(23):5867-5877 (1990); Dubowchik, G. M., et al., *Efficient Mitocycin C Coupling with Stable p-Nitropheny-Benzy Carbonates Using N-Hydroxybenzotriazole as a Catalytic Additive*, Tetrahedron Letters, 30(30):5261-5264 (1997); Rodrigues, M. L., et al., *Synthesis And Beta-Lactamase-Mediated Activation Of A Cephalosporin-Taxol Prodrug*, Chem Biol. 2(4):223-7 (1995); Shabat D., et al., *Multiple Event Activation Of A Generic Prodrug Trigger By Antibody Catlaysis*, Proc Natl Acad Sci USA 96(12): 6925-30 (1999); Shabat D., et al., *In Vivo Activity In A Catalytic Antibody-Prodrug System: Antibody Catalyzed Etoposide Prodrug Activation For Selective Chemotherapy*, Proc Natl Acad Sci USA 98(13): 7528-33 (2001).

Figure 3:
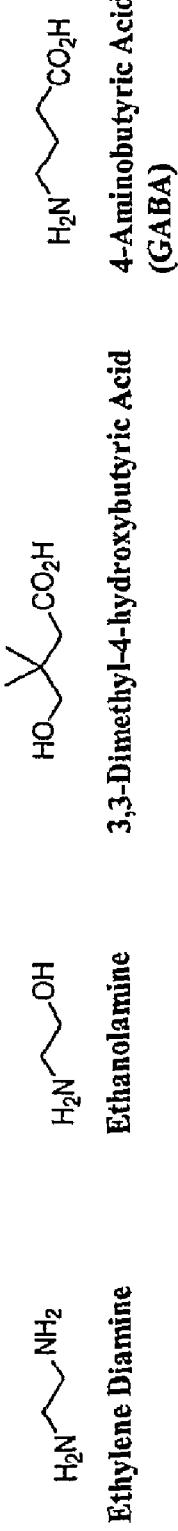
FIG. 3 dispays example self-immolative linker structures for employment as elements of the activated cytotoxic compounds of the present invention.
Figure 3:
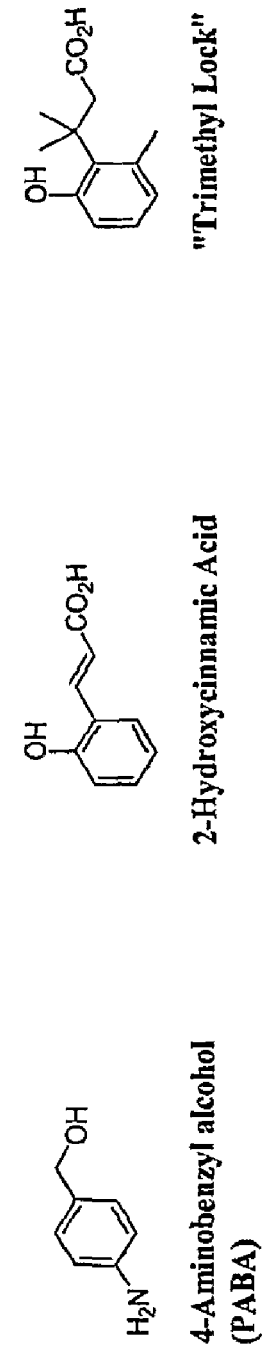

Several representative examples of existing self-immolative linkers are represented in FIG. 3.

Several proprietary prodrug molecules have been synthesized via routine synthetic methodologies, and from commercially and readily available reagents. Initial attempts to conjugate prodrugs to monoclonal antibodies, however, continued to resulted in highly aggregated immunoconjugate products. However, the conjugation protocols have been modified in a number of ways to avoid unwanted aggregation phenomena. Finally, prodrug ON 14013100 (an NHS-activated prodrug of ON 013100) containing a tandem variable length spacer and self-immolative linker system was synthesized from ON 013100 ((E)-5-((2,4,6-trimethoxystyrylsulfonyl)methyl)-2-methoxyphenol) and inexpensive commercial reagents using an efficient chemical process, which is outlined in Scheme 1.

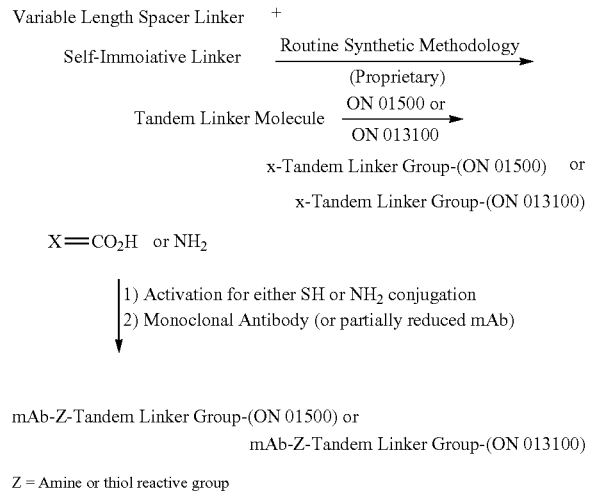

Figure 4:
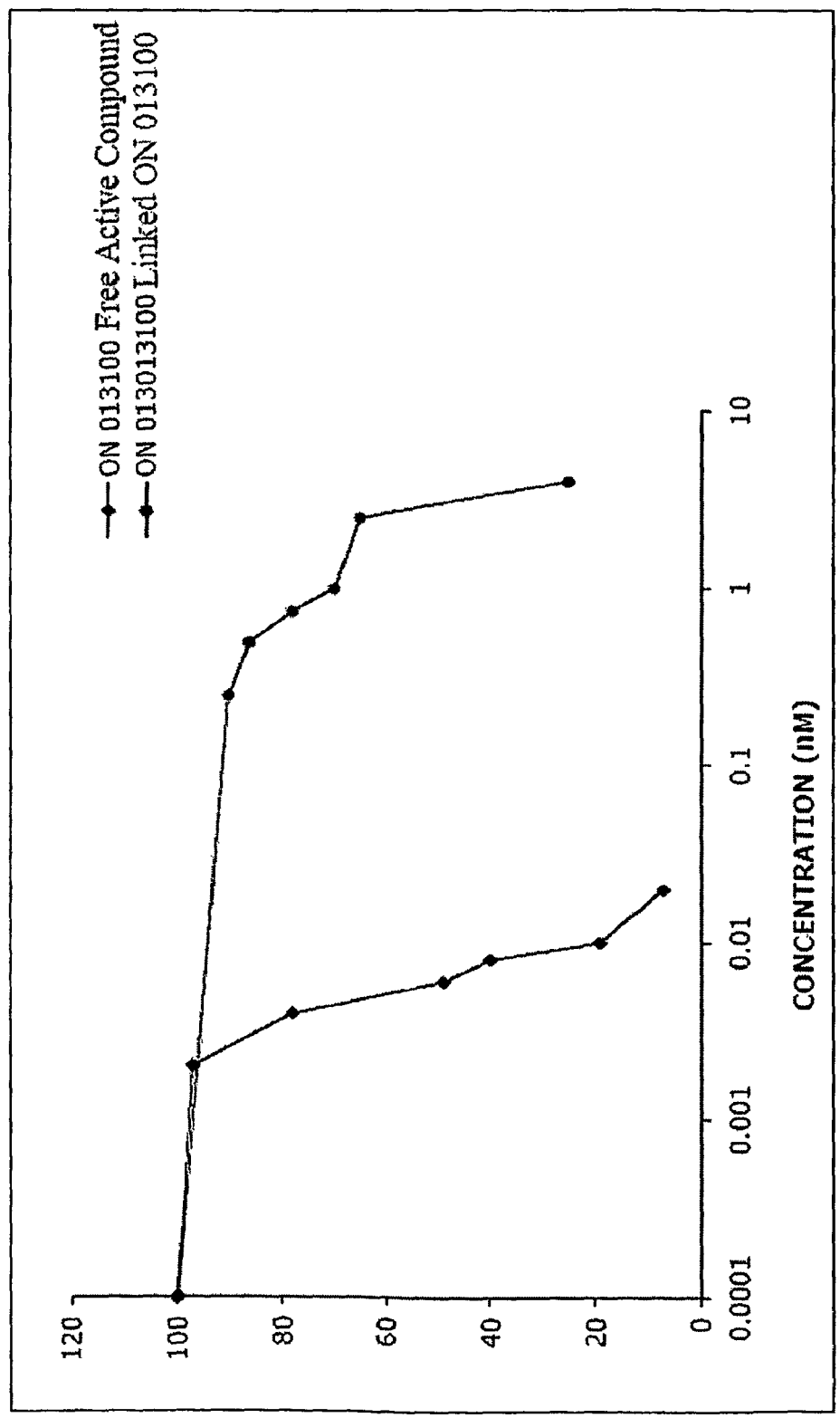
FIG. 4 illustrates the results of a dose response assay comparing a cytotxic compound (ON 013100) to its linked version (ON 013013100).

The penultimate precursor to compound ON 14013100 (an NHS-activated prodrug of ON 013100)—ON 13013100—lacks the activating group for conjugation to mAbs, and served as a suitable candidate to test for plasma stability. Compound ON 13013100 exhibits excellent stability when exposed to the sera of three mammalian species (murine, fetal bovine, and human) at 37° C. for 24 hours. Also, when compound ON 1301300 was screened in a dose response assay using 22RV1 prostate carcinoma cells, the activity of the prodrug is significantly reduced ($IC_{50}$=10 nM for ON 013100 versus and $IC_{50}$=2-3 µM for ON 13013100), which is consistent and desirable when designing a prodrug. See, FIG. 4 which illustrates a dose response assay comparing ON 013100 to its linked version, ON 013013100. 22RV1 cells were treated with various concentrations of ON 013100 and its linked version ON 013100. The linked version had greatly reduced cell killing activity. Finally, a covalent non-aggregating conjugate consisting of ON 14013100 (an NHS-activated prodrug of ON 013100) and Trastuzumab showed increased activity and selectivity towards a HER2 overexpressing cell line (BT474) versus a cell line expressing basal level HER2 (DU145). Current synthetic work is now focusing towards optimizing a variety of parameters (i.e. spacer length and type, mAb conjugation method, etc.) associated with the current result. Future studies will involve the synthesis and evaluation of a diverse collection of ON 01500 and ON 013100 prodrugs with the ultimate goal of improving pharmacokinetics, blood compartment stability, and intratumoral accumulation and drug release. Infra; see, Examples.

Attaching Activated Cytotoxic Compounds to Targeting Molecules

Several methods are employed to attach prodrug molecules to monoclonal antibodies, for example, including (1) hydrazone linker (2) peptide linker, and (3) disulfide linker. The acid-cleavable hydrazone linker is used in Mylotarg®, which has been approved for treatment of acute myelogenous leukemia by the Food and Drug Administration. Generally, peptidic linkers such as, Gly-Phe-Leu-Gly and Valine-Citrulline, have exhibited greater circulation stability than hydrazone linkers when preparing immunoconjugates of doxorubicin and monomethylauristatin E. The disulfide linkers, which are cleaved by disulfide exchange with glutathione, take advantage of the higher concentration of glutathione in tumor cells as compared to normal cells. Immunoconjugates linked by disulfide linkers to a maytansine derivative, DM1, are currently in phase I and phase II clinical studies. See, e.g., EXAMPLE V.

Figure 5:
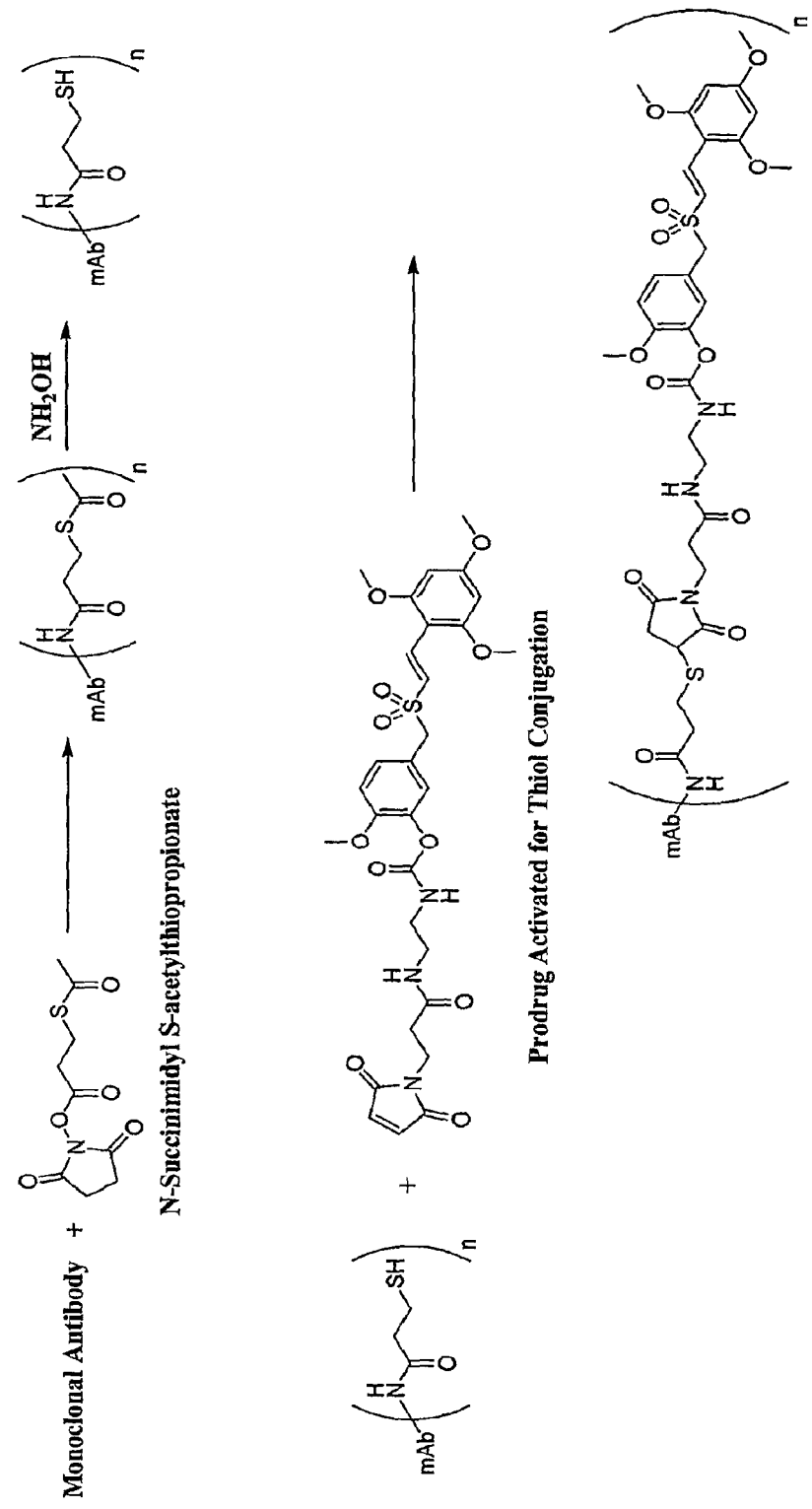
FIG. 5 shows an alternate approach to attaching antibodies to activated cytotoxic compounds of the present invention.

FIG. 5 illustrates an alternative approach to antibody conjugation (i.e. conversion of antibody sidechain lysine amino groups into thiols for reaction with prodrugs containing thiol reactive activating groups). One can partially reduce an antibody to convert native disulfide bridges into thiols. One could also activate the prodrug with a thiol tail and modify the antibody surface with thiol-reactive groups (e.g. maleimido groups).

Antibodies

Since the landmark discovery by Kohler and Milstein in 1975 that monoclonal antibodies could be generated via hybridoma technology, the medical field has witnessed a scientific revolution in how cancer and other challenging diseases are treated. This technological breakthrough has empowered the research community to create a seemingly endless supply of purified highly specific antibodies to apply to a wide array of medical applications, both in clinical and diagnostic settings. The field of oncology has benefited greatly from the discovery and development of antibody-based therapies, because several cell surface antigens have been identified that are over-expressed on certain cancer cell lines as compared to normal tissue.

The remarkable commercial and medical success of monoclonal antibodies has led to the exploration of variations of this therapeutic modality. One approach, which is particularly suited for anticancer therapy, involves Antibody-Drug Conjugates (ADCs), or immunoconjugates. We provide here novel chemical compounds that may be ideally suited as immunoconjugate payloads. Several mAbs are available that are directed to target antigens selectively expressed or over expressed on the surface of malignant cells and are known to be internalized into the cancer cell. These mAbs present excellent opportunities for the development of ADCs employing our anticancer compounds. Two examples of particular interest are Herceptin® (a commercial mAb used to treat HER2 (+) breast cancer) and the anti-CD138 mAb, B-B4 (a potential mAb treatment for multiple myeloma).

Thus far, the Food and Drug Administration has approved greater than 17 monoclonal antibody-based drugs—and hundreds are known to have entered the clinic for careful evaluation. Of the FDA-approved antibody-based products, eight are currently used to treat cancer. Five of the antibody products used to treat cancer are unmodified monoclonal antibodies (Table 1), while the remaining three products are covalently modified monoclonal antibodies armed with either toxins or radionuclides (Table 2).

TABLE 1

FDA-approved monoclonal antibody therapies for cancer

| Product | Company(s) | Description | Indication (Initial approval only) | Date |
|---|---|---|---|---|
| Rituxan | IDEC Pharmaceuticals (Biogen IDEC); Genentech; Roche | Pan-B chimeric mAb that targets CD20 antigen on B-cell surface | Relapsed or refractory low-grade or follicular CD20(+) B-cell non-Hodgkin's lymphoma | November 1997 |
| Herceptin | Genentech; Roche | Humanized mAb to epidermal growth factor receptor 2 (HER2/ErbB2) | HER2 over-expressing metastatic breast cancer; for use as $1^{st}$-line therapy in combnation with paclitaxel and as single agent $2^{nd}$- and $3^{rd}$-line therapy | September 1998 |
| Campath | Ilex Oncology: Berlex Laboratories (Schering AG) | Humanized mAb to CD52 antigen on T and B cells | B-cell chronic lymphocytic leukemia (B-CLL) in patients who have been treated w/ alkylating agents and who have failed fludarabine therapy | May 2001 |
| Avastin | Genentech | Humanized mAb to vascular Endothelial growth factor (VEGF) | Combination therapy with 5-Fluorouracil-based chemotherapy as a treatment for patients with $1^{st}$-line or previously untreated metastatic cancer of the colon or rectum | February 2004 |
| Erbitux | ImClone Systems: Bristol-Myers Squibb | IgG1 chimeric mAb to the epidermal growth factor receptor (EGFR) | Combination therapy with irinotecan for treating EGFR-expressing, metastasic colorectal cancer in patients who are refractory to irinotecan-based chemotherapy; also used as a single agent for treating patients with EGFR-expressing metastatic colorectal cancer who are intolerant to irinotecan-based chemotherapy | February 2004 |

TABLE 2

FDA-approved monoclonal antibody immunoconjugate therapies for cancer

| Product | Company(s) | Description | Indication (initial approval only) | Date |
|---|---|---|---|---|
| Mylotarg | Wyeth; Celltech Group | Humanized anti-CD33 mAb, conjugated w/ calicheamicin | Relapsed acute myeloid leukemia in CD33(+) patients who are 60 years of age or older and who are not candidates for cytotoxic chemotherapy | May 2000 |
| Zevalin | IDEC Pharmaceuticals (Biogen IDEC); Schering AG | Murine mAb that targets CD20 antigen on B cell surface, conjugated to Yttrium-90 isotope (used in conjunction w/ Rituxan | Radioimmunotherapy for treating low grade or follicular, relapsed or refractory, CD20(+), B-cell non-Hodgkin's lymphoma and Rituxan-refractory follicular NHL | February 2002 |
| Bexxar | Corixa (Coulter Pharma-Ceuticals); GlaxoSmithKline | Muring mAb to CD20 antigen on B-cells, conjugated to Iodine-131, used in conjunction w/ the non-Radioactive antibody | Patients w/ CD20(+) non-Hodgkin's lymphoma, with and without transformation, whose disease is refractory to Rituxan and and has relapsed following chemotherapy | June 2003 |

Breast Cancer

The current standard of care, Trastuzumab targets the antigen HER2/Neu, a highly validated target in breast cancer that is over-expressed in 20-30% of all breast cancers. Assuming a patient population of approximately 18,000-19,000 new patients per year in the US expressing this antigen, we believe that a significant portion of this population could benefit from the greater therapeutic index of a drug conjugate such as the one Onconova is developing. Furthermore, patients relapsing after Trastuzumab treatment could be candidates for a new antibody drug conjugate.

Many challenges exist confronting the development of immunoconjugates, for example. First and foremost is stability—immunoconjugates can degrade prior to being delivered to the target site. Chemical linkers that conjoin the antibody and cytotoxin must also show stability in plasma, yet be vulnerable to intracellular degradation once it reaches its target. Additionally, the conjugation sequence and loading stoichiometry used to prepare antibody-drug conjugates can alter the antigen binding characteristics or cause unwanted aggregation. Finally, the cytotoxin to be linked must have extremely high potency.

Multiple Myeloma

Multiple myeloma is the second most prevalent hematologic cancer after non-Hodgkin's lymphoma. The American Cancer Society estimates that about 15,000 new cases of multiple myeloma will be diagnosed in 2006. Multiple myeloma is a cancer of the plasma cells, resulting in the uncontrolled proliferation of a type of white blood cells called plasma cells. During development, genetic abnormalities can occur that yield malignant plasma cells. These malignant cells known as myeloid cells, tend to aggregate in the bone marrow and the hard outer layers of the bone. This aggregation behavior can lead to osteolytic lesions and pain, which in turn lead to fracture and the metabolic disorder.

Since myeloid cells are throughout the bone marrow, surgery and radiotherapy are not the most effective treatment options, leaving chemotherapy a more optimal treatment. Myeloid patients can survive for many years if these patients achieve a stable remission and undergo a number of lines of drug therapy. Onconova's drug conjugates are designed to specifically target the CD138 and CD38 antigens, both validated targets which are over-expressed in myeloid cancer cells. Because of the high volume of patients, and long usage duration of the chemotherapies, multiple myeloma potentially represents a highly attractive indication for new agents. Based on the number of new cases per year (broadly expressed antigen) and the current reimbursement for therapy, the market for drugs addressing multiple myeloma is estimated to be in excess of $400 million per year.

Cell Toxicity Data

Creation of effective immunoconjugates requires that the antibody be conjugated to a compound that is extremely potent in inducing cell-death in the targeted cells. This is due to the fact that only a small number of molecules can be attached per IgG molecule without interfering with antibody function. Chari, R. V., *Targeted Delivery Of Chemotherapeutics: Tumor-Activated Prodrug Therapy*, Adv. Drug Delivery Rev., 31: 89-104 (1998).

Two compounds were selected from our library of cytotoxic molecules for immunoconjugation since they both have $IC_{50}$ values in the low nanomolar range. Various tumor cell lines (ATCC) were treated for 96 hours in the presence of increasing concentrations of each compound and the total number of viable cells remaining was determined after 96 hours of exposure. The $IC_{50}$ value was determined to be the amount of drug required to inhibit the growth of each cell line 50% as compared to vehicle treated cells. The data in Table 3 shows that all the cell lines tested are sensitive to the cytotoxic effect of the compounds. ON 01500 and ON 013100 each exhibit IC50 value in the range of 3-5 nM, a range considered to sufficiently potent for use in a conjugate.

TABLE 3

| CELL LINE | TUMOR TYPE | ON 01500 | ON 013100 |
|---|---|---|---|
| DU145 | PROSTATE (AR−) | 0.005 | 0.005 |
| PC-3 | PROSTATE (AR+) | 0.006 | 0.005 |
| OV-CAR-3 | OVARIAN | 0.003 | 0.03 |
| Sk-OV-3 | OVARIAN | 0.003 | 0.004 |
| MIA-PaCa2 | PANCREATIC | 0.003 | 0.003 |
| U87 | GLIOBLASTOMA | 0.003 | 0.007 |
| H157 | NSCLC | 0.004 | 0.007 |
| A549 | NSCLC | 0.003 | 0.01 |
| H187 | SCLC | 0.004 | 0.003 |
| N417 | SCLC | 0.003 | 0.003 |
| AGS | GASTRIC | 0.003 | 0.005 |
| RF1 | GASTRIC | 0.002 | 0.003 |
| RF48 | GASTRIC | 0.001 | 0.001 |
| DLD-1 | COLO-RECTAL | 0.006 | 0.007 |
| HCT-116 | COLO-RECTAL | 0.006 | 0.006 |
| HCT-15 | COLO-RECTAL | 0.005 | 0.007 |
| SW480 | COLO-RECTAL | 0.006 | 0.005 |
| SK-MEL-28 | MELANOMA | 0.005 | 0.007 |
| CEM | LEUKEMIC | 0.01 | 0.004 |
| K562 | CML | 0.0025 | 0.004 |
| MOLT-4 | T-lymphoblastic:ALL | 0.004 | 0.0015 |
| Namalwa | Burkitt's Lymphoma (B-cell) | 0.005 | 0.003 |
| Daudi | Burkitt's Lymphoma (B-cell) | 0.003 | 0.003 |
| Raji | Burkitt's Lymphoma (B-cell) | 0.002 | 0.001 |

Table (3) shows the IC50 values of ON 01500 and ON 013100 against a large number of tumor cells.

TABLE 4

| CELL LINE | TUMOR TYPE | HER2 | ON 01500 | ON 013100 |
|---|---|---|---|---|
| BT20 | BREAST (ER−) | ++ | 0.004 | 0.08 |
| T47D | BREAST (ER+) | + | 0.003 | 0.01 |
| MCF-7 | BREAST (ER+) | + | 0.001 | 0.01 |
| SK-BR-3 | BREAST (ER−) | ++++ | 0.002 | 0.004 |
| BT474 | BREAST (ER+) | ++++ | 0.002 | 0.003 |

Table (4) shows the approximate levels of HER2 expression and the corresponding IC50 values for ON 01500 and ON 013100 found in a panel of breast carcinoma cell lines.

TABLE 5

| CELL LINE | CD38 | CD138 | CD20 | ON 01500 | ON 013100 |
|---|---|---|---|---|---|
| RPMI 8266 | + | + | − | .003 | .005 |
| U266 | −/+ | + | − | .003 | .005 |
| OPM-2 | + | + | − | .003 | .004 |
| NCI-H929 | + | + | − | .0008 | .001 |

Table (5) The IC50 values of ON 01500 and ON 013100 against a number of multiple myeloma (MM) cell lines.

TABLE 6

| COMPOUND | CELL LINE | IC50 (uM) | RSIST-ANCE |
|---|---|---|---|
| PACLITAXEL | MES-SA (PARENTAL) | 0.004 | |
| | MES-SA/Dx5 (RESISTANT) | 0.75 | 188 |
| ON 01500 | MES-SA (PARENTAL) | 0.004 | |
| | MES-SA/Dx5 (RESISTANT) | 0.004 | 1 |
| ON 013100 | MES-SA (PARENTAL) | 0.005 | |
| | MES-SA/Dx5 (RESISTANT) | 0.005 | 1 |
| PACLITAXEL | 2008 (PARENTAL) | 0.003 | |
| | 2008/17/4 (RESISTANT) | 2 | 667 |
| ON 01500 | 2008 (PARENTAL) | 0.003 | |
| | 2008/17/4 (RESISTANT) | 0.003 | 1 |
| ON 013100 | 2008 (PARENTAL) | 0.005 | |
| | 2008/17/4 (RESISTANT) | 0.006 | 1.3 |
| CAMPTOTHECIN | CEM (PARENTAL) | 0.002 | |
| | CEM/C2 (RESISTANT) | 1 | 500 |
| ON 01500 | CEM (PARENTAL) | 0.01 | |
| | CEM/C2 (RESISTANT) | 0.01 | 1 |
| ON 013100 | CEM (PARENTAL) | 0.004 | |
| | CEM/C2 (RESISTANT) | 0.003 | 0.75 |

Table (6) $IC_{50}$ values of ON 01500 and ON 013100 against three multidrug resistant cell lines. MDR cells are not resistant to ON 01500 or ON 013100.

TABLE 7

| Cell Line | Disease Model | Antigen Status |
|---|---|---|
| SK-BR-3 | Breast Carcinoma | HER2 High levels |
| BT474 | Breast Carcinoma | HER2 High levels |
| MCF-7 | Breast Carcinoma | HER2 Low levels |
| T47D | Breast Carcinoma | HER2 Low levels |
| RPMI-8266 | Multiple Myeloma | CD38+ CD138+ |
| U266 | Multiple Myeloma | CD38+/− CD138+ |
| LP-1 | Multiple Myeloma | CD38+ CD138− |
| OPM-2 | Multiple Myeloma | CD38+ CD138+ |

Table (7) Cell lines to be used for cytotoxicity assays

TABLE 8

| Xenograft | HER2 STATUS | Treatment Group | Dose mg/kg | Schedule | # of mice |
|---|---|---|---|---|---|
| BT474 | ++++ | VEHICLE | TBD | QD × 5 | 8 |
| BT474 | ++++ | HERCEPTIN | TBD | QD × 5 | 8 |
| BT474 | ++++ | Immunoconjugate | TBD | QD × 5 | 8 |
| BT474 | ++++ | VEHICLE | TBD | Q7D × 3 | 8 |
| BT474 | ++++ | HERCEPTIN | TBD | Q7D × 3 | 8 |
| BT474 | ++++ | Immunoconjugate | TBD | Q7D × 3 | 8 |
| T47D | + | VEHICLE | TBD | QD × 5 | 8 |
| T47D | + | HERCEPTIN | TBD | QD × 5 | 8 |
| T47D | + | Immunoconjugate | TBD | QD × 5 | 8 |
| T47D | + | VEHICLE | TBD | Q7D × 3 | 8 |
| T47D | + | HERCEPTIN | TBD | Q7D × 3 | 8 |
| T47D | + | Immunoconjugate | TBD | Q7D × 3 | 8 |

Certain embodiments of immunoconjugates described herein are targeted to HER2 expressing breast cancer cells. Certain embodiments of immunoconjugates described herein are targeted to multiple myeloma (MM) cell lines expressing the surface antigens CD38 and or CD138. The $IC_{50}$ value of ON 015100 and ON 013100 was determined for a number of breast cell lines as well as a panel of multiple myeloma cell lines expressing varying levels of each antigen and the data are shown in table (4) and table (5), respectively. Both compounds are very active against all the breast cell lines tested, and the data also show that the breast cell lines that express higher amounts of HER2 are even more sensitive ON 013100. Two cell lines, SK-BR-3 and BT474, known to express very high levels of HER2 are more than 2 fold more sensitive to ON 013100 as compared to the cell lines which express lower levels of HER2. Marx C., et al., *Validated High-Throughput Screening of Drug-Like Small Molecules for Inhibitors of ErbB2 Transcription.* Assay Drug Dev. Technology 4(3):273-84 (2006); Lostumbo, A., et al., *Flow Cytometry: A New Approach For The Molecular Profiling Of Breast Cancer*, Exp. and Molecular Pathology 80:46-53 (2006).

Table (5) shows the $IC_{50}$ values of ON 015100 and ON 013100 against a number of multiple myeloma (MM) cell lines along with the expression of a number of important surface antigens. CD138 and CD38 are both highly expressed on MM cell lines while CD20 expression has been shown to be correlated with lymphoblastoid (LCL) cell lines and not true multiple myeloma cells. Pellat-Deceunynk, C., et al., *Human Myeloma Cell Lines As A Tool For Studying The Biology Of Multiple Myeloma: A Reappraisal* 18 Years After, Blood 86(10):4001-2 (1995); Gooding, R. P., et al., *Phenotypic And Molecular Analysis Of Six Human Cell Lines Derived From Patients With Plasma Cell Dyscrasia*, British Journal of Haematology 106:669-688 (1999).

The multiple myeloma cell lines are extremely sensitive to ON 01500 and ON 013100 with $IC_{50}$ values nearing picomolar concentrations.

Therefore, one of the most important attributes of a compound that is to be conjugated to an antibody has been identified. The identification of an extremely potent chemical entity so that only a small number of molecules will be necessary to link to each IgG molecule in order to induce cell death.

ON 01500, ON 013100, and ON 24160 for example, are active against drug resistant cell lines. Another extremely important predictive factor is the ability of these compounds to kill cell lines overexpressing multiple drug resistance (MDR) genes. A very high percentage of cancer patient relapses are due to some form of resistance to traditional chemotherapy. Of these patients, the vast majority express one or more of the MDR genes within the ABC transport gene family. Overexpression of these genes increases the efflux of compounds that are recognized by these pumping systems. Therefore, even if a highly toxic compound is efficiently released from the antibody-drug conjugate within a MDR cancer cell, its effectiveness will be dramatically reduced as a result of the efflux pump. Onconova's benzyl styryl sulfone compounds are not recognized by the MDR-1 gene and therefore provide an advantage over other highly toxic drugs including but not limited to the taxanes, doxorubicin, etoposide, and vinca-alkaloids. Table (6) shows the $IC_{50}$ values of ON 01500 and ON 013100 against a number of MDR cell lines. MES-SA/Dx5, uterine sarcoma, and Apr. 17, 2008, ovarian, are both classical multidrug resistant cell lines that are cross resistant to the taxanes and anthracyclins. Harker, W G, and Sikic, B. I., *Multidrug (Pleiotropic) Resistance In Doxorubicin-Selected Variants Of The Human Sarcoma Cell Line MES-SA*, Cancer Res. 45(9):4091-6 (1985). MES-SA/Dx5 and Apr. 17, 2008 cells were found to be as sensitive to ON 01500 and ON 013100 as the parental nonresistant cell lines while being 188 and 667 fold resistant, respectively, to paclitaxel. CEM/C2 are considered non classical multiple drug resistant cell lines because they do not over express MDR-1 and are not cross resistant to taxanes, but are resistant to multiple DNA damaging agents. Fujimori, A., et al., *Mutation At The Catalytic Site Of Topoisomerase I In CEM/C2, A Human Leukemia Cell Line Resistant To Camptothecin*, Cancer Res. 55(6): 1339-46 (1995). ON 01500 and ON 013100, for example, are both extremely active against these resistant cell lines. This data suggests that ON 01500 and ON 013100 should be active against clinically relevant MDR expressing cell lines.

The current invention is particularly drawn toward method of treatment of a disease condition mediated by drug-resistant cells, e.g., a cell proliferative disorder, in a mammal comprising administering a therapeutically effective amount to said mammal of an activated cytotoxic compound attached to a targeting molecule for the treatment of a mammalian disease condition comprising, a target molecule covalently attached to an activator, a spacer linker, a self-immolative linker, and a cytotoxic drug otherwise described herein. This method is particularly preferred comprising administering a therapeutically effective amount of an activated cytotoxic compound attached to a targeting molecule wherein the cytotoxic drug is selected from the group consisting essentially of (E)-2,4,6-trimethoxystyryl-4-methoxy-3-aminobenzylsulfone (ON 01500); (E)-5-((2,4,6-trimethoxystyrylsulfonyl)methyl)-2-methoxyphenol (ON 013100); and, (E)-2,4,6-trimethoxystyryl-4-methoxy-3-aminophenylsulfonamide (ON 24160).

ON 01500 and ON 013100 Induce Mitotic Arrest and Apoptosis in Cancer Cells

Figure 6:
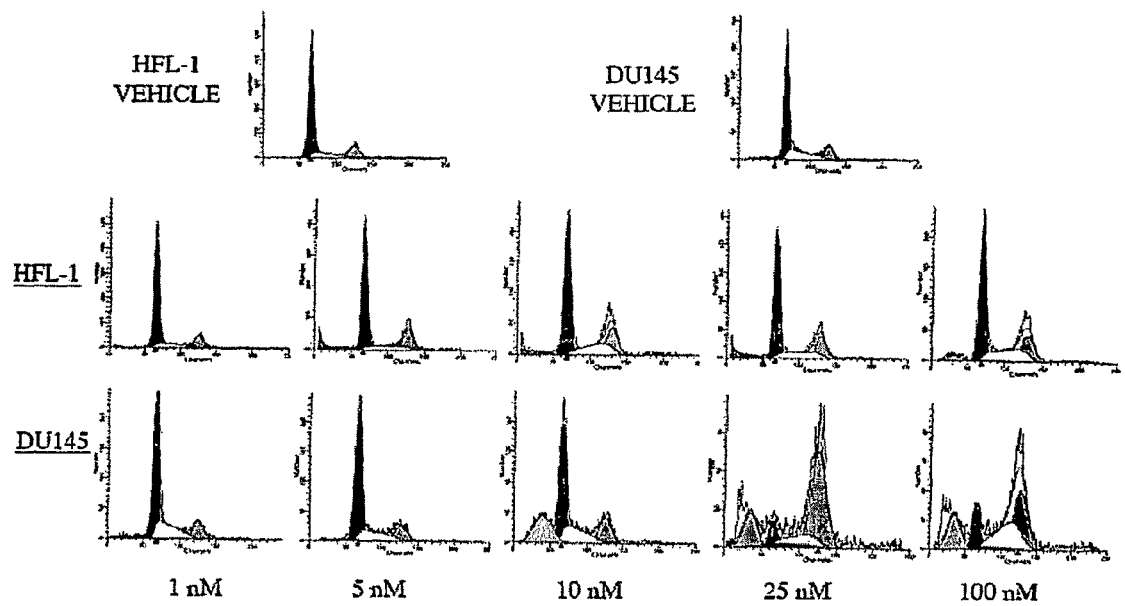
FIGS. 6.A and B illustrate the cell cycle distribution and accumulation of apoptotic cells in normal and prostate cancer cells after treatment with various concentration of the compounds ON 01500 and ON 013100—showing that these two compounds are selective towards inducing apoptosis while arresting normal cells in a cell cycle dependent manner.
Figure 6:
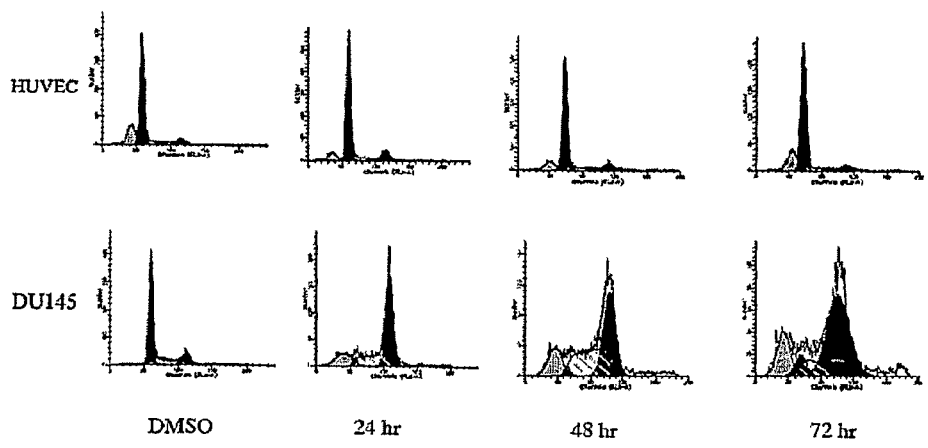

Treatment of cancer cells with either of these two compounds will result in a mitotic arrest followed by the onset of apoptosis in a dose dependent manner. FACS analysis of tumor cells versus normal cell lines is shown in FIG. 6(A, B.). FACS analysis of normal and tumor cells treated with ON 01500 and ON 013100. A. Cells treated for 24 hrs with ON 01500. B. Cells treated with ON 013100 (20 nM) and harvested at various time points thereafter. FIG. 6. A shows the cell cycle distribution and accumulation of cells with sub2N DNA content (apoptotic cells) of normal diploid lung fibroblasts (HFL-1) and prostate cancer cells (DU145) after treatment with various concentration of ON 01500. At 24 hours of treatment it is evident that ON 01500 induces an accumulation of cells with 4N DNA and the induction of apoptosis of the tumor cells. When normal cells are treated with an equal concentration of ON 01500 the cells have a slight arrest in G2/M with a greatly reduced induction of apoptosis. ON 013100 treatment of normal human umbilical vein endothelial cells (HLVECs) results in a similar cell cycle distribution. FIG. 6.B illustrates cells that have been treated over 72 hours. The prostate cancer cells enter into the G2/M arrest followed by apoptosis in a time dependent manner, while the HUVECs show an arrest in the G1 stage of the cell cycle. This data shows that these two compounds are selective towards inducing apoptosis while arresting normal cells in a cell cycle dependent manner. This characteristic should greatly increase the "therapeutic window" of the resulting immunoconjugates since there are now two layers of selectivity. The first being the selective binding and release of the cytotoxic compound only in cells expressing the tumor specific antigen, and the innate selectivity of the compounds themselves. This will provide additional protection of the patient if non-selective binding or release occurs.

ON 01500 and ON 013100 are Effective Against Human Tumor Xenografts

The in vivo activity of ON 01500 and ON 013100 was studied in a nude mouse xenograft model system. Human breast carcinoma (BT20) cells were injected subcutaneously into female athymic nude mice (ncr/ncr). When the average tumor size was approximately 100 mm$^3$, the mice were treated with either ON 01500 (DMSO) or ON 013100 (formulated as a phosphate salt) by intraperitoneal injections (IP). The average tumor volume and body weights were determined on the indicated days.

Figure 7:
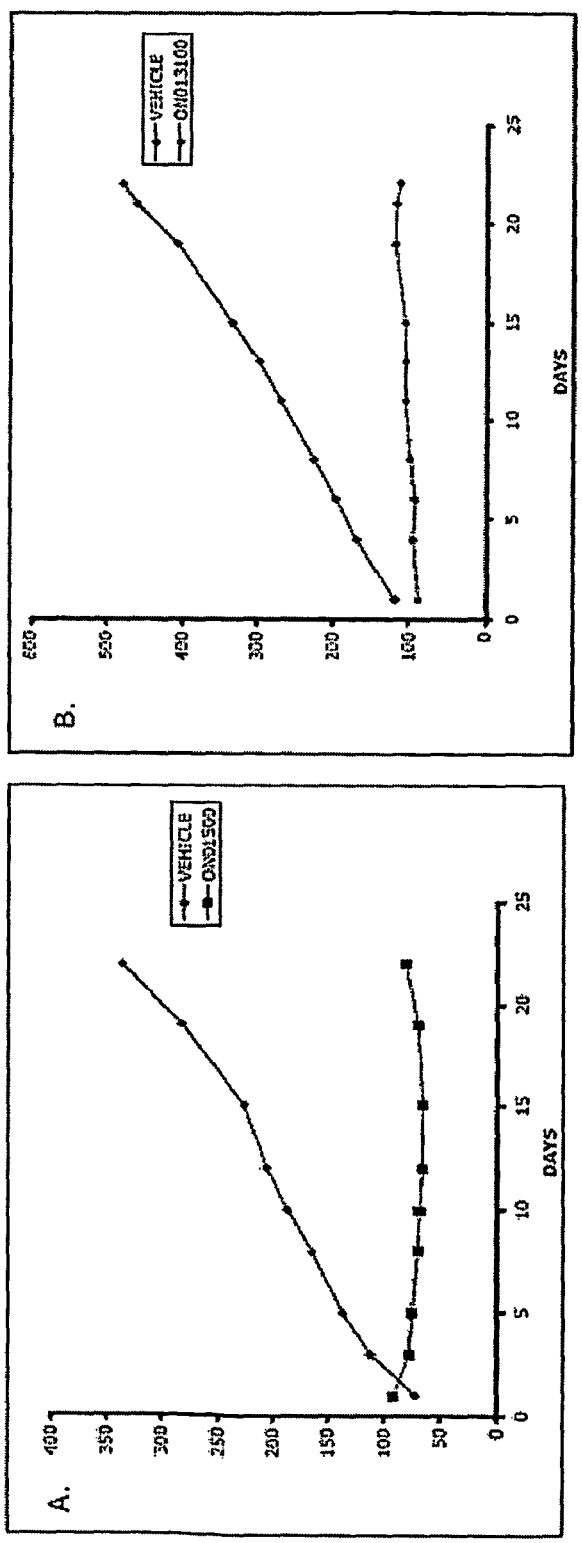
FIGS. 7.A and B illustrate anti-tumor activity of ON 01500 and ON 013100, for example. The growth of the tumors are significantly reduced without toxicity in mice bearing human tumors.

FIG. 7 Antitumor activity of ON 01500 and ON 013100. BT20 cells were injected in female nude mice. The mice (N=5-8) were treated with ON 01500 (Panel A.) at 10 mg/kg by IP injections or Vehicle alone (DMSO) every other day Q2Dx3. The mice were treated (Panel B) with ON 013100 (Phosphate salt) at 50 mg/kg Q2Dx3 or with or with phosphate buffered saline by IV injections. The figure shows that both compounds are extremely effective at inhibiting the in vivo growth of tumor cells. FIG. 7.A shows the growth of BT20 tumors in mice treated with vehicle (DMSO) or ON 01500 (10 mg/kg Q2Dx3). The BT20 tumor growth was significantly inhibited by ON 01500 injections without any signs of weight loss or toxicity. ON 013100 was converted into an aqueous soluble phosphate salt and mice were treated at 50 mg/kg every other day by IV injections. FIG. 7.B shows the growth of the BT20 tumors was significantly inhibited by this dose and schedule. The treated mice exhibited no weight loss and no apparent signs of toxicity. This data clearly shows that when mice bearing human tumors are treated with ON 01500 and ON 013100, the growth of the tumors are significantly reduced without toxicity.

Immunoconjugates of Benzyl Styryl Sulfones

Immunoconjugates of Trastuzumab and a CD138(+) multiple myeloma mAb are prepared and evaluated to establish synergistic improvements between these therapeutic monoclonal antibodies and the established potencies of ON 013100 and ON 01500, for example. See, EXAMPLE V. Trastuzumab and the anti-CD138 mAb are exemplified since these proteins lie at the heart of validated molecular targets for which there remains a critical need for improved chemotherapy. Trastuzumab, however, has a very limited clinical benefit as a single agent and is limited to carcinomas with an extremely high overexpression of HER2. In addition, a recent report describing the preparation and improved biological activity of a Trastuzumab-Geldanamycin immunoconjugate, provides a standard for which immunoconjugates of ON 01500 and ON 013100 can be measured. Mandler, R., et al., *Trastuzumab-Geldanamycin Immunoconjugates: Pharmacokinetics, Biodistribution, and Enhanced Antitumor Activity*, Cancer Res. 64:1460-1467 (2004).

The examples presented herein evaluate ADCs (activated cytotoxic compound attached to a targeting molecule) of ON 01500 and ON 013100 generated from the murine IgG$_1$ anti-CD138 monoclonal antibody, B—B4. Wijdenes, J., et al., *A Plasmocyte Selective Monoclonal Antibody* (B—B4) *Recognizes Syndecan*-1, Br J Haematol. 94(2):318-23 (1996). The CD138 (Syndecan-1) antigen is prevalent in multiple myeloma, and thus far mAb therapy surrounding this biological target has not met clinical expectations or entered into clinical trials. Klein, B., et al., *Activation Molecules On Human Myeloma Cells*, Curr Top Microbiol Immunol. 246: 335-41 (1999). A report from the Dana-Farber Cancer Institute that describes the cytotoxicity of the maytansinoid immunoconjugate B—B4-DM1 against CD138(+) multiple myeloma cells. Tassone, P., et al., *Cytotoxic Activity Of The Maytansinoid Immunoconjugate* B—B4-DM1 *Against CD138+ Multiple Myeloma Cells*, Blood 104(12):3688-3696 (2004).

Administration and Dosage

Activated cytotoxic compounds attached to a targeting molecules of the present invention are preferably administered to mammals or patients in need of treatment by means of intravenous injection within the range of a concentration of about 0.1 mg/kg to about 50 mg/kg. Depending upon the targeting molecule, a dosage may also efficaciously be within the range of about 0.5 mg/kg to about 25 mg/kg. An effective dosage may also be within the range of about 1 mg/kg to about 10 mg/kg. Activated cytotoxic compounds attached to a targeting molecules of the present invention may be formulated and administered similar to HERCEPTIN®, for example, i.e., (440 mg) formulated in 20 ml bacteriostatic water for injection (BWFI) to arrive at a total concentration of around 21 mg/mL. HERCEPTIN®, for example, is administered at 4 mg/kg as an IV infusion using 250 mL 0.9% sodium chloride (NOT IV push or bolus injection) over 90 minutes for initial treatment; 2 mg/kg over 30 minutes on a weekly maintenance basis thereafter. Other FDA-approved antibodies are currently available for human administration. Activated cytotoxic compounds attached to a targeting molecules of the present invention, accordingly, are expected to be administered in substantially the same manner and in similar amounts as current biopharmaceuticals.

As used herein BOC=tert-Butyloxycarbonyl; TFA=trifluoroacetic acid; DIEA=Diisopropylethylamine; NHS=N-Hydroxysuccinimidyl; EDCI=(3-Dimethylaminopropyl)-3-ethylcarbodiimide hydrochloride; DMF=N,N-Dimethylformamide; DCC=N,N'-Dicyclohexylcarbodiimide; and, THF=Tetrahydrofuran.

EXAMPLES

Example I

Synthesis of (E)-2,4,6-trimethoxystyryl-4-methoxy-3-aminobenzylsulfone (ON 01500)

(E)-2,4,6-Trimethoxystyryl-3-Amino-4-Methoxybenzyl Sulfone

Step 1: Preparation of 4-Methoxy-3-Nitro benzylbromide

A solution of 4-methyl-2-nitroanisole (25 mmol), N-bromosuccinimide (25 mmol) and benzoyl peroxide (2.5 mmol) in carbon tetrachloride (100 mL) was heated at reflux for 18 h. The reaction mixture was then poured into water and solid separated was filtered. The aqueous layer was extracted with carbon tetrachloride (3×50 mL) and organic phase was separated and evaporated to give a solid product. The solid products were combined and recrystallized from ethyl acetate-hexane to give a crystalline product of 3-nitro-4-methoxy benzyl bromide. m.p. 110-112° C., yield 70-75%.

Step 2: Synthesis of 4-Methoxy-3-Nitrobenzylthioacetic acid

To a cold solution of sodium hydroxide (9.75 g, 240 mmol) in methanol (200 mL), thioglycollic acid (11.25 g, 120 mmol) was added slowly over 30 minutes. Sodium thioglycollate precipitated was dissolved by stirring and warming up the solution. The solution was cooled to room temperature and 4-methoxy-3-nitrobenzyl chloride (30.0 g, 120 mmol) was added in portions to reduce the intensity of exothermic reaction. The reaction mixture was then refluxed for 4 hours, cooled and poured onto crushed ice (1 Kg) containing hydrochloric acid (50 mL). The precipitate formed was filtered, washed with ice cold water and dried under vacuum. (30.0 g, 95% yield) m.p. 130-132° C.

Step 3: Synthesis of 4-Methoxy-3-Nitrobenzylsulfonylacetic acid 4-methoxy-benzylthioacetic acid (10 g) was dissolved in glacial acetic acid (80 mL) and 30% hydrogen peroxide (20 mL) was added in one portion and the mixture was stirred at room temperature for 10 hours. The contents of the flask were cooled and poured on to the crushed ice (500 g). The yellow precipitate formed, filtered, washed with cold water and dried (55% yield). Recrystallization from hot water yielded crystals 4-methoxy-3-nitrobenzylsulfonyl acetic acid. m.p. 96-98° C.

Step 4: Synthesis of (E)-2,4,6-Trimethoxystyryl-4Methoxy-3-Nitrobenzylsulfone

A solution of 4-methoxy-3-mitrobenzyl sulfonylacetic acid (4.5 g, 15.5 mmol) in 30 ml of glacial acetic was treated with 2,4,6-trimethoxybenzylsulfone (3.05 g, 15.5 mmol) in the presence of catalytic amounts of benzylamine (0.6 mL). The reaction mixture was refluxed for 6 hours and acetic acid was removed under vacuum. The gummy material obtained was treated with 2-propanol to yield a solid product which was recrystallized from a mixture of acetic acid and 2-propanol. Yield 28%, m.p. 186-187° C.

Step 5: Reduction of (E)-2,4,6-Trimethoxystyryl-4-Methoxy-3-Nitrobenzylsulfone

Method 1

Synthesis of (E)-2,4,6-Trimethoxystyryl-4-Methoxy-3-Aminobenzylsulfone

A solution of (E)-2,4,6-trimethoxystyryl-4-methoxy-3-nitrobenzylsulfone (1.3 mmol) in acetone-water (10:5) was heated to 50° C. After 30 min, sodium hydrosulfite ($Na_2S_2O_4$) (26.3 mmol) was added slowly, and the mixture was heated at reflux (50° C., 1 h.), cooled to room temperature and water was added. The product was rinsed with $NaHCO_3$, and then isolated by extraction with ethyl acetate. The organic layer was dried over anhydrous $Na_2SO_4$. The solvent was removed under reduced pressure and the crude product was recrystallized from 2-propanol, m.p. 148-150° C.

The reduction of (E)-2,4,6-trimethoxystyryl-4-methoxy-3-nitrobenzylsulfone to (E)-2,4,6-trimethoxystyryl-4-methoxy-3-aminobenzylsulfone was also performed by the following method.

Reduction of (E)-2,4,6-Trimethoxystyryl-4-methoxy-3-nitrobenzylsulfone: Method 2

5% Pd/C wet (10% by weight of the nitro compound) was charged into a flask. Pd/C was wetted with ethanol by slowly adding through the sides of the flask. The nitro compound (10 mmol) is added to the flask and then 20 volume equivalents of ethanol is added. The temperature of the flask was raised to 50-60° C. Then hydrazine hydrate (26 equivalents) is added over a period of 15-20 min. It is then refluxed for 5-6 hours. The completion of the reaction was monitored every hour by TLC. After completion of the reaction, Pd/C was filtered while the solution was hot and the filtrate was washed with 2 volumes of hot ethanol. The volume of ethanol was reduced to 50% by distilling under reduced pressure and 10 volumes of ice cold water was added. The solution was stirred for 30 min and the precipitated solid was filtered and dried under vacuum and recrystallized from 2-propanol to give 2,4,6-trimethoxystyryl-4-methoxy-3-aminobenzylsulfone, m.p. 148-150° C.

Example II

Synthesis of (E)-5-((2,4,6-trimethoxystyrylsulfonyl)methyl)-2-methoxyphenol (ON 013100)

A. 3-O-tert-Butyldimethyl silyloxy-4-methoxy benzaldehyde

To a cooled (0° C.) solution of 3-hydroxy-4-methoxy benzaldehyde (10 g, 65.7 mmol, 1 eq) in dry DMF (75 mL) was added DIPEA (16.99 g, 131.4 mmol, 2 eq). The mixture was stirred under nitrogen for 10 min. A 1.0 M solution of t-BDMS-Cl in THF (78.9 mL, 1.2 eq) was added dropwise over 30 min. The resulting mixture was stirred 12-16 h and monitored by thin layer chromatography (TLC). When the reaction was complete, water (75 mL) was added to the reaction mixture. The resulting mixture was extracted with DCM (3×75 mL). The combined organic layer was washed with saturated aqueous sodium bicarbonate (75 mL) and water (75 mL) and dried ($Na_2SO_4$). Volatile components were removed in vacuo to yield the crude product. The crude product was purified by column chromatography on silica eluted with $CHCl_3$ to afford the product (Yield; 26.75 g), 3-O-tert-butyldimethyl silyloxy-4-methoxy benzaldehyde, as a yellow oil.

B. 3-O-tert-butyldimethylsilyloxy-4-methoxy benzyl alcohol

To a cooled (0° C.) solution of 3-O-tert-butyldimethyl silyloxy-4-methoxy benzaldehyde (13 g, 48.8 mmol, 1 eq) in methanol (100 mL) under nitrogen, was added sodium borohydride (1 eq). The resulting mixture was allowed to warm to room temperature and stirred (30 min) and monitored by TLC. When the reduction was complete, water-ice was added to the reaction mixture. The resulting mixture was extracted with ethyl acetate (3×50 mL). The combined organic extract was washed with water (50 mL) and dried ($Na_2SO_4$). Volatile components were removed in vacuo to afford a 73.5% yield of the desired product, 3-O-tert-butyldimethylsilyloxy-4-methoxy benzyl alcohol.

C. 3-O-tert-butyldimethylsilyloxy-4-methoxy benzyl chloride

To a cooled (0° C.) solution of 3-O-tert-butyldimethylsilyloxy-4-methoxy benzyl alcohol (9.5 g, 35.4 mmol, 1 eq) in benzene (50 mL) under nitrogen, was added thionyl chloride (6.32 g, 1.5 eq) dissolved in benzene (5 mL) dropwise over 10 min. The resulting mixture was stirred at 0° C. and monitored by TLC. When the reaction was complete, water ice (50 g) was added and the resulting mixture was extracted with ethyl acetate (3×50 mL). The combined organic extract was washed with saturated bicarbonate solution (50 mL) and water (50 mL) and dried ($Na_2SO_4$). Volatile components were removed in vacuo to afford a quantitative yield of the product 3-O-tert-butyldimethylsilyloxy-4-methoxy benzyl chloride as a yellow oil.

D. 2-((3-O-tert-butyldimethylsilyloxy-4-methoxybenzyl)sulfanyl)acetic acid

To a solution of sodium hydroxide (2.79 g, 69.7 mmol, 2 eq) in methanol (30 mL) was added mercaptoacetic acid (3.21 g, 34.9 mmol, 1 eq) dropwise over 10 min. 3-O-tert-Butyldimethylsilyloxy-4-methoxy benzyl chloride was added portionwise to the mercaptoacetic acid mixture and the resulting mixture was stirred at room temperature and monitored by TLC. When the reaction was complete, the reaction mixture was poured onto ice (100 mL) containing concentrated HCl (excess based on sodium hydroxide). The resulting mixture was extracted with ethyl acetate (3×50 mL). The combined organic extract was washed with water (30 mL) and dried ($Na_2SO_4$). Volatile components were removed in vacuo to afford a 75% yield of the desired product 2-((3-O-tert-butyldimethylsilyloxy-4-methoxybenzyl)sulfanyl)acetic acid as a solid having a melting point of 57-59° C.

E. 2-((3-hydroxy-4-methoxybenzyl)sulfanyl)acetic acid

To a cooled (0° C.) solution of 2-((3-O-tert-butyldimethylsilyloxy-4-methoxybenzyl)sulfanyl)acetic acid (8.75 g, 25.5 mmol, 1 eq.) in THF (40 mL) was added dropwise, TBAF (1 eq., 1M in THF). The resulting mixture was stirred under nitrogen at room temperature and monitored by TLC. When the reaction was complete, water (40 mL) was added to the reaction mixture. The resulting mixture was extracted with ethyl acetate (3×40 mL). The combined organic extract was washed with water (40 mL) and dried ($Na_2SO_4$). Volatile components were removed in vacuo to yield the crude product, which was purified by column chromatography to afford a 50% yield of the purified product, 2-((3-hydroxy-4-methoxybenzyl)sulfanyl)acetic acid.

F. 3-hydroxy-4-methoxy benzyl sulfoneacetic acid

To a solution of 2-((3-hydroxy-4-methoxybenzyl)sulfanyl) acetic acid (2.9 g) in glacial acetic acid (15 mL) was added hydrogen peroxide (6 mL, 30% solution). The resulting mixture was stirred over night at room temperature and monitored by TLC. When the reaction was complete, the reaction mixture was poured into ice water (10 mL) and extracted with ethyl acetate (3×10 mL). The combined organic extract was washed with water (10 mL) and dried ($Na_2SO_4$). Volatile components were removed in vacuo to afford a 60% yield of the pure product 3-hydroxy-4-methoxy benzyl sulfoneacetic acid having a melting point of 164-165° C.

G. (E)-5-((2,4,6-trimethoxystyrylsulfonyl)methyl)-2-methoxyphenol

A mixture of the 3-hydroxy-4-methoxy benzyl sulfoneacetic acid (1.9 g, 7.3 mmol, 1 eq), 2,4,6-trimethoxybenzaldehyde (1.58 g, 8.0 mmol, 1.1 eq), benzoic acid (134 mg, 0.15 eq) and piperidine (81 mg, 0.13 eq) in toluene (50 mL) was heated at reflux temperature for 2-3 h with continuous removal of water using a Dean-Stark trap. When the reaction was complete by TLC analysis, the reaction mixture was cooled to room temperature. Water was added and the resulting mixture was extracted with ethyl acetate (3×50 mL). The combined organic extract was washed with saturated aqueous sodium bicarbonate solution (50 mL), dilute hydrochloric acid (50 mL), and water (50 mL) and dried ($Na_2SO_4$). Volatile components were removed in vacuo to yield the crude product, which was purified by recrystallization from isopropanol to yield (1.8 g, 62.5%) of the desired (E)-5-((2,4,6-trimethoxystyrylsulfonyl)methyl)-2-methoxyphenol.

Example III

Synthesis of (E)-2,4,6-trimethoxystyryl-4-methoxy-3-aminophenylsulfonamide (ON 24160)

Preparation of 2,4,6-Trimethoxy styryl-N-(3-Amino-4-methoxyphenyl)Sulfonamide 2,4,6-trimethoxystyryl-N-(4-methoxy-3-nitrophenyl)sulfonamide (7 mmol) (See, e.g., PCT publication WO03072063) was dissolved in ethanol (55 mL) in a round bottomed flask. Palladium catalyst (5% Pd/C, 275 mg) was added. Hydrazine hydrate (182 mmol) was then added in one portion. The resulting mixture was refluxed for 5 h and the reaction progress was monitored by TLC. When the reaction was complete, the palladium catalyst was removed by filtration and the filtrate was poured into a beaker containing ice cold water. The solution was stirred and a solid precipitate formed. The precipitated material was separated by filtration and dried in vacuum.
(m.p. 143-145; yield 48%)

Alternate Reduction Procedure via Sodium Dithionite

A solution of 2,4,6-trimethoxy styryl-N-(4-methoxy-3-nitrophenyl)sulfonamide (1.3 mmol) was dissolved in a 2:1 mixture of acetone and water (10 mL) and heated to 50° C. After 30 min at 50° C., sodiumdithionite ($Na_2S_2O_4$) (26.3 mmol) was added slowly, and the resulting mixture was maintained at reflux (50° C.) for 1 hour, and then cooled to room temperature. Water was added and a precipitate formed. The solid product was washed with aqueous $NaHCO_3$, and then taken up in ethyl acetate and dried over anhydrous $Na_2SO_4$. The solvent was removed under reduced pressure and the crude product was purified by column chromatography. (m.p. 143-145° C.)

Example IV

Example Activation of 3100 ((E)-5-((2,4,6-trimethoxystyrylsulfonyl)methyl)-2-methoxyphenol (ON 013100)) (Activated for Attachment to Targeting Molecules to Create Drug Delivery Entities)

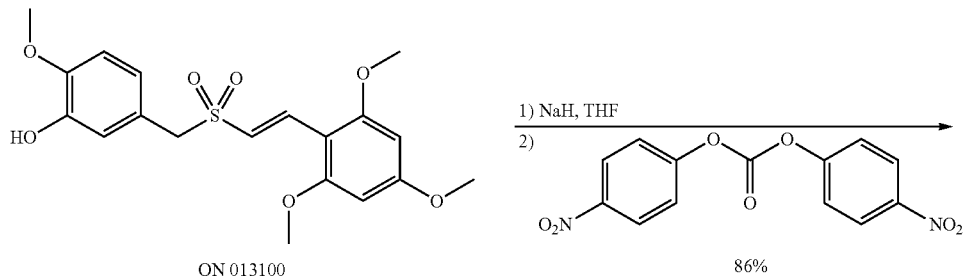

ON 013100

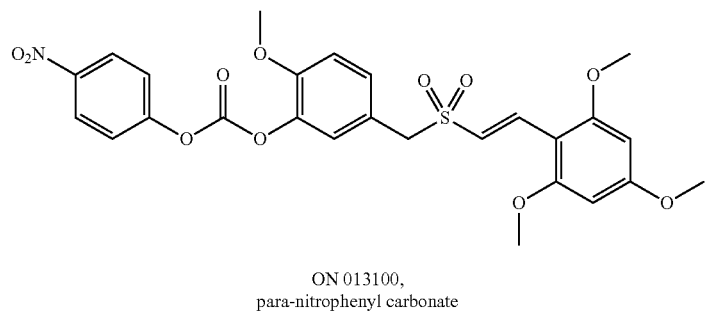

ON 013100,
para-nitrophenyl carbonate

To a thoroughly mixed and vigorously stirring mixture of ON 013100 (500 mg, 1.27 mmol) and degreased sodium hydride (30.4 mg, 1.27 mmol) was added anhydrous THF (12 mL). Immediately, vigorous evolution of hydrogen gas was observed, which subsided within about five minutes. At this time, the resulting solution was added to a vigorously stirring slurry containing bis(4-nitrophenyl)carbonate (964.0 mg, 3.17 mmol, 2.5 equiv) in THF (4.0 mL). Immediately, the resulting fine slurry turned bright orange; TLC analysis after one hour of stirring showed that the reaction was complete. The fine precipitate was removed by filtration on a scintered glass funnel, and the filter cake was washed with copious amounts of fresh THF. The filtrate was then concentrated and the crude product purified via flash silica chromatography (18 grams silica; 1:1-3:1 EtOAc/Hexanes) providing 609.4 mg of an off white solid (86%).

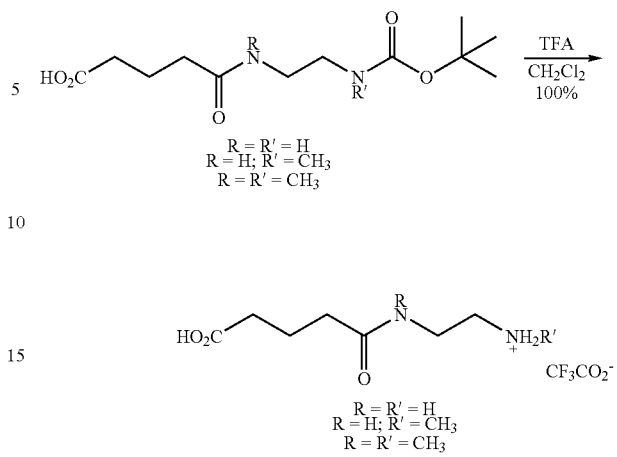

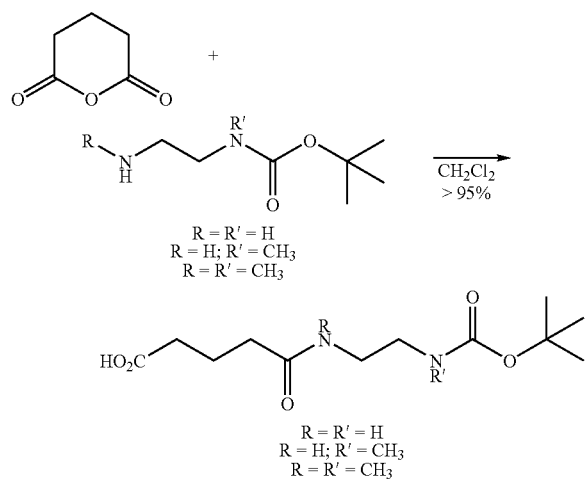

General Procedure

To a vigorously stirring room temperature solution of N'-BOC-N-glutarylethylenediamine reagent in $CH_2Cl_2$ (0.2 M) was added trifluoroacetic acid (10 equiv) in enough $CH_2Cl2$ to make the final concentration of the N'-BOC-N-glutarylethylenediamine reagent equal to 0.1 M. Progress of the reaction was monitored by TLC; reaction time varied from 4-12 hours dependent upon reaction scale. Reaction workup required evaporation, azeotropic distillation from toluene, and overnight drying under high vacuum. Yields were quantitative; products exist as viscous tacky oils.

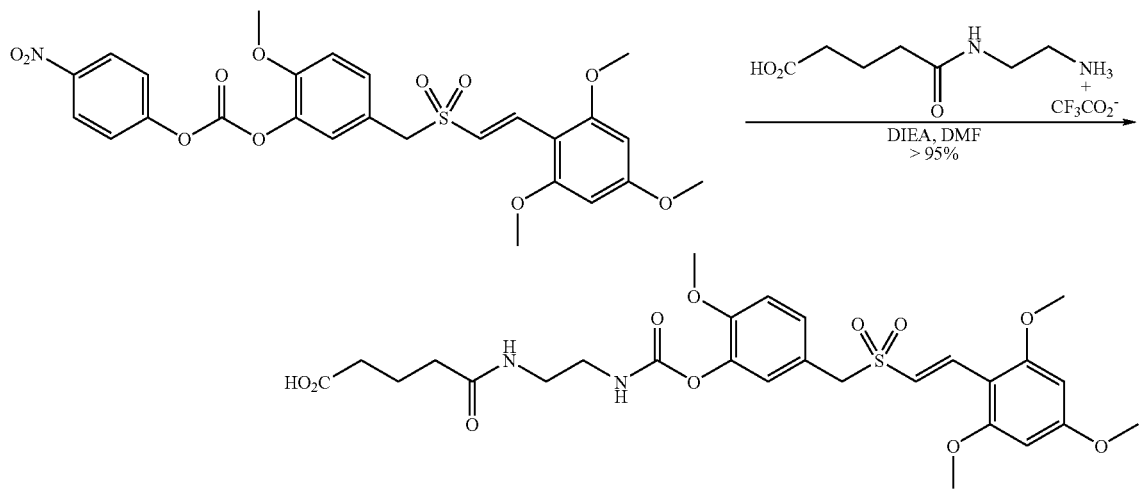

General Procedure

To a stirring solution of glutaric anhydride (2.87 mmol, 1.0 equiv) in $CH_2Cl_2$ (7 mL) was added in rapid dropwise fashion, the ethylenediamine reagent (2.87 mmol, 1.0 equiv) in $CH_2Cl_2$ (7 mL). The resulting reaction was monitored by TLC (95:4:1 EtOAc/MeOH/AcOH) and usually complete within 1-4 hours. The reaction is typically concentrated to complete dryness without any need for further purification. Yield range=95-100%; products exist as tacky solids.

ON 013100, paranitrophenyl carbonate (100 mg, 178.7 μmol), N-glutarylethylene diamine TFA salt (75.5 mg, 187.6 μmol, 1.05 equiv), methylene chloride (1.7 mL) were combined to form a suspension. To the stirring room temperature mixture was added diisopropylethylamine (155.6 μL, 893.5 μmol, 5.0 equiv). Despite considerable efforts, a tacky film lined the reaction vessel and it appeared that the starting materials were not completely soluble. Thin layer chromatography indicated that reaction starting materials remained unchanged. The reaction was then concentrated followed by the addition DMF (1.7 mL). Immediately, a bright yellow homogeneous solution resulted. Subsequent thin layer chromatography after one hour of stirring showed the reaction to be nearly complete. The reaction was allowed to stir overnight and then was concentrated to near complete dryness. Purification involved flash silica chromatography (95:4:1 EtOAc/MeOH/AcOH) producing 107 mg carbamate product (100%) as a white powder.

Mass (calculated)=594.63; mass (observed)=595.2 $(M+H^+)$, 617.3 $(M+Na^+)$ whereby TLC indicated that the reaction was clean and complete. The reaction solution was concentrated to near complete dryness and the crude residue was dissolved in EtOAc (10 mL) with the aid of a small amount of methanol and washed with $H_2O$ (3×5 mL). The aqueous fractions were combined and back extracted with EtOAc (2 mL). The organic fractions were combined and concentrated to complete dryness, providing 48 mg of the NHS ester product ON 12013100 (100%) as a white foamy solid (pure by TLC).

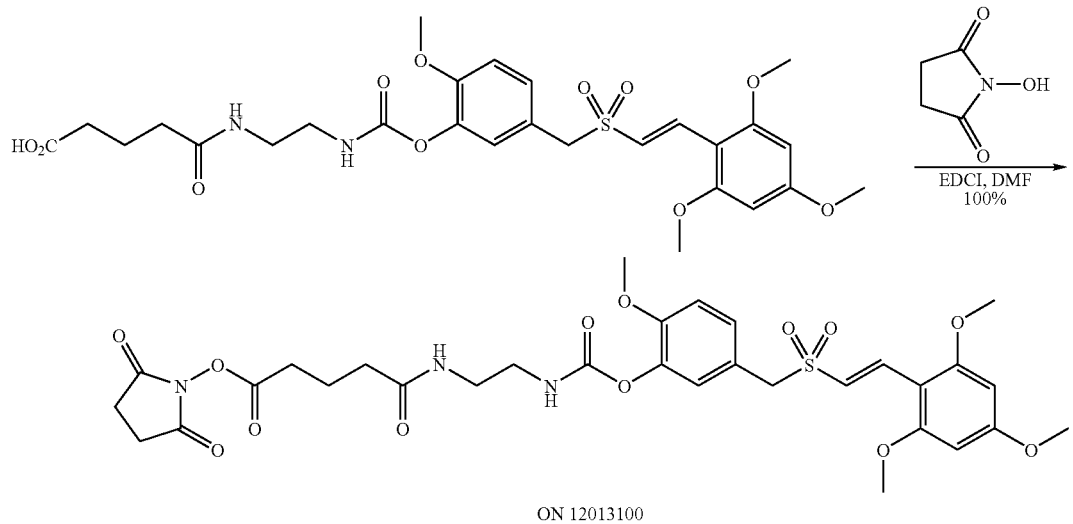

To a vigorously stirring mixture containing ON 013100, carbamate (41.2 mg, 69.2 μmol), N-hydroxysuccinimide (12.0 mg, 103.9 μmol, 1.5 equiv), and DMF (1.0 mL) was added 1-(3-dimethylaminopropyl)-3-ethylcarbodiimide hydrochloride (EDCI) (19.9 mg, 103.9 μmol, 1.5 equiv). The resulting solution was stirred overnight at room temperature,

Example V

Attachment of an Activated Cytotoxic Compound to a Targeting Molecule for the Treatment of a Mammalian Disease Condition

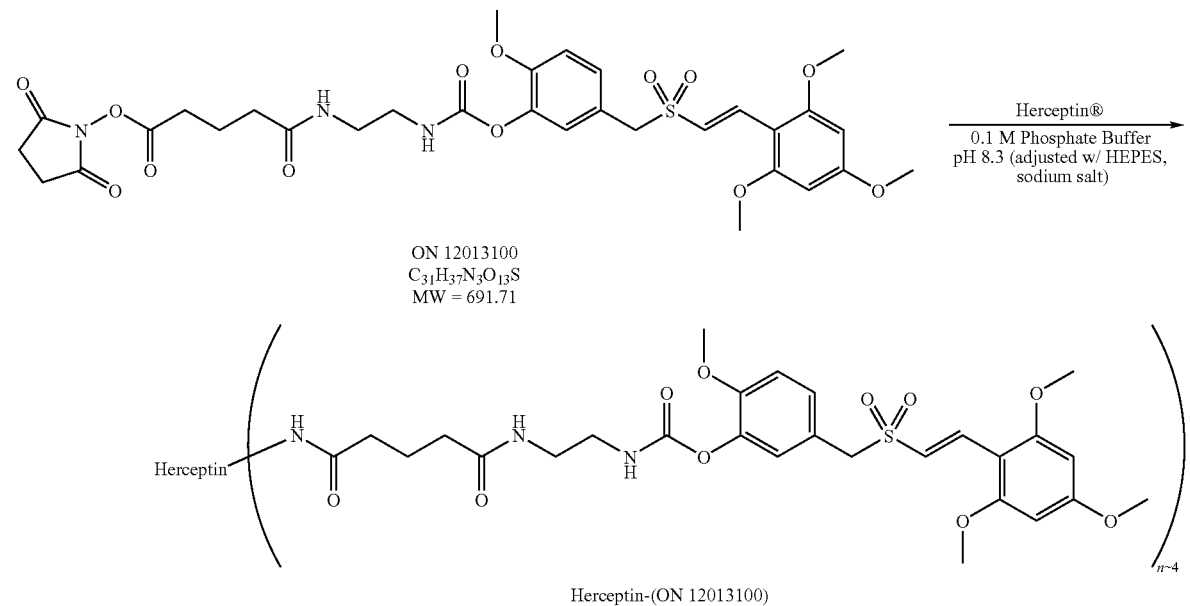

Herceptin® in original formulation (440 mg Trastuzumab, 400 mg α,α-trehalose dihydrate, 9.9 mg L-histidine HCl, 6.4 mg L-histidine, and 1.8 mg polysorbate 20, USP dissolved in 20 mL Bacteriostatic Water for Injection) is passed through a Biomax 50K Nominal Molecular Weight Limit (NMWL) Ultrafree Centrifugal Filter Device (Millipore Corporation) to separate the protein and reconstitute in 0.1 M phosphate, pH adjusted to 8.3 using HEPES, sodium salt. The Herceptin® concentration is determined by size exclusion high pressure liquid chromatography SEC-HPLC analysis using a TSKgel Super SW3000 column (4.6 mm (ID)×30.0 cm (L)) (Tosoh Bioscience, LLC), eluting with an isocratic mixture of 0.1 M phosphate, 0.1 M $Na_2SO_4$(aq) and 0.05% $NaN_3$(aq) and monitoring at a wavelength of 280 nanometers. Herceptin® is then mixed with a solution of ON 12013100 in DMF (1 mg/mL) at room temperature, and the progress of the reaction is monitored by SEC-HPLC at wavelengths of 280 nM (antibody) and 305-312 nM (ON 12013100 chromophore). The reaction is typically complete in less than one hour, and the reaction solution is passed through a Biomax 50K NMWL Ultrafree Centrifugal Filter Device to remove excess reagent and byproduct (in this case N-Hydroxysuccinimide). The reaction medium is exchanged with 0.1 M phosphate solution and the Herceptin®-(ON 12013100) conjugate is used without further purification; the immunoconjugate exhibits excellent stability when stored between 2-5° C.

HEPES, sodium salt=Sodium N-(2-Hydroxyethyl)piperazine-N'-(2-ethanesulfonate) or Sodium 4-(2-Hydroxyethyl)piperazine-1-ethanesulfonate; CAS Reg. No. 75277-39-3; $NaN_3$=Sodium azide; DMF=N,N-Dimethylformamide; $Na_2SO_4$=Sodium sulfate.

Example VI

General Preparation of Prodrugs ON 12013100, ON 14013100, and ON 16013100

FIGS. 1.A and 1.B illustrates example synthetic schemes for prodrugs (activated cytotoxic compounds) ON 12013100, ON 14013100, and ON 16013100, each of which is suitable for attachment to a targeting molecule.

Reaction of glutaric anhydride with mono-BOC-protected ethylenediamines provides efficient entry to the glutaryl-ethylene diamine linker motif bearing either one, two, or no methyl groups on the nitrogen atoms. Removal of the BOC protection with trifluoracetic acid or a suitable alternative acid provides the corresponding TFA salt in high yield. These salts when combined with ON 013100, para-nitrophenyl carbonate (prepared from ON 013100 and bis(4-nitrophenyl) carbonate) and diisopropylethylamine (DIEA) in methylene chloride furnishes the corresponding carbamate derivatives of ON 013100. Conversion of the ON 013100 carbamate derivatives to the corresponding N-hydroxysuccinimidyl (NHS) esters was achieved by either using EDCI/DMF or DCC/THF at room temperature, thus affording activated prodrugs ON 12013100, ON 14013100, and ON 16013100—ready for conjugation to antibodies, proteins, or peptides of therapeutic interest.

Example VII

Synthesis and Stability Evaluation of Prodrugs Derived from ON 01500 and ON 013100

This example synthesis of prodrug compounds involves traditional synthetic methodologies using common, inexpensive reagents. Bodansky, M., et al., *The Practice of Peptide Synthesis* ($2^{nd}$ Edition), Springer-Verlag, Berlin (1995). Assessment of chemical stability of antibody-prodrug conjugates in the blood compartment involves incubation of prodrug molecules possessing differing linkage types with the sera of three mammalian species—murine, fetal bovine, and human, followed by HPLC analysis of the deproteinized samples.

In cases where prodrugs incorporate enzyme-activated linkers, research grade enzymes are used. Published protocols are followed to assess the rate of release of active compound from the prodrug. Active compound is tested by cytotoxicity assays.

Each serum type is introduced as 0.2 mL aliquots in 11×0.5 mL Eppendorf tubes. To each tube is added 20 µL of prodrug as a 1 mg/mL solution in DMSO. One tube from each serum type is immediately flash frozen at −78° C. as a zero time control. One half of the remaining tubes are incubated at 4° C. and the other half at 37° C. Tubes are then pulled at preselected time points (e.g. 4 hrs and 24 hrs) and flash frozen at −78° C. The samples are analyzed by HPLC for release of parent drug and any other products.

Example VIII

Preparation and Characterization of Antibody-Drug-Conjugates (ADCs) (Activated Cytotoxic Compound Attached to a Targeting Molecule) with Example Small Molecule Cell Cycle Inhibitors The utility of N-Hydroxysuccinimide (NHS esters) in peptide coupling methodology has been well documented in the literature. NHS esters are kinetically more reactive with amino groups than with other competing nucleophiles, such as hydroxyl and sulfhydryl groups, and it is these differences in reactivity that have been exploited when conjugating carboxyl-bearing prodrugs to mAbs. In addition, antibodies contain approximately thirteen lysine residues in their framework, thus providing sufficient opportunity for the conjugation of multiple prodrug molecules. By adjusting the molar ratio of NHS ester reagent to protein the level of conjugation can be controlled to create an antibody with the desired number of attached drug molecules. For example, The NHS-activated ester, ON 14013100 (an NHS-activated prodrug of ON 013100), was reacted with murine IgG (Zymed 02-6100) at pH 8.3. When the molar ratio of ON 14013100 to antibody was approximately 4:1, a soluble ADC was obtained in 30 minutes at room temperature. In similar fashion, a soluble ADC formed from the reaction of ON 14013100 (an NHS-activated prodrug of ON 013100) and Trastuzumab.

Example IX

Characterization of ADCs with Regard to Drug Attachment and Protein Aggregation

ADCs are characterized by Ultra-violet (UV) spectroscopy as well as mass spectroscopy and size exclusion chromatography (SEC). SEC is especially useful for detecting any protein aggregates formed during synthesis of ADCs. Antibody molecules, which are retained by the chromatographic column, are separated from large protein aggregates, which are exclude from the resin particles. Unreacted reagents, which will be very strongly retained by the resin particles are likewise separated from the antibody. As a result, in instances where the prodrug has a distinct ultraviolet (UV) chromophore, attachment to the antibody protein is detected by a distinct change in the spectrum of the retained antibody.

Particularly, the formation of ADC (activated cytotoxic compound attached to a targeting molecule) with Trastuzumab and ON 14013100 (an NHS-activated prodrug of ON 013100) is monitored by collecting UV spectra during SEC analysis. The formation of the ADC is accompanied by an increase in the adsorption of the antibody molecule at 315 nm. The elution peak of the protein widens during the conjugation. This is due likely to increased interaction between the antibody and the SEC column (TSK-GEL SuperSW3000, Tosoh Bioscience LLC). This method is useful in determining the extent of the reaction and may be applied to large-scale purification of the ADC.

Example X

In Vitro Cell Death Efficacy

Cell based toxicity assays are used to determine $IC_{50}$ values of immunoconjugates against antigen positive and negative expressing cell lines. The cell killing activity of each immunoconjugate is determined using two assay systems. The first method tests the cell killing activity of the immunoconjugate using a 96-hour continuous exposure dose response assay described. The second assay, a short-term treatment in order to more closely mimic the clinical setting, is used for immunoconjugates that have been found to be positive in the initial screening assay. To accomplish these studies the cell lines are divided into two classes, antigen positive and antigen negative. This application develops specific immunoconjugates for HER2 expressing and CD38/CD138 expressing tumor cells. The following cell lines, previously tested and described herein, are used (Table 7).

These cell lines are available from the American Type Culture Collection (ATCC) or the German Repository (DSMZ). The antigen status of each cell line has been fully characterized in a number of references (MM cell lines). Pellat-Deceunynk, C., et al., *Human Myeloma Cell Lines As A Tool For Studying The Biology Of Multiple Myeloma: A Reappraisal 18 Years After*, Blood 86(10):4001-2 (1995); Gooding, R. P., et al., *Phenotypic And Molecular Analysis Of Six Human Cell Lines Derived From Patients With Plasma Cell Dyscrasia*, British Journal of Haematology 106:669-688 (1999); Marx C., et al., *Validated High-Throughput Screening of Drug-Like Small Molecules for Inhibitors of ErbB2 Transcription*. Assay Drug Dev. Technology 4(3):273-84 (2006); Lostumbo, A., et al., *Flow Cytometry: A New Approach For The Molecular Profiling Of Breast Cancer*, Exp. and Molecular Pathology 80:46-53 (2006). The use of antigen positive and antigen negative cell lines enables the determination of the specificity of the immunoconjugates while simultaneously determining cytotoxic activity. Immunoconjugates derived for each tumor model are tested against the appropriate cell lines.

Cells are plated into 12-well dishes at a cell density of $2.5 \times 10^4$ cell/well in the appropriate growth medium. The following day, the cells are treated with 10 fold increasing concentrations of each immunoconjugate starting at 0.01 μg/ml up to 1000 μg/ml. The cells are also treated with unmodified antibody at the same concentration, free compound (1 nM-10 nM), and vehicle. The total number of viable cells is determined by trypan blue exclusion and counting using a hemacytometer. The percent of viable cells compared to the vehicle treated are plotted and the $IC_{50}$ value is determined. The cells are tested in duplicate wells and each complete experiment is repeated. Immunoconjugates that are found to be cytotoxic in the initial test are retested at concentrations within a 10-fold range to provide accurate $IC_{50}$ values.

Immunoconjugates are classified as positive based on a number of parameters. Positive immunoconjugates should have $IC_{50}$ values significantly lower than the primary non-conjugated antibody with $IC_{50}$ values below 10 μg/ml. In addition, the immunoconjugates should retain their specificity towards cell lines that express the target antigens.

Positive immunoconjugates that exhibit high potency and selectivity are tested in a washout assay system. Particularly, the cell is plated as described above, and treated for short-term periods, 1 hr-4 hrs, then the cells are washed 3× with normal growth medium. Growth medium without the immunoconjugates is then placed back into each well. The cells are incubated for an additional 95-92 hours. Total number of viable cells is then determined as described.

Example XI

Binding Studies

Each immunoconjugate is tested for relative binding potential by flow cytometry assays. This data supports the cytotoxicity data and allows correlation between exhibited cell killing activity and binding.

Immunoconjugates and their respective non-conjugated antibodies are labeled with FITC to perform FACS analysis. The labeling procedure is performed following the instructions provided by the manufacturers (Molecular Probes, Inc.). Once the immunoconjugates and the primary antibodies have been labeled with FITC, the FITC-conjugated products are incubated with antigen positive and negative cells in the following manner and then subjected to FACS analysis. Antigen positive and negative cells are grown in growth medium to a cell density of 70-80% confluency in order to limit cell clumping. The cells are removed from the plates by treatment with a non-enzymatic cell dissociation solution (Sigma). The cells are washed in PBS and counted. Cells are spun down and resuspended in staining buffer (eBiosciences) to give a cell density of $2.0 \times 10^7$ cells/ml. For the staining procedure, 50 ul of cell suspension ($1.0 \times 10^6$ cells) is incubated with FITC-conjugated products and an isotype control at 4° C. in the dark. Following the labeling period, the cells are fixed and analyzed by basic flow cytometry techniques. Specificity is determined by the comparing the amount of binding between the antigen positive and negative cell lines.

Example XII

Evaluation of in Vivo Tumor Growth Inhibition and Selectivity Using a Nude Mouse Model System Immunoconjugates identified as positives in the cell based assay system are tested for their ability to inhibit the growth of tumors in a nude mouse model system. The immunoconjugates are compared to the parental primary antibody for both tumor growth inhibition and selectivity. Immunoconjugates are synthesized and purified. Before testing in the mouse system, each batch/lot is tested in the in vitro cytotoxicity assay to ensure that cell killing activity and selectivity has not changed.

Determination of Maximum Tolerated Dose (MTD)

A small-scale toxicity study is first performed in mice to determine the Maximum Tolerated Dose (MTD) which allows the determination of the dose range for each immunoconjugate. Outbred female CD-1 mice (N=3) are be treated with increasing doses (dose escalation) of the immunoconjugate and the primary antibody as a reference. The animals are injected intravenously with a single dose in the following range, 0.100 mg/kg to 4 mg/kg. The mice are observed for 14 days. Body weights are taken daily. Physical signs of toxicity are monitored. Upon determination of the MTD, the efficacy studies proceed beginning with a dose of ½ the MTD.

Nude Mouse Xenografts

Female nude mice (ncr/ncr) are housed in Hep-filtered sterile cages with filtered forced air. All food and water is sterile. Mice are injected subcutaneously with either ($1.0 \times 10^7$) antigen positive or negative cells in their hindquarter. The tumors are allowed to grow until the average tumor volume reaches 50 mm³. The mice are divided (N=8) into treatment groups in a random manner. The following is a list of the experimental groups: 1. Primary antibody, 2. Immunoconjugate, 3. Vehicle (PBS) control. Dose and schedule vary depending on results from initial toxicity experiments and the tumor model being tested. The initial dose and schedule are modeled after the following published studies, HER2: (Mandler, 2004), CD138: (Tassone, 2004) and modified based on MTD studies. Table (8) depicts a typical experiment. The animals are treated intravenously with equal doses of primary antibodies and immunoconjugates everyday for 5 days (QDx5), or once weekly with an equivalent accumulative dose for ($Q_7Dx3$) weeks. The dose of the $Q_7D$ groups is very close to the MTD as determined above. The same format is used for the multiple myeloma studies but the cell lines are different. Tumor growth and body weight are monitored three times a week for the duration of the experiment. Signs of toxicity are monitored by body weight, and changes in physical appearance such as tremors, paralysis, blindness, and posture. If signs of toxicity are exhibited or efficacy is not observed at the initial dose and schedule the experimental system is further modified by increasing the overall dose or by changing the schedule. Tumor measurements are performed using vernier calipers, measuring in two dimensions. Tumor volume is calculated by the following formula:

$(Short)^2 \times Long \times 0.5$.

Example XIII

Synthesis of N-Glutarylethylenediamine Ureas of (E)-2,4,6-trimethoxystyryl-4-methoxy-3-aminobenzylsulfone (ON 01500) (Accordingly, this Example Properly Follows Example I)

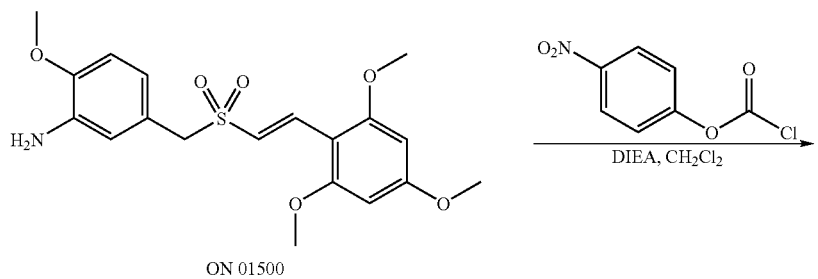

ON 01500

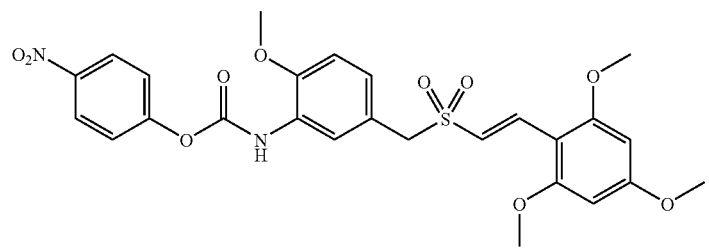

ON 01500, para-Nitrophenyl Carbamate

ON 01500, para-Nitrophenyl Carbamate (MW=558.56)

To a vigorously stirring slurry containing ON 01500 (300.0 mg, 0.76 mmol), para-nitrophenyl chloroformate (153.7 mg, 0.76 mmol), and $CH_2Cl_2$ (7.6 mL) was added diisopropylethylamine (DIEA) (126.2 μL, 0.76 mmol) dropwise via pipet. The reaction immediately became a transparent, homogeneous solution. Progress of the reaction was monitored by thin layer chromatography (TLC) using 2:1 ethyl acetate/hexanes. Reaction was clean and complete within 90 minutes. The crude product was used without workup and purification. Mass spectroscopic data could not be obtained directly for this compound. However, when crude product solution was reacted 1:1 with 4-Amino-1-BOC-piperidine (Aldrich), a mass peak representing the $M+Na^+$ ion (642.1) was observed.

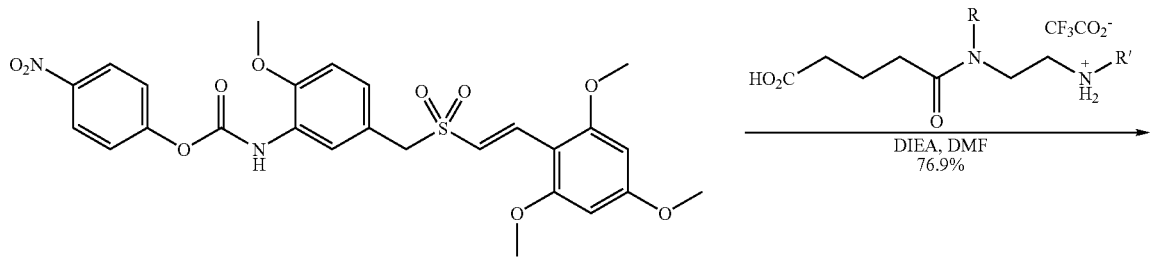

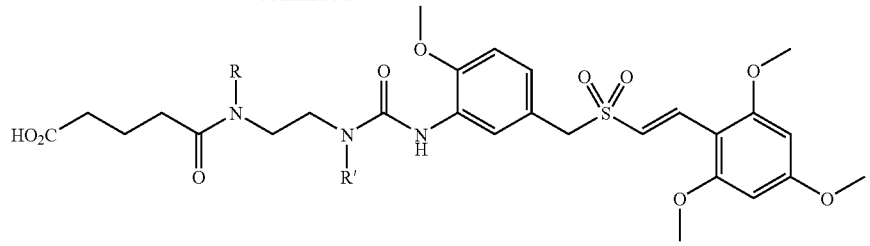

ON 01500,
N-Glutaryl-N,N'-dimethylethylenediamine Urea
(R=R'=Me; MW=621.70)

N-Hydroxysuccinimidyl Ester of ON 01500,
N-Glutaryl-N,N'-dimethylethylenediamine Urea
(R=R'=Me; MW=718.77)

To a solution containing ON 01500, para-nitrophenyl carbamate (92.8 mg, 0.17 mmol) and glutaryl N,N'-dimethylethylenediamine trifluoroacetate (55.2 mg, 0.174 mmol, 1.05 equiv) in DMF (1.66 mL) was added diisopropylethylamine (DIEA) (144.7 µL, 0.83 mmol, 5.0 equiv) dropwise via syringe. Immediately, the reaction solution turned bright yellow, and was stirred overnight at room temperature. After this time, the reaction was concentrated to near complete dryness and the product purified via flash silica chromatography (95:4:1 ethyl acetate/methanol/acetic acid). Chromatography fractions were combined and azeotroped with toluene to remove residual acetic acide.

Yield=79.4 mg (76.9%); Mass observed: 622.1; M+Na$^+$=645.2.

ON 01500, N-Glutaryl-N-methylethylenediamine Urea (R=Me; R'=H; MW=607.67)

Prepared according to the procedure described for ON 01500, N-Glutaryl-N,N'-dimethylethylenediamine urea (shown above). Yield=119.7 mg (77.6%) as a white powder; Mass observed: 608.1; M+Na$^+$=630.2.

ON 01500, N-Glutaryl-N'-methylethylenediamine Urea (R=H; R'=Me; MW=607.67)

Prepared according to the procedure described for ON 01500, N-Glutaryl-N,N'-dimethylethylenediamine urea (shown above). Yield=65.8 mg (42.6%; unoptimized) as a white powder; Mass observed: 608.1; M+Na$^+$=630.2.

ON 01500, N-Glutarylethylenediamine Urea (R=R'=H; MW=593.65)

Prepared according to the procedure described for ON 01500, N-Glutaryl-N,N'-dimethylethylenediamine urea (shown above). Yield=102.0 mg (33.8%; unoptimized) as a white solid.

To a solution containing ON 01500, N-glutaryl-N,N'-dimethylethylenediamine urea (21.3 mg, 34.3 µmol), N-hydroxysuccinimide (7.9 mg, 68.5 µmol, 2.0 equiv), and dry DMF (340 µL) was added 1-(3-dimethylaminopropyl)-3-ethylcarbodiimide hydrochloride (EDCI) in a single heap. The mixture was allowed to stir at room temperature overnight. DMF was then removed in vacuo, and ethyl acetate (20 mL) was added to the crude residue, and the resulting mixture washed with water (20 mL). The organic layer was washed with additional water (2×10 mL), washed with brine (10 mL), and then dried over sodium sulfate. The drying agent was removed via filtration, and the crude product (single spot by thin layer chromatography; 95:4:1 ethyl acetate/methanol/acetic acid) was concentrated by rotary evaporation, followed by high vacuum. Yield=20.6 mg (83.7%) as a foamy oil/solid. Mass observed: 719.1; M+Na$^+$=742.2

N-Hydroxysuccinimidyl ester of ON 01500, N-Glutaryl-N-methylethylenediamine Urea (R=Me; R'=H; MW=704.75)

Prepared from ON 01500, N-Glutaryl-N-methylethylenediamine urea (54.8 mg, 90.0 µmol) according to the procedure described for the N-Hydroxysuccinimidyl ester of ON 01500, N-Glutaryl-N,N'-dimethylethylenediamine urea (shown above). Yield=32.4 mg (51.0%; unoptimized) as an off-white solid.

N-Hydroxysuccinimidyl ester of ON 01500, N-Glutaryl-N'-methylethylenediamine Urea (R=H; R'=Me; MW=704.75)

Prepared from ON 01500, N-Glutaryl-N'-methylethylenediamine urea (25.0 mg, 41.1 µmol) according to the procedure

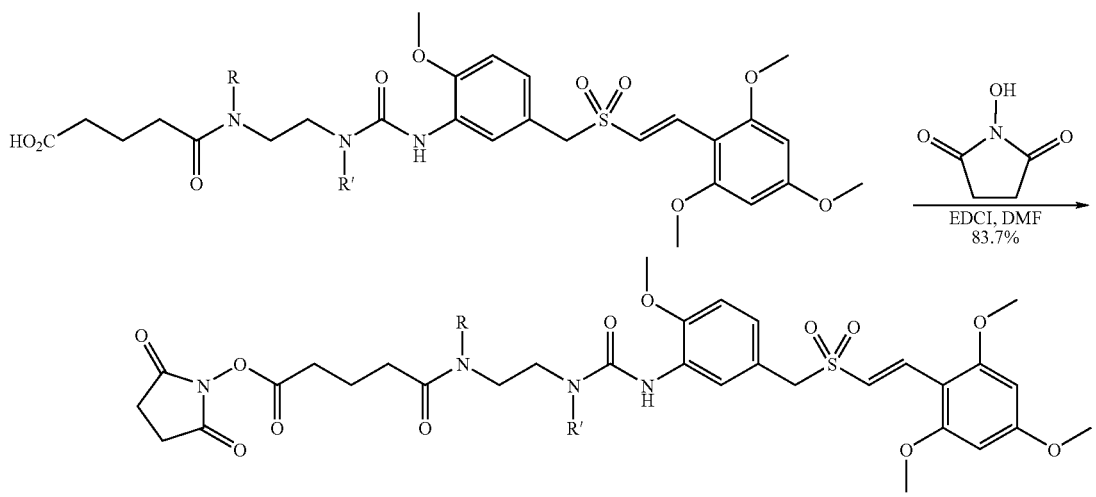

described for the N-Hydroxysuccinimidyl ester of ON 01500, N-Glutaryl-N,N'-dimethylethylenediamine urea (shown above). Yield=27.4 mg (94.8%) as an off-white solid.

N-Hydroxysuccinimidyl ester of ON 01500, N-Glutaryl-ethylenediamine Urea (R=R'=H; MW=690.72)

Prepared from ON 01500, N-Glutarylethylenediamine urea (25.0 mg, 42.1 μmol) according to the procedure described for the N-Hydroxysuccinimidyl ester of ON 01500, N-Glutaryl-N,N'-dimethylethylenediamine urea (shown above). Yield=8.9 mg (30.6%; unoptimized) as an off-white solid.

Example XIV

Synthesis of 4-(N-tert-Butoxycarbonylamino)butyramides of (E)-2,4,6-trimethoxystyryl-4-methoxy-3-aminobenzylsulfone (ON 01500) (GABA Amides of ON 01500)

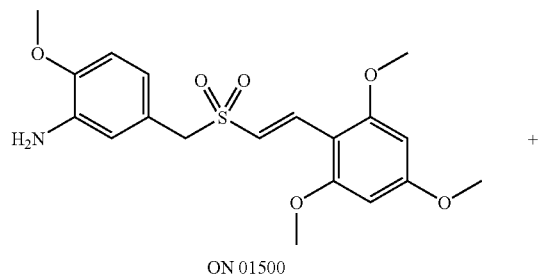
ON 01500

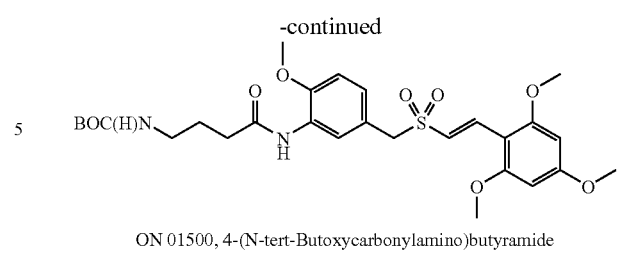
ON 01500, 4-(N-tert-Butoxycarbonylamino)butyramide

ON 01500, 4-(N-tert-Butoxycarbonylamino)butyramide (MW=578.68)

To a stirring solution containing ON 01500 (1.0 g, 2.54 mmol), BOC-γ-aminobutyric acid (516.4 mg, 2.54 mmol), DMF (13 mL), and diisoproplyethylamine (DIEA) (664.0 μL, 3.81, 1.5 equiv) was added 1-(3-Dimethylaminopropyl)-3-ethylcarbodiimide hydrochloride (EDCI) (730.9 mg, 3.81 mmol, 1.5 equiv) in a single heap. The reaction was stirred overnight, at which time TLC showed that the reaction was incomplete by the presence of unreacted ON 01500. The reaction was charged with additional BOC-γ-aminobutyric acid (774.7 mg, 3.81 mmol, 1.5 equiv) and EDCI (730.9 mg, 3.81 mmol, 1.5 equiv). After an additional hour of stirring, the reaction was concentrated to near dryness. To the crude residue was added ethyl acetate (50 mL) and H₂O (50 mL) with thorough mixing. The layers were separated, and the organic layer was washed with H₂O (2×25 mL), brine (25 mL), and dried over sodium sulfate. The crude product was filter and concentrated by rotary evaporation. Purification of the crude product via flash silica chromatography (85 g silica; 2:1-3:1 EtoAc/hexanes) provided 973.9 mg (66.3%) as a white powder, as well as impure material that can be recycled.

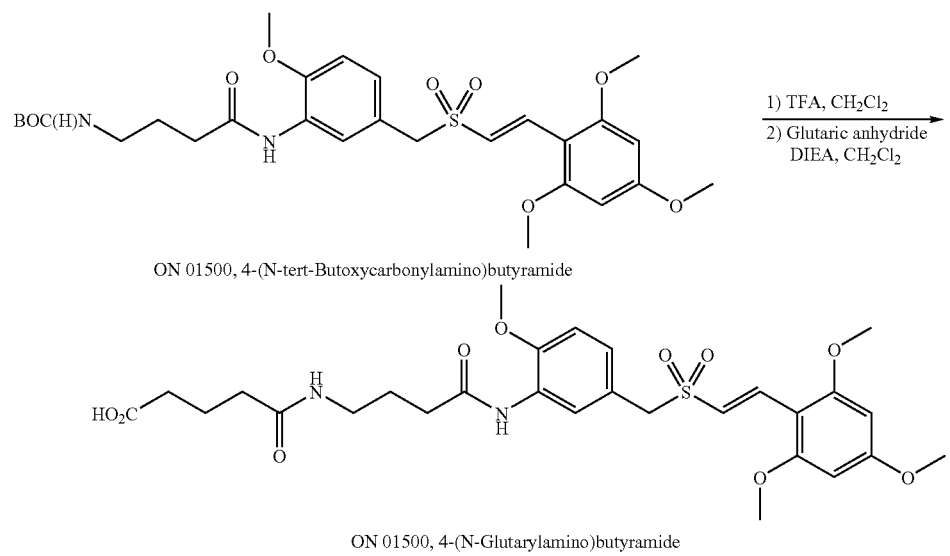

-continued

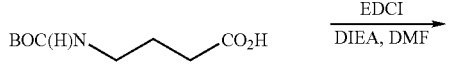

ON 01500, 4-(N-Glutarylamino)butyramide (MW=592.66)

To a stirring solution of ON 01500, 4-(tert-butoxycarbonylamino)butyramide (198.7 mg, 0.34 mmol) and CH₂Cl₂ (2.0 mL) was added a solution of trifluoroacetic acid (TFA) (510.1 μL, 6.87 mmol, 20.0 equiv) dropwise via pipet over two minutes. Immediately, the reaction turned a light red wine color. Within 15 minutes, thin layer chromatography (TLC) showed that most of the starting material was consumed. The reaction was concentrated to near complete dryness and CH$_2$Cl$_2$ (10 mL) was added to redissolve the crude product, and the resulting solution reconcentrated by rotary evaporation. Repeated this process one more time to remove any excess TFA. To the crude TFA salt product was added glutaric anhydride (117.5 mg, 1.03 mmol, 3.0 equiv), CH$_2$Cl$_2$ (2.2 mL), and DIEA (113.5 µL, 0.68 mmol, 2.0 equiv), and the resulting mixture was stirred overnight. A fine white precipitate formed, and TLC showed that a three-component mixture has formed. The white precipitate was isolated by Buchner filtration and washed with copious amounts of CH$_2$Cl$_2$. After drying under high vacuum, the yield was 107.7 mg (52.9%). Mass observed=593.0.

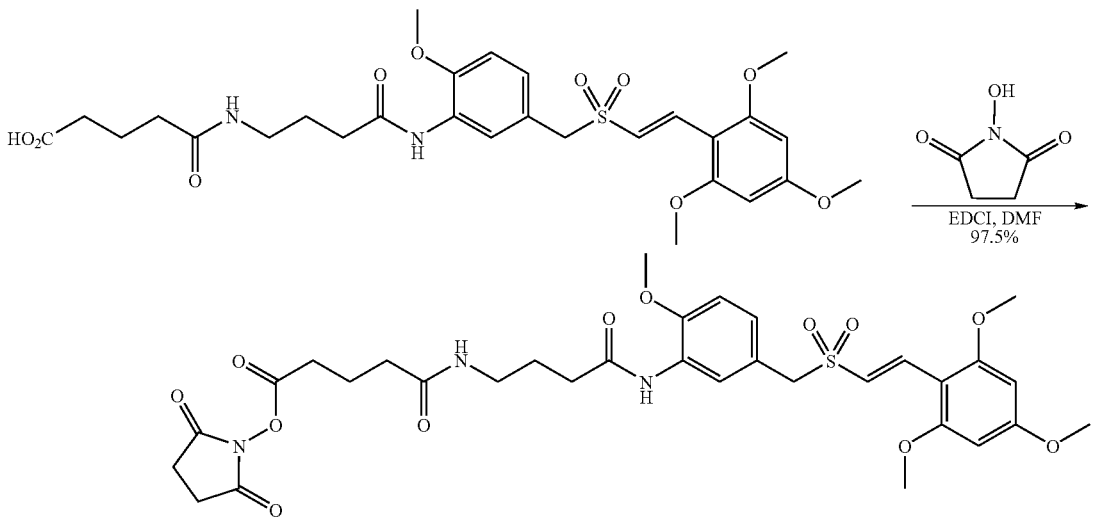

N-Hydroxysuccinimide ester of ON 01500, 4-(N-Glutarylamino)butyramide (MW=689.73)

To a mixture containing ON 01500, 4-(N-Glutarylamino) butyramide (54.0 mg, 91.1 µmol), DMW (1.0 mL), and N-hydroxysuccinimide (52.4 mg, 0.46 mmol, 5.0 equiv), was added EDCI (87.3 mg, 0.46 mmol, 5.0 equiv) in a single heap. The reaction was allowed to stir at room temperature overnight and was monitored by TLC (90:9:1 ethyl acetate/ MeOH/acetic acid). The reaction was then concentrated to near dryness and the product was extracted from a mixture of EtOAc (15 mL) and H$_2$O (15 mL). The organic layer was washed with additional H$_2$O (2×15 mL), brine (15 mL), dried over Na$_2$SO$_4$, filtered and concentrated, yielding 61.3 mg (97.5%) of a white solid that was pure by TLC.

Example XV 3-(4-Carboxyphenyl)propionate Spacer Linker

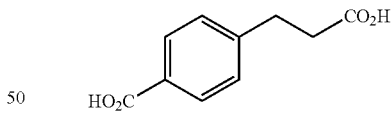

3-(4-Carboxyphenyl)propionic Acid

Purpose: Incorporation of an aromatic ring adjacent to the amide bond linkage between the spacer linker and self-immolative linker (i.e., designed scissile bond) is anticipated to exploit alternative protease activity within tumor or target cells.

3-(4-Carboxyphenyl)propionate spacer linker is attached, for example, to ethylenediamine-linked ON 013100 series. However, any cytotoxic drug selected from the group consisting of AMINO-SUBSTITUTED (E)-2,6-DIALKOXY-STYRYL 4-SUBSTITUTED BENZYLSULFONES, AMINO-AND-HYDROXY SUBSTITUTED STYRYL-SULFONANILIDES, and SUBSTITUTED PHENOXY- AND PHENYLTHIO-STYRYLSULFONE DERIVATIVES, e.g., ON 01500, can be used.

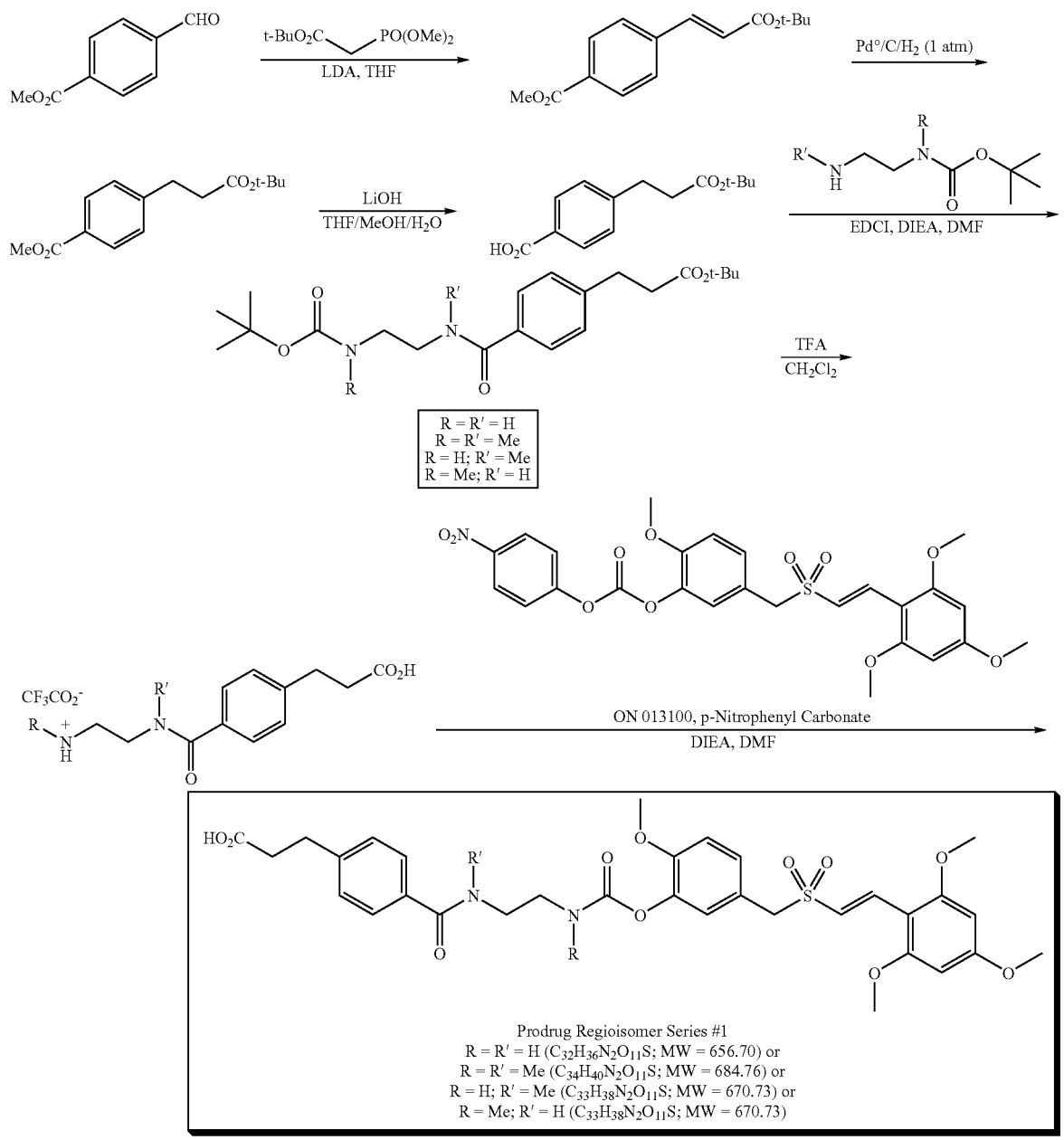
Alternatively, regioisomeric prodrugs derived from the 3-(4-Carboxyphenyl)propionate spacer linker can be obtained from a different example synthetic route, as shown here:
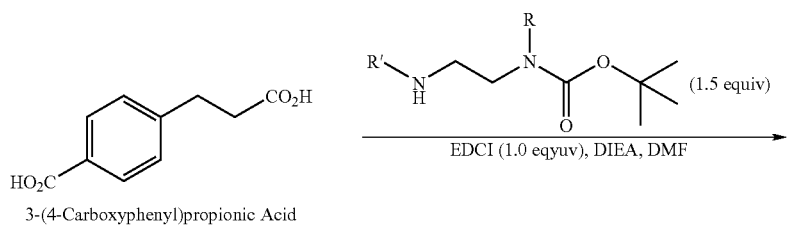
3-(4-Carboxyphenyl)propionic Acid -continued

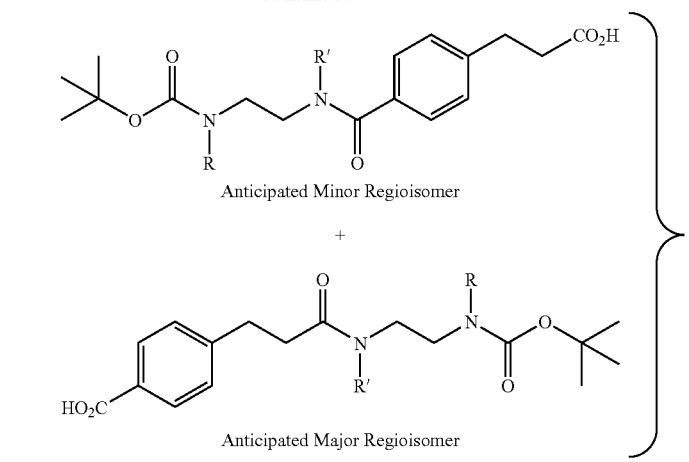

Anticipated Minor Regioisomer

+

Anticipated Major Regioisomer

Separable from "Bis-Adduct" via bicarbonate extraction from an organic solvent such as ethyl acetate. Both mono-adduct regioisomers expected to be readily separated from each other using standard flash silica chromatography

+

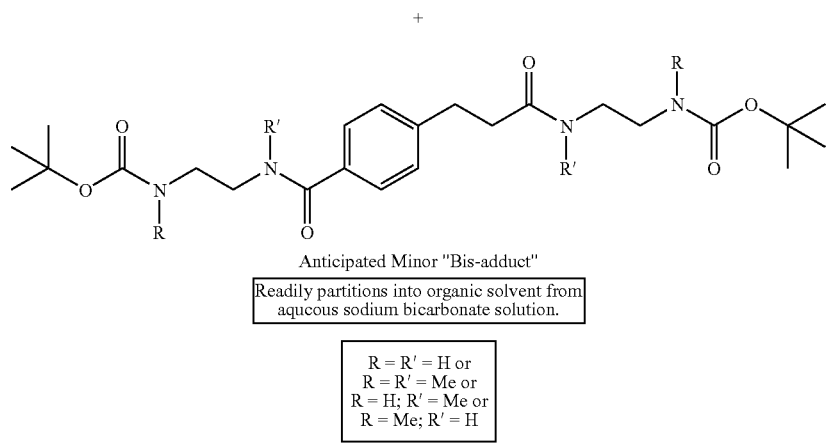

Anticipated Minor "Bis-adduct"

Readily partitions into organic solvent from aqueous sodium bicarbonate solution.

R = R' = H or
R = R' = Me or
R = H; R' = Me or
R = Me; R' = H

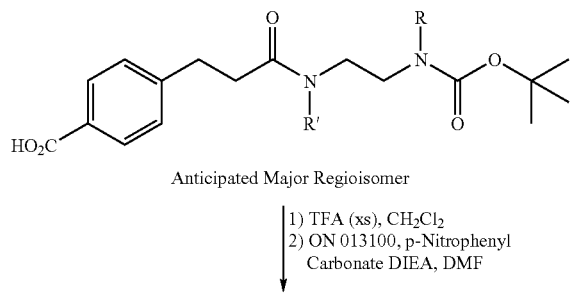

Anticipated Major Regioisomer

1) TFA (xs), CH$_2$Cl$_2$
2) ON 013100, p-Nitrophenyl Carbonate DIEA, DMF

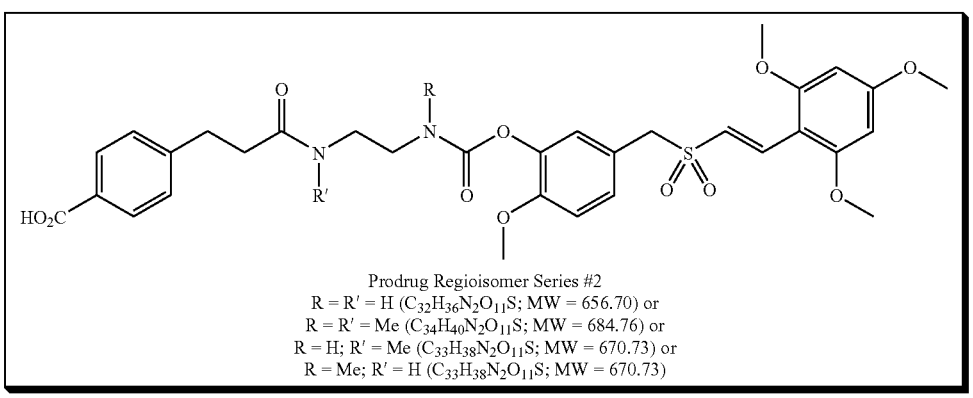

Prodrug Regioisomer Series #2
R = R' = H (C$_{32}$H$_{36}$N$_2$O$_{11}$S; MW = 656.70) or
R = R' = Me (C$_{34}$H$_{40}$N$_2$O$_{11}$S; MW = 684.76) or
R = H; R' = Me (C$_{33}$H$_{38}$N$_2$O$_{11}$S; MW = 670.73) or
R = Me; R' = H (C$_{33}$H$_{38}$N$_2$O$_{11}$S; MW = 670.73)

Example XVI
Method to Prepare Maleimido-Labelled Prodrugs for Conjugation
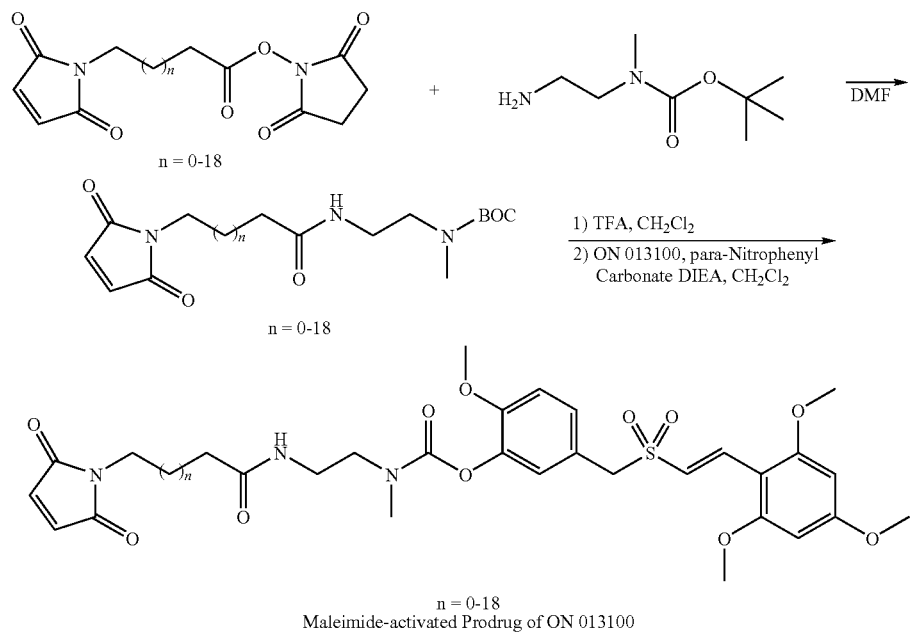
For Example:
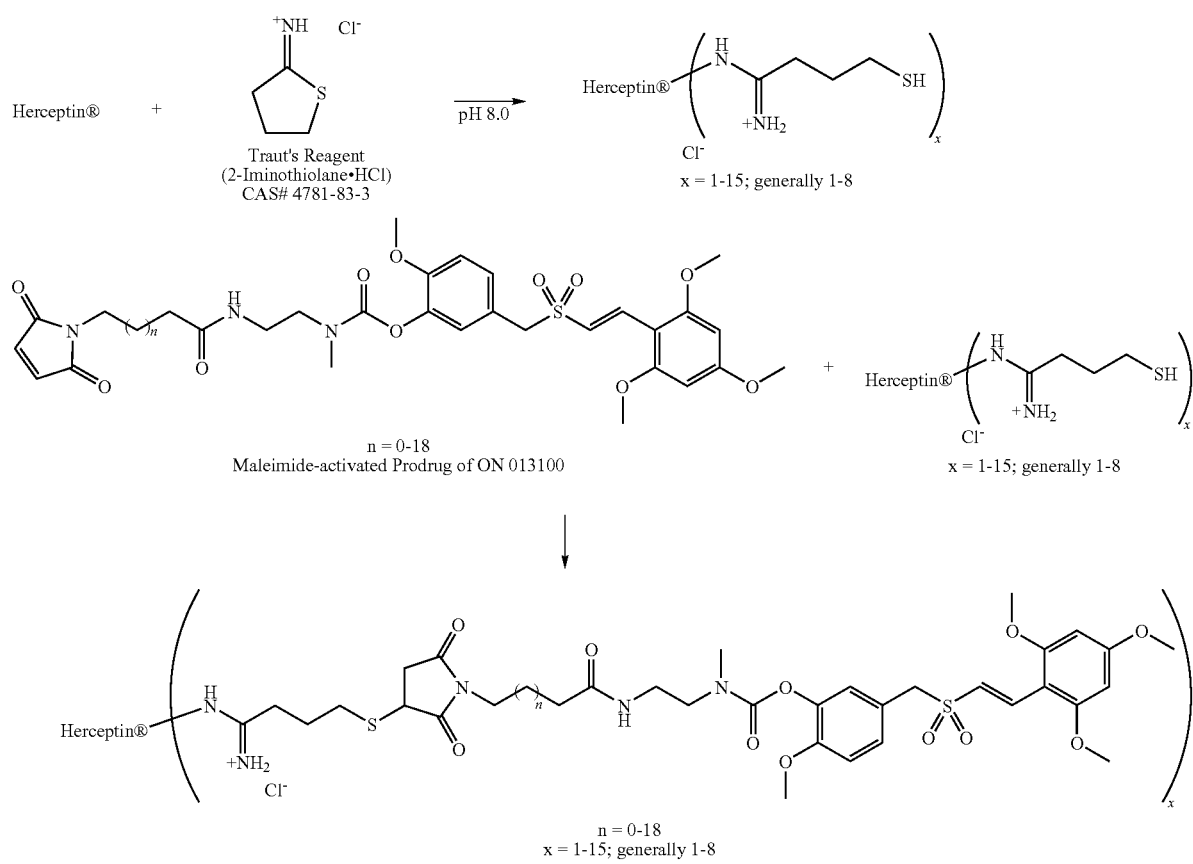

All publications and patents referred to herein are incorporated by reference. Various modifications and variations of the described subject matter will be apparent to those skilled in the art without departing from the scope and spirit of the invention. Although the invention has been described in connection with specific embodiments, it should be understood that the invention as claimed should not be unduly limited to these embodiments. Indeed, various modifications for carrying out the invention are obvious to those skilled in the art and are intended to be within the scope of the following claims.

What is claimed is:

1. An activated cytotoxic compound for attachment to a targeting molecule for the treatment of proliferative disorders comprising, an activator, a spacer linker, a linker, and a cytotoxic drug wherein the linker is a self-immolative linker is para-Aminobenzyl Alcohol (PABA), 3,3-Dimethyl-4-hydroxybutyric Acid, an Ethylenediamine, γ-Aminobutyric Acid (GABA), 2-Hydroxycinnamic Acid, "Trimethyl Lock", or an Ethanolamine and the spacer linker comprises Glutaryl, Diglycoyl, Succinyl, Homophthalyl, or Amino-PEG-Acid; wherein the activated cytotoxic drug is (E)-2,4,6-trimethoxystyryl-4-methoxy-3-aminobenzylsulfone (ON 01500); (E)-5-((2,4,6-trimethoxystyrylsulfonyl)methyl)-2-methoxyphenol (ON 013100); and or (E)-2,4,6-trimethoxystyryl-4-methoxy-3-aminophenylsulfonamide (ON 24160); and wherein the activator is N-Hydroxysuccinimidyl, N-Hydroxyphthalimideyl, o-Nitrophenyl, Acyl azide, p-Nitrophenyl, N-Hydroxybenzotriazoleyl, Pentachlorophenyl, Pentafluorophenyl, or 2,4,6-trichlorophenyl.

2. The activated cytotoxic compound of claim 1, wherein the cytotoxic drug comprises (E)-2,4,6-trimethoxystyryl-4-methoxy-3-aminobenzylsulfone (ON 01500); (E)-5-((2,4,6-trimethoxystyrylsulfonyl)methyl)-2-methoxyphenol (ON 013100); or (E)-2,4,6-trimethoxystyryl-4-methoxy-3-aminophenylsulfonamide (ON 24160).

3. The activated cytotoxic compound of claim 1 selected from the group consisting of

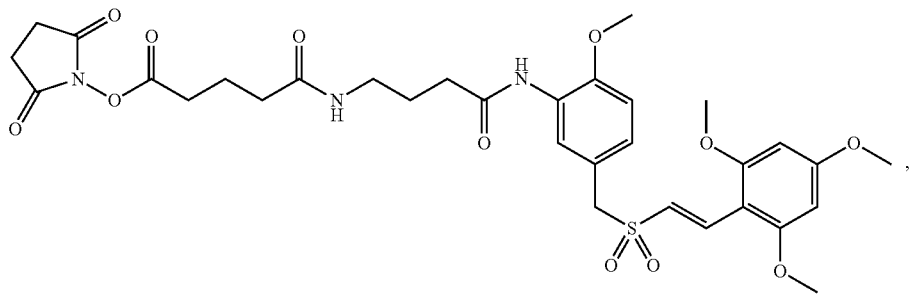

NHS-glutaryl-GABA-(ON 01500)

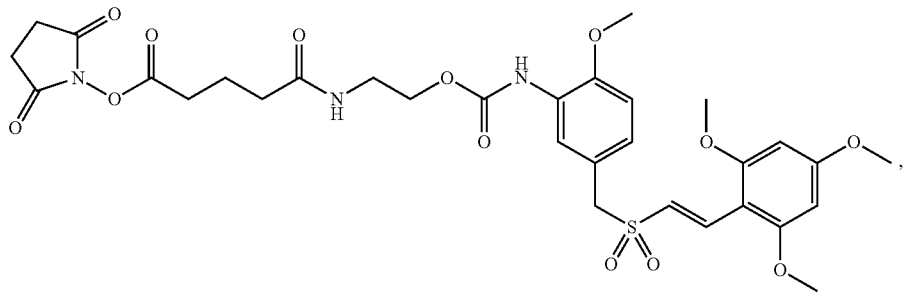

NHS-glutaryl-ethanolamine-(ON 01500)

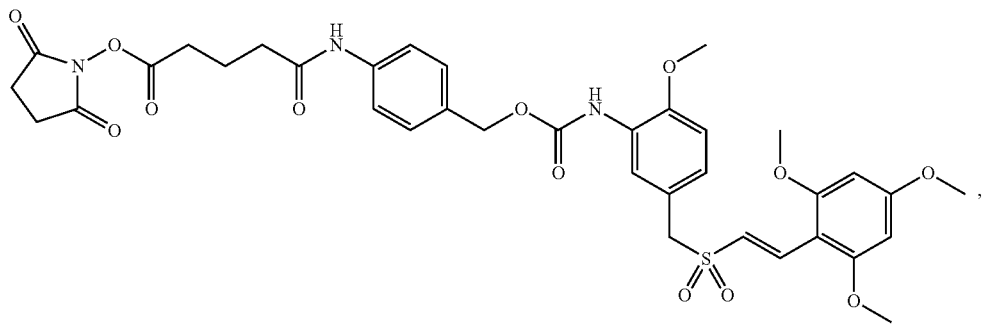

NHS-glutaryl-PABA-(ON 01500)

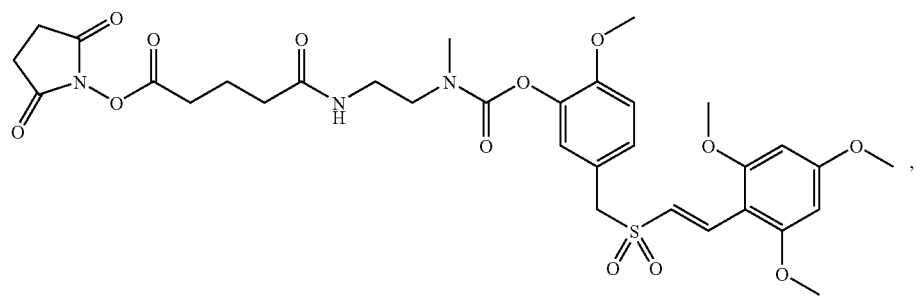
NHS-glutaryl-N-methylethylenediamine-(ON 013100)
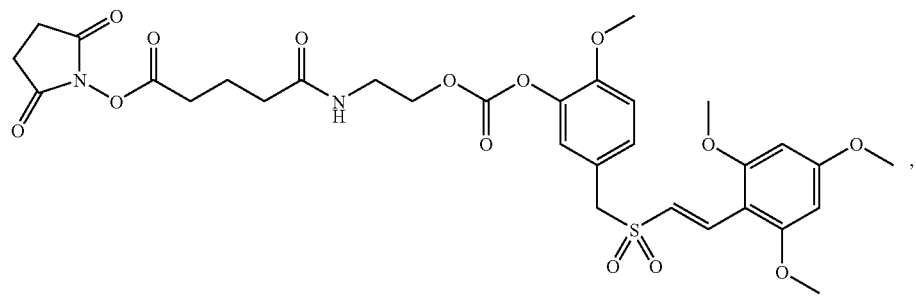
NHS-glutaryl-ethanolamine-(ON 013100)
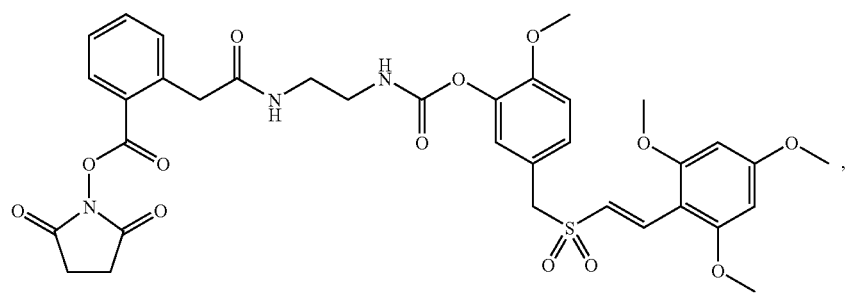
NHS-homoisophthalyl-ethylenediamine-(ON 013100)
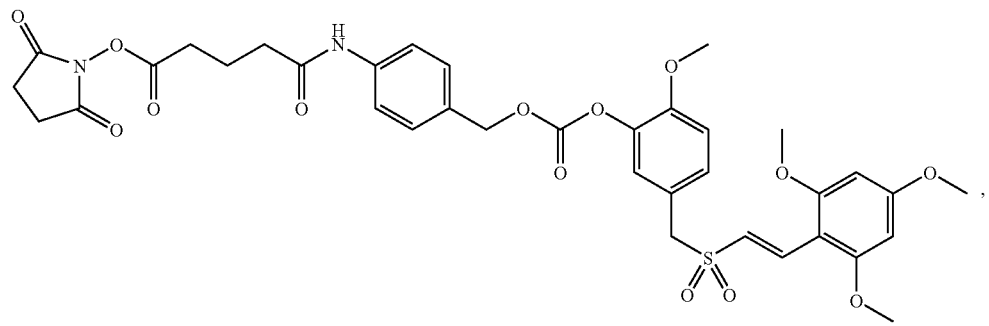
NHS-glutaryl-PABA-(ON 013100)
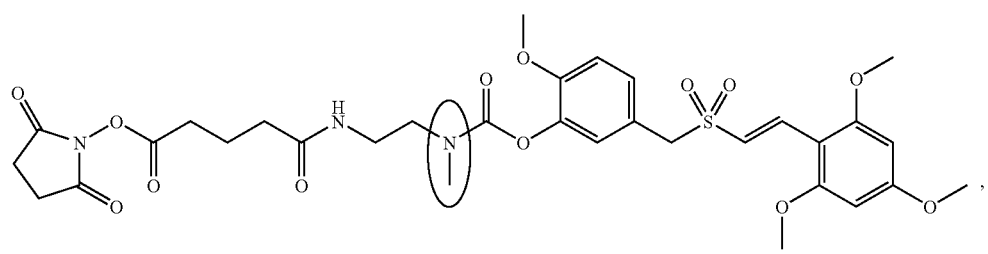
NHS-Glutaryl-N'-methylethylenediamine carbamate of ON 013100 (ON 16013100)

-continued
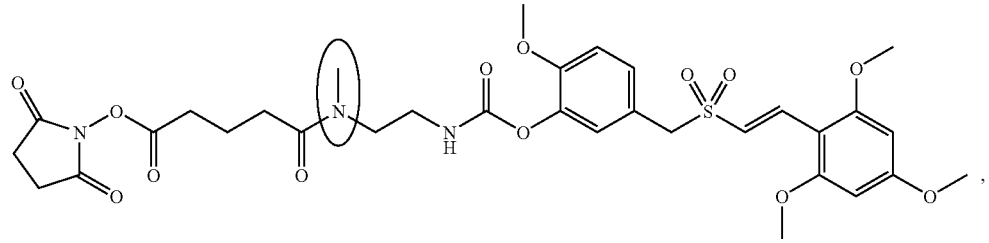
NHS-Glutaryl-N-methylethylenediamine carbamate of ON 013100
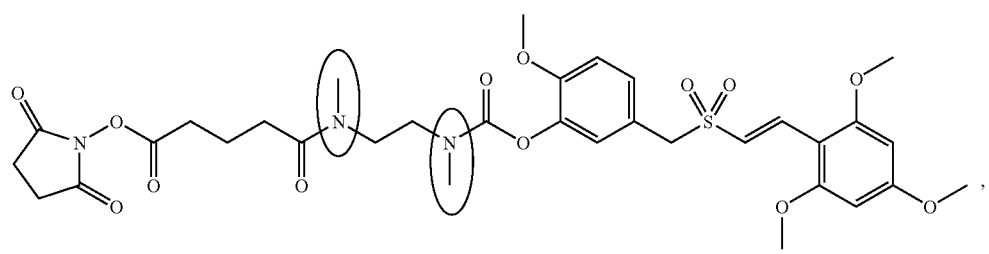
NHS-Glutaryl-N,N'-dimethylethylenediamine carbamate of ON 013100 (ON 14013100)
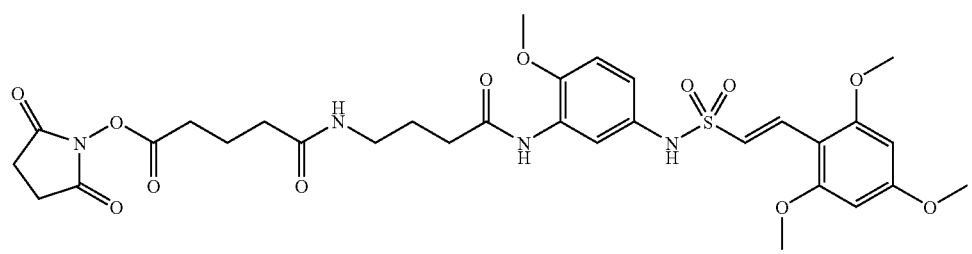
NHS-Glutaryl-GABA-(ON 24160)
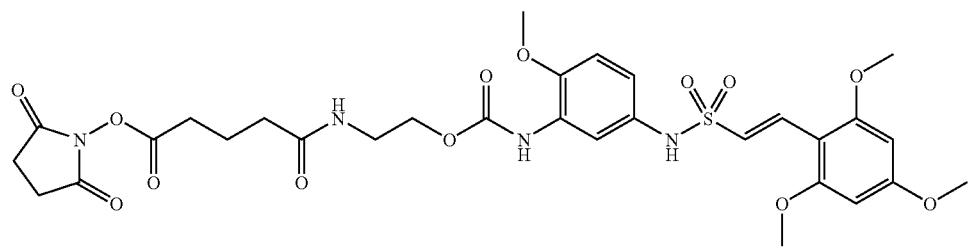
NHS-Glutaryl-ethanolamine-(ON 24160)
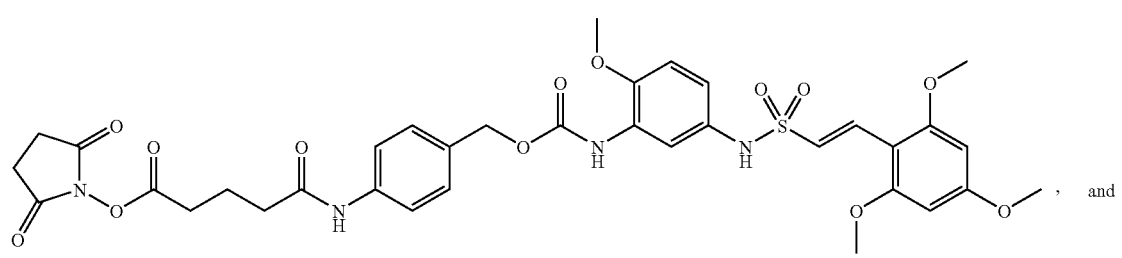
NHS-Glutaryl-PABA-(ON 24160)

-continued

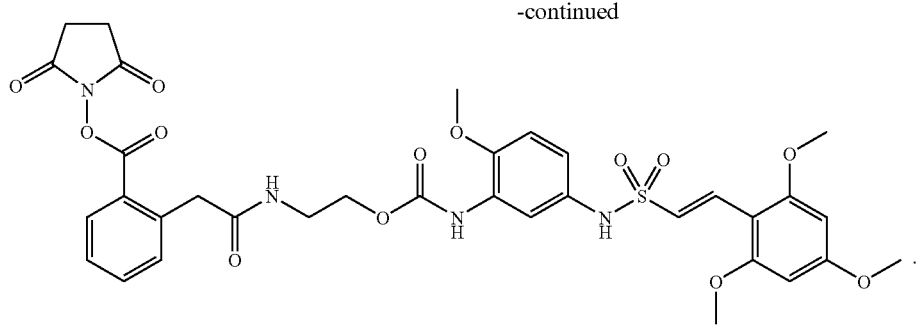

NHS-Homophthalyl-ethanolamine-(ON 24160)

4. An activated cytotoxic compound for attachment to a targeting molecule that binds a specific biological target for the treatment of proliferative disorders comprising a target molecule covalently attached to an activator, a spacer linker, a self-immolative linker, and a cytotoxic drug, wherein the self-immolative linker is para-Aminobenzyl Alcohol (PABA), 3,3-Dimethyl-4-hydroxybutyric Acid, an Ethylenediamine, γ-Aminobutyric Acid (GABA), 2-Hydroxycinnamic Acid, "Trimethyl Lock", or an Ethanolamine, and the spacer linker is Glutaryl, Diglycoyl, Succinyl, Homophthalyl, or Amino-PEG-Acid.

5. The activated cytotoxic compound of claim 4, wherein the targeting molecule is an antibody, a receptor, a ligand, a cytokine, a hormone, or a signal transduction molecule, or a combination thereof.

6. The activated cytotoxic compound of claim 5, wherein the targeting molecule is an antibody.

7. The activated cytotoxic compound claim 4, wherein the cytotoxic drug is (E)-2,4,6-trimethoxystyryl-4-methoxy-3-aminobenzylsulfone (ON 01500); (E)-5-((2,4,6-trimethoxystyrylsulfonyl)methyl)-2-methoxyphenol (ON 013100); or, (E)-2,4,6-trimethoxystyryl-4-methoxy-3-aminophenylsulfonamide (ON 24160), and the proliferative disorder is cancer.

8. The activated cytotoxic compound of claim 5, wherein the activator is N-Hydroxysuccinimideyl, N-Hydroxyphthalimideyl, o-Nitrophenyl, Acyl azide, p-Nitrophenyl, Hydroxybenzotriazole, Pentachlorophenyl, Pentafluorophenyl, or 2,4,6-trichlorophenyl.

9. The activated cytotoxic compound of claim 4, wherein the target molecule is CD138 and CD38.

10. The activated cytotoxic compound of claim 6, wherein the antibody is anti-CD138 antibodies, anti-CD38 antibodies, or HER2 antibodies.

11. The activated cytotoxic compound of claim 10, is

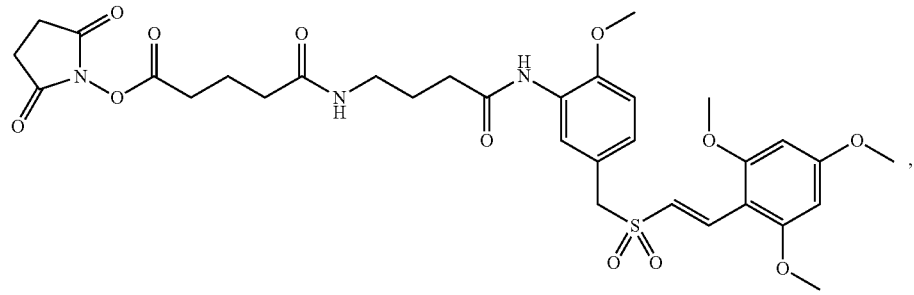

NHS-glutaryl-GABA-(ON 01500)

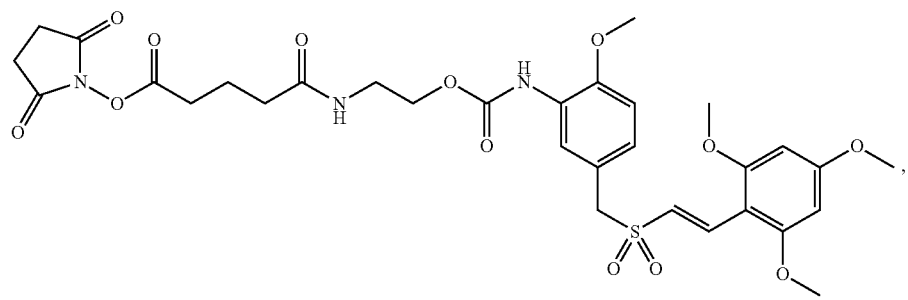

NHS-glutaryl-ethanolamine-(ON 01500)

-continued
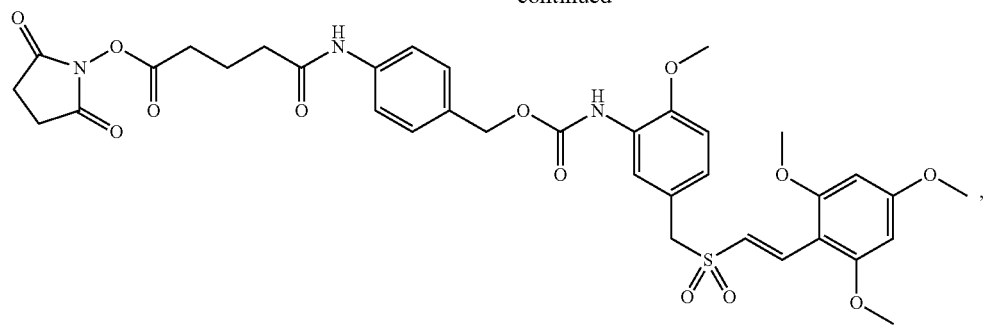
NHS-glutaryl-PABA-(ON 01500)
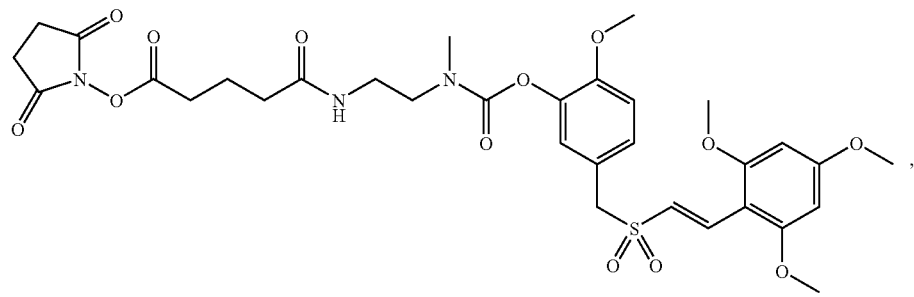
NHS-glutaryl-N-methylethylenediamine-(ON 013100)
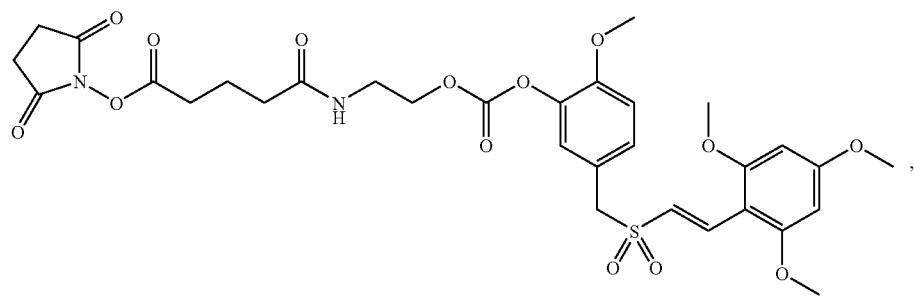
NHS-glutaryl-ethanolamine-(ON 013100)
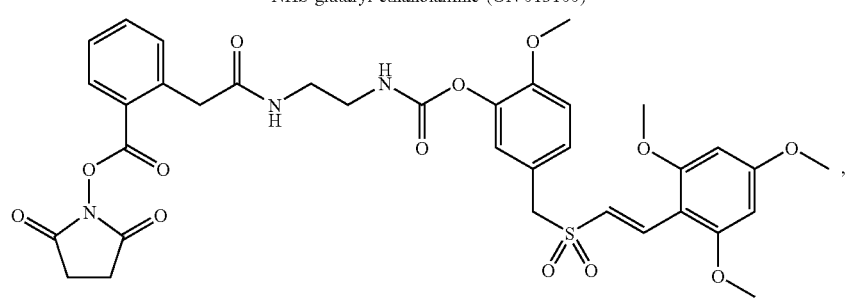
NHS-homoisophthalyl-ethylenediamine-(ON 013100)
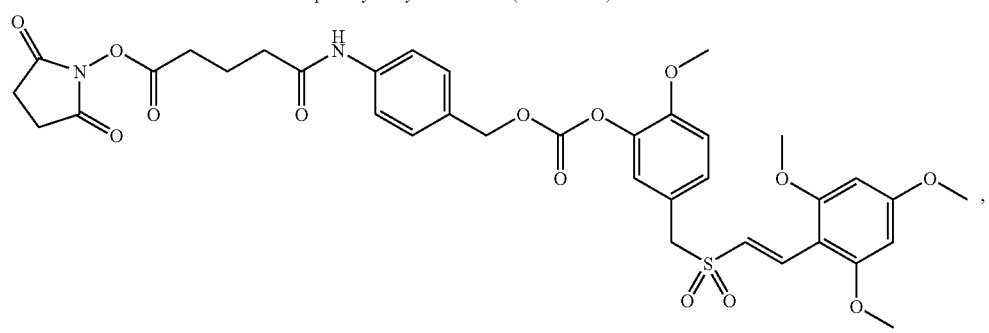
NHS-glutaryl-PABA-(ON 013100)

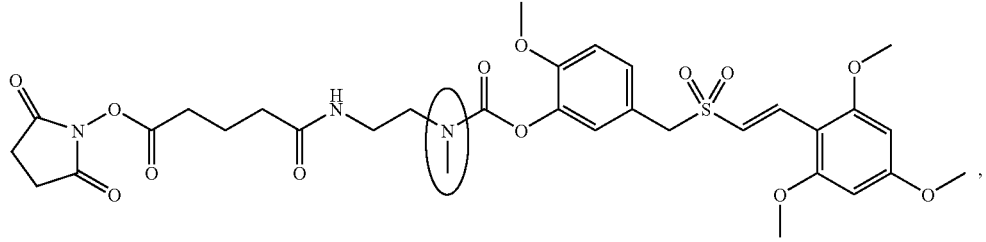
NHS-Glutaryl-N′-methylethylenediamine carbamate of ON 013100 (ON 16013100)
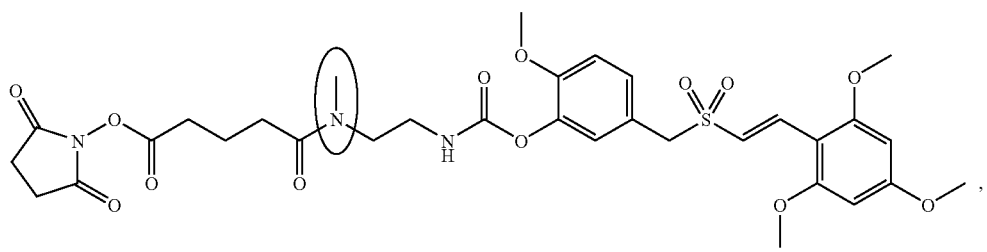
NHS-Glutaryl-N-methylethylenediamine carbamate of ON 013100
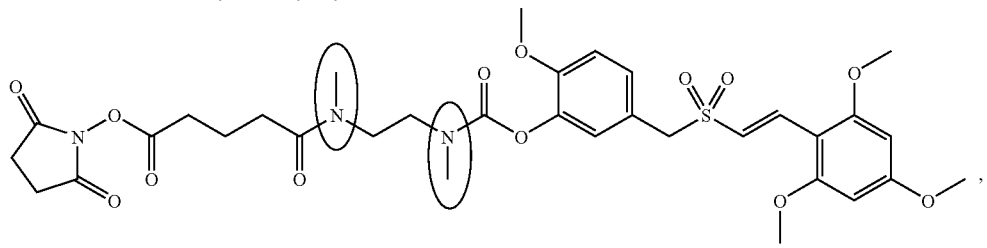
NHS-Glutaryl-N,N′-dimethylethylenediamine carbamate of ON 013100 (ON 14013100)
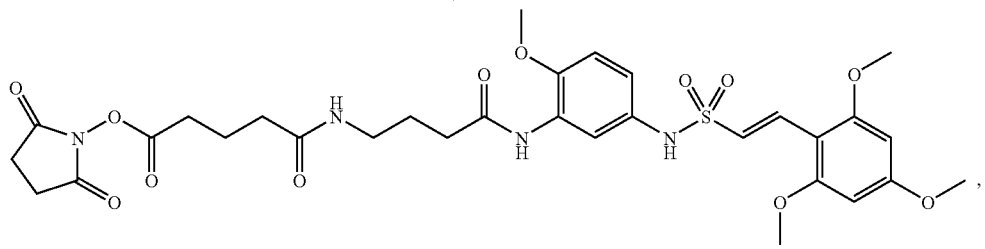
NHS-Glutaryl-GABA-(ON 24160)
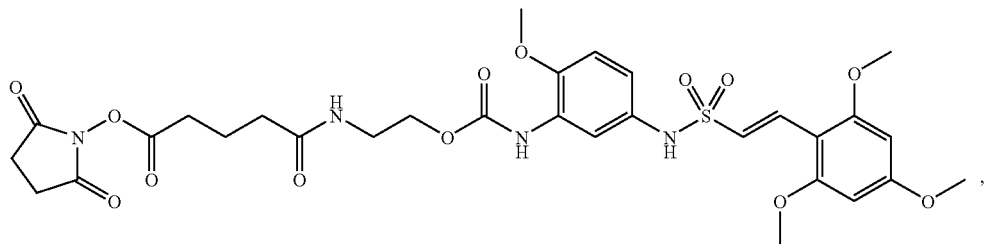
NHS-Glutaryl-ethanolamine-(ON 24160)
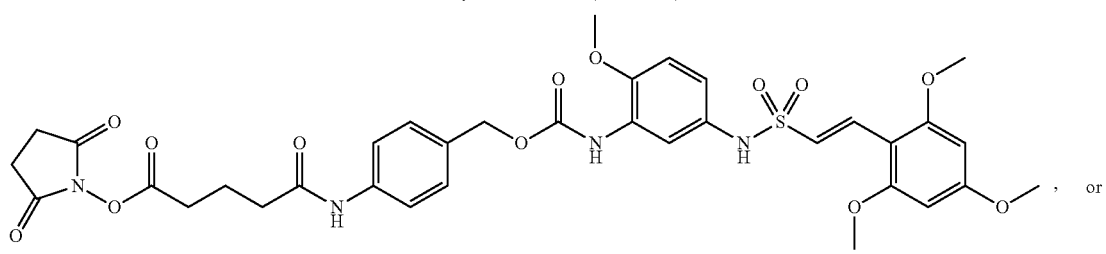
NHS-Glutaryl-PABA-(ON 24160)

-continued

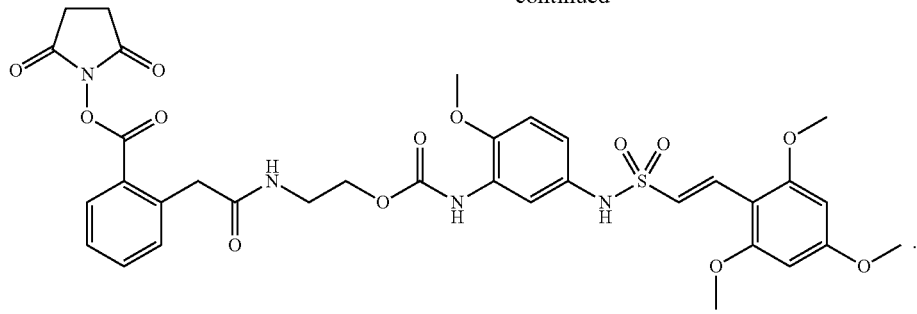

NHS-Homophthalyl-ethanolamine-(ON 24160)

12. The activated cytotoxic compound of claim 6, wherein the antibody is modified with thiol-reactive groups by partially reducing a native disulfide bridge, or by activating the cyototoxic drug with a thiol to interact with thiol reactive group on the modified antibody, or a combination of both.

13. The activated cytotoxic compound of claim 6, wherein the antibody is a monoclonal antibody directed to target antigens selectively expressed on the surface of malignant cells, or target antigens that are internalized into cancer cells, or a combination of both.

* * * * *